(12) United States Patent
Lagrange et al.

(10) Patent No.: US 9,872,822 B2
(45) Date of Patent: Jan. 23, 2018

(54) PROCESS FOR DYEING IN THE PRESENCE OF OXIDATION BASES COMPRISING AT LEAST ONE SULFONIC, SULFONAMIDE, SULFONE, AMID OR ACID GROUP AND A METAL CATALYST, DEVICE AND READY-TO-USE COMPOSITION

(71) Applicant: L'OREAL, Paris (FR)

(72) Inventors: Alain Lagrange, Coupvray (FR); Marie Mignon, Paris (FR)

(73) Assignee: L'OREAL, Paris (FR)

( * ) Notice: Subject to any disclaimer, the term of this patent is extended or adjusted under 35 U.S.C. 154(b) by 22 days.

(21) Appl. No.: 14/899,639

(22) PCT Filed: Jun. 20, 2014

(86) PCT No.: PCT/EP2014/063081
§ 371 (c)(1),
(2) Date: Dec. 18, 2015

(87) PCT Pub. No.: WO2014/202779
PCT Pub. Date: Dec. 24, 2014

(65) Prior Publication Data
US 2016/0143826 A1   May 26, 2016

(30) Foreign Application Priority Data

Jun. 21, 2013 (FR) .................................. 13 55930
Jun. 21, 2013 (FR) .................................. 13 55931

(51) Int. Cl.
| | |
|---|---|
| *A61Q 5/10* | (2006.01) |
| *A61K 8/41* | (2006.01) |
| *A61K 8/31* | (2006.01) |
| *A61K 8/34* | (2006.01) |
| *A61K 8/42* | (2006.01) |
| *A61K 8/44* | (2006.01) |
| *A61K 8/46* | (2006.01) |
| *A61K 8/19* | (2006.01) |
| *A61K 8/22* | (2006.01) |
| *A61K 8/58* | (2006.01) |
| *B65D 81/32* | (2006.01) |

(52) U.S. Cl.
CPC ............... *A61K 8/415* (2013.01); *A61K 8/19* (2013.01); *A61K 8/22* (2013.01); *A61K 8/31* (2013.01); *A61K 8/342* (2013.01); *A61K 8/411* (2013.01); *A61K 8/42* (2013.01); *A61K 8/445* (2013.01); *A61K 8/46* (2013.01); *A61K 8/466* (2013.01); *A61K 8/58* (2013.01); *A61Q 5/10* (2013.01); *B65D 81/32* (2013.01); *A61K 2800/4324* (2013.01); *A61K 2800/882* (2013.01); *A61K 2800/884* (2013.01)

(58) Field of Classification Search
CPC .......... A61K 8/31; A61K 8/445; A61K 8/466; A61K 8/19; A61K 8/58; A61K 8/46; A61K 8/415; A61K 8/411; A61K 8/22; A61K 8/342; A61K 2800/884; A61K 2800/882; A61K 2800/4324; B65D 81/32; A61Q 5/10

See application file for complete search history.

(56) References Cited

U.S. PATENT DOCUMENTS

| | | | |
|---|---|---|---|
| 4,003,699 A | 1/1977 | Rose et al. | |
| 4,137,180 A | 1/1979 | Naik et al. | |
| (Continued) | | | |

FOREIGN PATENT DOCUMENTS

| | | |
|---|---|---|
| DE | 2359399 A1 | 6/1975 |
| DE | 3843892 A1 | 6/1990 |
| (Continued) | | |

OTHER PUBLICATIONS

STIC Search Report dated Mar. 27, 2017.*
(Continued)

*Primary Examiner* — Eisa Elhilo
(74) *Attorney, Agent, or Firm* — The Marbury Law Group, PLLC

(57) ABSTRACT

The present invention relates to a process for dyeing human keratin fibres, in which use is made of one or more metal catalysts and a composition (A) comprising: (a) at least 10% by weight of one or more fatty substances, (b) one or more oxidation bases of formula (I) or (II), the addition salts thereof, solvates thereof and mixtures thereof: Formula (I), Formula (II) (c) one or more chemical oxidizing agents other than atmospheric oxygen. The invention also relates to a multi-compartment device and to a composition comprising all of the above-mentioned ingredients.

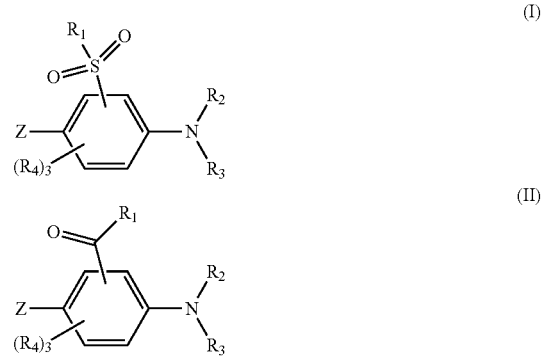

20 Claims, No Drawings

(56) References Cited

U.S. PATENT DOCUMENTS

| | | | |
|---|---|---|---|
| RE30,199 E | 1/1980 | Rose et al. | |
| 4,874,554 A | 10/1989 | Lange et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,766,576 A | 6/1998 | Löwe et al. | |
| 5,938,792 A | 8/1999 | Lang et al. | |
| 6,099,592 A | 8/2000 | Vidal et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,730,789 B1 | 5/2004 | Birault et al. | |
| 2002/0050013 A1 | 5/2002 | Vidal et al. | |
| 2003/0019051 A9 | 1/2003 | Vidal et al. | |
| 2003/0167579 A1 | 9/2003 | Lang | |
| 2007/0044254 A1 | 3/2007 | Ramos-Stanbury et al. | |
| 2010/0247465 A1* | 9/2010 | Simonet | A61K 8/31 424/62 |
| 2010/0278767 A1* | 11/2010 | Hoffkes | A61K 8/33 424/62 |

FOREIGN PATENT DOCUMENTS

| | | | |
|---|---|---|---|
| DE | 4133957 A1 | 4/1993 | |
| DE | 19543988 A1 | 5/1997 | |
| EP | 0345728 | * 12/1989 | A61K 7/13 |
| EP | 0345728 A2 | 12/1989 | |
| EP | 0455168 A1 | 11/1991 | |
| EP | 0770375 A1 | 5/1997 | |
| FR | 1366799 A | 7/1964 | |
| FR | 2733749 A1 | 11/1996 | |
| FR | 2735976 A1 | 1/1997 | |
| FR | 2801308 A1 | 5/2001 | |
| FR | 2805739 A1 | 9/2001 | |
| FR | 2886136 A1 | 12/2006 | |
| FR | 2889846 A1 | 2/2007 | |
| GB | 1026978 A | 4/1966 | |
| GB | 1153196 A | 5/1969 | |
| JP | 02-019576 A | 1/1990 | |
| JP | 05-163124 A | 6/1993 | |
| WO | 94/08969 A1 | 4/1994 | |
| WO | 94/08970 A1 | 4/1994 | |
| WO | 96/15765 A1 | 5/1996 | |

OTHER PUBLICATIONS

English translation of the Patent FR 1366799 (Apr. 6, 2017).*
International Search Report for PCT/EP2014/063081, dated Nov. 13, 2014.
Todd, Charles, et al., "Volatile Silicone Fluids for Cosmetic Formulations," Cosmetics and Toiletries, vol. 91, Jan. 1976, pp. 29-32.
Porter, M.R., "Handbook of Surfactants," published by Blackie & Son (Glasgow and London), 1991, pp. 116-178.
English language abstract for EP 0770375A1 (May 2, 1997).
Machine translated English language abstract for FR 2735976A1 (Jan. 3, 1977).
English language abstract (EP17289500) for FR 2886136A1 (Dec. 1, 2006).
English language abstract for JP 02-019576A (Jan. 23, 1990).
English language abstract for JP 05-163124A (Jun. 29, 1993).

* cited by examiner

PROCESS FOR DYEING IN THE PRESENCE OF OXIDATION BASES COMPRISING AT LEAST ONE SULFONIC, SULFONAMIDE, SULFONE, AMID OR ACID GROUP AND A METAL CATALYST, DEVICE AND READY-TO-USE COMPOSITION

CROSS REFERENCE TO RELATED APPLICATIONS

This is a national stage application of PCT/EP2014/063081, filed internationally on Jun. 20, 2014, which claims priority to French Application Nos. 1355930 and 1355931, which were both filed on Jun. 21, 2013, all of which are incorporated herein by reference in their entireties.

The present invention relates to a process for the oxidation dyeing of keratin fibres, in particular human keratin fibres such as the hair, which uses one or more metal catalysts and a composition (A) comprising at least 10% by weight of one or more fatty substances, one or more oxidation bases comprising at least one sulfonic, sulfonamide or sulfone group, and one or more chemical oxidizing agents other than atmospheric oxygen.

The invention also relates to a multi-compartment device that is suitable for performing the process of the invention, and also to a ready-to-use composition comprising the abovementioned ingredients.

The present invention relates to the field of dyeing keratin fibres and more particularly to the field of hair dyeing using oxidation dyes.

These compounds, also known as oxidation bases, are small, colourless or weakly coloured molecules, which, when combined with oxidizing agents, produce coloured species within the keratin fibre by means of an oxidative condensation reaction. In general, oxidation bases are chosen from ortho- or para-phenylenediamines, ortho- or para-aminophenols and heterocyclic compounds.

The shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds. The variety of molecules used as oxidation bases and couplers allows a wide range of colours to be obtained.

There is, however, an ongoing search for novel tints and shades. Not all the compounds that can potentially be used as oxidation bases for cosmetic applications are used, since the dyeing performance qualities obtained are unsatisfactory. In particular, the colorations obtained are not strong enough, or give heterogeneous colorations, which is obviously prohibitive. It has thus been observed that certain sparingly reactive amino benzenic or heterocyclic oxidation bases fall within this case.

One of the objects of the present invention is to significantly improve the dyeing performance qualities that would be obtained with sparingly reactive oxidation bases relative to the qualities that would be obtained if they were present in standard dye compositions, in particular better build-up. This aim is achieved by the present invention, one subject of which is especially a process for dyeing keratin fibres, in particular human keratin fibres such as the hair, in which use is made of one or more metal catalysts and a composition (A) comprising:
(a) at least 10% by weight of one or more fatty substances,
(b) one or more oxidation bases chosen from
i) compounds of formula (I), the addition salts thereof, solvates thereof and mixtures thereof:

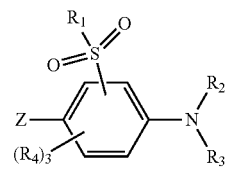

in which:
$R_1$ represents:
a hydroxyl radical,
a $C_1$-$C_{10}$ alkyl radical optionally bearing at least one hydroxyl, $C_1$-$C_4$ alkoxy, —O—$SO_3H$, —$SO_3H$, —COOH or halo group, in particular fluoro,
an amino radical optionally substituted with one or two identical or different groups, chosen from:
$C_1$-$C_{20}$ linear or $C_3$-$C_{20}$ branched or cyclic alkyl, or $C_3$-$C_{20}$ linear or branched alkenyl groups, these alkyl or alkenyl groups optionally bearing at least one hydroxyl or $C_1$-$C_4$ alkoxy radical optionally substituted with a hydroxyl group, or amino optionally substituted with one or two identical or different $C_1$-$C_4$ alkyl groups, or pyridyl or furyl, or combinations thereof; the said alkyl or alkenyl groups possibly forming, together with the nitrogen atom that bears them, a saturated or unsaturated 5- to 7-membered heterocycle optionally comprising one or two identical or different additional endocyclic heteroatoms, chosen from nitrogen, oxygen and sulfur, the said heterocycle being optionally substituted on a carbon or nitrogen atom with at least one $C_1$-$C_4$ alkyl radical; the said heterocycle being optionally fused to a phenyl nucleus;
the groups R'$SO_2$— in which R' represents a $C_1$-$C_4$ alkyl or phenyl radical;
benzyl($C_6H_6$—$CH_2$—), phenyl or naphthyl groups optionally substituted with at least one $C_1$-$C_4$ alkyl group; trifluoromethyl or hydroxyl groups; $C_1$-$C_{20}$ alkoxy groups; amino groups; sulfonic (—$SO_3H$) groups; a halogen atom, in particular chlorine;
a saturated, unsaturated or aromatic 5- or 6-membered heterocycle comprising one to three identical or different endocyclic heteroatoms, chosen in particular from nitrogen and sulfur,
a phenyl or benzyl radical, optionally substituted with at least one radical chosen from $C_1$-$C_6$ alkyl, $C_1$-$C_{20}$ alkoxy, hydroxyl, amino, trifluoromethyl, ($C_1$-$C_4$)alkylamido (alk-CONH—) and sulfonic (—$SO_3H$) groups or a halogen atom, in particular chlorine; $R_2$ and $R_3$, which may be identical or different, represent a hydrogen atom or a $C_1$-$C_4$ alkyl radical,
$R_4$, which may be identical or different, represent a hydrogen atom, a $C_1$-$C_4$ alkyl radical, a $C_1$-$C_4$ alkoxy radical, a carboxylic (—COOH), sulfonic (—$SO_3H$), ($C_1$-$C_4$)alkyl ($C_6$)arylsulfonyl (alk-aryl-$SO_2$—) or sulfonamido (NH$_2$—$SO_2$—) group, or a halogen, more particularly chosen from chlorine and bromine,
two radicals $R_4$ borne by adjacent carbon atoms may form, with the said carbon atoms, a saturated, unsaturated or aromatic 6-membered ring, optionally comprising an endocyclic nitrogen atom, the said ring being optionally fused to another 6-membered aromatic nucleus, the said ring(s) being optionally substituted with a ($C_1$-$C_4$)alkylamido (alk-CONH—) or sulfonic (—$SO_3H$) radical;

Z represents a hydroxyl group or an amino group optionally substituted with one or two identical or different radicals $R_6$, representing:
  a linear $C_1$-$C_{10}$ alkyl or branched $C_3$-$C_{10}$ alkyl radical,
    optionally interrupted with a heteroatom chosen from oxygen, an amino group optionally substituted with a $C_1$-$C_4$ alkyl radical, an ammonium group substituted with three identical or different $C_1$-$C_4$ alkyl radicals;
    the said alkyl radical optionally bearing at least:
      a hydroxyl radical;
      an amino radical optionally substituted with a $C_1$-$C_4$ alkyl group;
      an ammonium radical substituted with three identical or different $C_1$-$C_4$ alkyl groups, one or more of these groups being optionally substituted with a —COOH or hydroxyl group;
      a phenyl optionally bearing a radical —$SO_2$—$R_7$ in which $R_7$ represents a $C_1$-$C_4$ alkyl radical, optionally bearing a hydroxyl radical, or an amino group;
      a group —O—$SO_3H$,
      a group —$SO_3H$,
      a group —COOH,
      a radical —$SO_2$—$R_7$ in which $R_7$ represents a $C_1$-$C_4$ alkyl radical, a phenyl group, optionally bearing a hydroxyl radical, an amino group, an ammonium radical comprising three identical or different radicals, chosen from $C_1$-$C_4$ alkyls optionally bearing a carboxylic group, in acid or salified form;
      a group —NHCO—$R_8$ or —NH—CO—NH—$R_8$, with $R_8$ representing a phenyl group or a $C_1$-$C_4$ alkyl radical, optionally bearing a carboxylic group;
  a benzyl radical, a phenyl radical,
    optionally substituted with at least
      a $C_1$-$C_4$ alkyl radical optionally bearing at least one hydroxyl radical,
      a hydroxyl radical,
      a $C_1$-$C_4$ alkoxy radical,
      a halogen atom, in particular chlorine,
      an amino radical optionally substituted with one or two $C_1$-$C_4$ alkyl groups optionally bearing a hydroxyl,
      a sulfonic group (—$SO_3H$),
      a radical —$SO_2$—$R_9$ in which $R_9$ represents a $C_1$-$C_4$ alkyl radical, optionally bearing a hydroxyl radical, or an amino group,
    two radicals borne by adjacent carbon atoms may form, together with the said carbon atoms, a 6-membered heterocycle; the said heterocycle comprising one or two endocyclic oxygen atoms;
  two alkyl radicals $R_6$ may form, with the nitrogen atom that bears them, a saturated or unsaturated 5- to 7-membered heterocycle, optionally comprising another endocyclic group, with a heteroatom, in particular of the type such as —O—, —S— or —$NR_{10}$, $R_{10}$ representing a hydrogen atom or a $C_1$-$C_4$ alkyl radical optionally substituted with a hydroxyl group;
    the said heterocycle being optionally fused with a phenyl nucleus;
    the said heterocycle being optionally substituted on one of its carbon atoms with a $C_1$-$C_4$ alkyl radical optionally bearing a hydroxyl radical, with an amino radical optionally substituted with one or two identical or different radicals $R_{11}$, chosen from a $C_1$-$C_4$ alkyl radical optionally bearing a hydroxyl radical, an amino radical optionally substituted with one or two identical or different $C_1$-$C_4$ alkyl radicals; two of the radicals $R_{11}$ may form a 5- to 6-membered heterocycle optionally comprising another endocyclic heteroatom, in particular of the type such as —O—, —S— or —$NR_{12}$, $R_{12}$ representing a hydrogen atom or a $C_1$-$C_4$ alkyl radical;
a radical

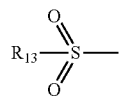

in which $R_{13}$ represents a $C_1$-$C_4$ alkyl radical or a phenyl radical;
  if $R_1$ represents a hydroxyl radical, then at least one of the groups $R_4$ or $R_6$ is other than hydrogen; and
  ii) compounds of formula (II), addition salts thereof, solvates thereof, mixtures thereof:

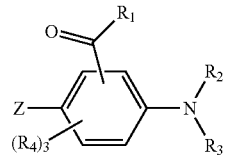

in which:
Z represents a hydroxyl group or an amino group optionally substituted with one or two $C_1$-$C_4$ alkyl radicals, which may be identical or different;
$R_1$ represents:
  a hydroxyl radical,
  an amino radical —$NR_{11}R_{12}$, in which $R_{11}$ and $R_{12}$, which may be identical or different, represent:
    a hydrogen atom;
    a $C_1$-$C_{20}$ alkyl radical, optionally bearing at least:
      one of the following groups: hydroxyl, $C_1$-$C_{15}$ alkoxy, phenoxy,
      —COOH, —$SO_3H$;
      cyano;
      ($C_1$-$C_4$)alkylcarbonyl amino (or ($C_2$-$C_4$)acylamino), mono- or di-($C_1$-$C_4$)alkylaminocarbonyl;
      amino, optionally substituted with one or two $C_1$-$C_4$ alkyl radicals, which may be identical or different;
      a saturated or unsaturated, aromatic or non-aromatic heterocycle having from 5 to 7 ring members, optionally containing from 1 to 3 endocyclic heteroatoms chosen from nitrogen, oxygen and sulfur, the nitrogen optionally bearing a hydrogen or a $C_1$-$C_4$ alkyl;
    a $C_6$-$C_{10}$ aryl radical comprising an aromatic nucleus, or two fused aromatic nuclei, the aryl radical being optionally substituted with one or more $C_1$-$C_4$ alkyl, hydroxyle, $C_1$-$C_4$ alkoxy or trifluoromethyl radicals,
    a $C_6$-$C_{10}$ aryl radical comprising an aromatic nucleus optionally fused to another (hetero)aromatic nucleus, the heteroatom being nitrogen, the aryl radical being optionally substituted with at least one of the following groups: $C_1$-$C_4$ alkyl, hydroxyl, $C_1$-$C_4$ alkoxy, cyano, trifluoromethyl, halogen, in particular chlorine, $(C_1-C_4)$alkylcarbonylamino, amino; aminosulfonyl; $C_2-C_4$ alkynyl; $NH_2-C(=NH_2)-$;

a saturated or unsaturated, aromatic or non-aromatic heterocycle having from 5 to 6 ring members, comprising from one to four heteroatoms, more particularly chosen from nitrogen and oxygen, it being possible for the $R_{11}$ and $R_{12}$ radicals to form, together with the nitrogen atom to which they are attached, a heterocycle having from 5 to 7 ring members, optionally fused to a $C_6$ aromatic nucleus, which is cationic or non-cationic, saturated or unsaturated, and aromatic or non-aromatic, optionally containing 1 endocyclic additional heteroatom chosen from nitrogen, oxygen and sulphur; the nitrogen optionally bearing one or two $C_1-C_4$ alkyls, which may be identical or different, the alkyl group(s) optionally bearing an —$SO_3H$ group; it being possible for the heterocycle to be substituted on at least one of its carbon atoms with one or two groups, which may be identical or different, chosen from a $C_1-C_4$ alkyl radical optionally bearing a hydroxyl radical; a hydroxyl radical; an aminocarbonyl radical and a mono- or di-$(C_1-C_4)$ alkylaminocarbonyl radical;

$R_2$ and $R_3$, which may be identical or different, represent:

a hydrogen atom;

a linear $C_1-C_{10}$, branched $C_3-C_{10}$, or cyclic $C_5-C_{10}$ alkyl radical; the alkyl radical being optionally substituted with at least one of the following groups: $(C_1-C_4)$ alkylthio (RS—), cyano, hydroxyl, $C_1-C_4$ alkoxy; amino optionally substituted with one or two $C_1-C_4$ alkyl radicals, which may be identical or different, a mono- or di- $(C_1-C_4)$alkylaminocarbonyl radical; a saturated, unsaturated or aromatic heterocycle having from 5 to 7 ring members, comprising at least one endocyclic heteroatom chosen from nitrogen, oxygen and sulfur, the nitrogen atom optionally bearing a $C_1-C_4$ alkyl radical;

a saturated or unsaturated, aromatic or non-aromatic $C_5-C_{10}$ heterocyclic radical comprising at least one heteroatom such as nitrogen, the nitrogen atom optionally bearing a hydrogen or a $C_1-C_4$ alkyl radical;

a $C_6-C_{10}$ (hetero)aryl radical optionally comprising at least one endocyclic heteroatom, such as nitrogen; said radical being optionally substituted with one or two $C_1-C_4$ alkyl radicals, with one or two $C_1-C_4$ alkoxy(s), or with one or two amino(s) optionally substituted with one or two $C_1-C_4$ alkyl groups, which may be identical or different; two substituents borne by adjacent carbon atoms of the (hetero)aryl radical may form an aromatic or non-aromatic, fused ring or heterocycle comprising from 5 to 6 ring members, optionally comprising one or two endocyclic heteroatoms such as oxygen or nitrogen;

two radicals $R_2$ and $R_3$, preferably alkyl, can form, together with the nitrogen atom to which they are connected, a saturated or unsaturated, aromatic or non-aromatic heterocycle having from 5 to 7 ring members, optionally containing from 1 to 4 endocyclic additional heteroatoms, which may be identical or different, chosen from nitrogen, oxygen or sulfur, or else containing a carbonyl group; the nitrogen optionally bearing one or two $C_1-C_4$ alkyl(s), which may be identical or different; it being possible, where appropriate, for said heterocycle to be fused to an aromatic nucleus, preferably a $C_6$ aromatic nucleus, or else to be fused to a saturated $C_5-C_7$, preferably $C_6$, ring, it being possible for said heterocycle to be substituted, on one of the carbon atoms, with one or two of the following radicals, which may be identical or different: $C_1-C_4$ alkyl optionally bearing a hydroxyl, $C_1-C_4$ alkoxy; hydroxyl; amino optionally substituted with one or two radicals which may be identical or different; aminocarbonyl; mono- or di-$(C_1-C_4)$alkylaminocarbonyl;

$R_4$, which may be identical or different, represent:

a hydrogen atom;

a $C_1-C_{20}$ alkyl or $C_2-C_6$ alkenyl; said alkyl or alkenyl being optionally substituted with at least one amino group which is unsubstituted or substituted with one or two $C_1-C_4$ alkyl groups, which may be identical or different; hydroxyl; $C_1-C_4$ alkoxy; cyano; —COOH; $(C_1-C_4)$alkylcarbonyl; trifluoromethyl; a saturated or unsaturated (hetero)cycle having from 5 to 7 ring members, optionally comprising one or two heteroatoms such as, for example, nitrogen or oxygen; it being possible for the nitrogen to optionally bear a $C_1-C_4$ alkyl group;

a saturated or unsaturated (hetero)cycle having 5 to 7 ring members, optionally comprising one or two heteroatoms such as, for example, nitrogen or oxygen; it being possible for the nitrogen to optionally bear a hydrogen atom or a $C_1-C_4$ alkyl group; it being possible for said (hetero)cycle to comprise an endocyclic carbonyl group, it being possible for said heterocycle to optionally be substituted with a hydroxyl group;

—COOH; —$SO_3H$;

halogens, such as, for example, chlorine, fluorine or bromine;

hydroxyl, $C_1-C_4$ alkoxy optionally bearing a carboxylic group, $(C_1-C_4)$alkylthio;

$(C_1-C_4)$alkylcarbonyl (or $C_2-C_4$ acyl); $(C_1-C_4)$alkylcarbonyl amino (or $(C_2-C_4)$acylamino); mono- or di-$(C_1-C_4)$ alkylaminocarbonyl; aminocarbonyl;

trifluoromethyl;

aryl$(C_1-C_4)$alkyl;

two $R_4$ radicals borne by adjacent carbon atoms can form an aromatic or non-aromatic, fused (hetero)cycle having from 5 to 6 ring members; it being possible for said heterocycle to comprise at least one heteroatom, preferably from 1 to 2 heteroatoms, chosen from nitrogen, sulfur and oxygen, it being possible for the nitrogen atom to bear a $C_1-C_4$ alkyl radical; it being possible for said ring or heterocycle to be substituted, on at least one of the carbon atoms, with a $C_1-C_4$ alkyl radical;

it being understood that, if Z and $R_1$ denote a hydroxyl group, then at most two $R_4$ denote a hydrogen atom, and mixtures thereof, and (c) one or more chemical oxidizing agents other than atmospheric oxygen.

In the process of the invention, the metal catalyst(s) may constitute or form part of a composition (B) which is mixed with composition (A) before applying the mixture to keratin fibres or which is applied separately as a pre-treatment or post-treatment with or without intermediate rinsing.

The present invention also relates to a multi-compartment device comprising a first compartment containing a cosmetic composition (B) comprising one or more metal catalysts as defined previously, a second compartment containing a cosmetic composition (A1) comprising one or more oxidation bases of formula (I) as defined previously, and a third compartment containing a composition (A2) comprising one or more chemical oxidizing agents other than atmospheric oxygen, and, where appropriate, a fourth compartment containing a composition (A3) comprising at least one fatty substance as defined previously; compositions (A1) and/or (A2) possibly comprising at least one fatty substance; such that composition (A) resulting from the mixing of compositions (A1), (A2) and, where appropriate, (A3) is greater than or equal to 10% relative to the total weight of composition (A).

Another subject of the invention consists of a composition comprising:
(a) at least 10% by weight of one or more fatty substances,
(b) one or more oxidation bases of formula (I) and/or (II) as described previously,
(c) one or more chemical oxidizing agents other than atmospheric oxygen,
(d) at least one metal catalyst.

Thus, the use of the process according to the invention leads to strong colorations, or alternatively to better build-up of dye in the fibre. The colorations obtained are sparingly selective.

Furthermore, the colorations obtained remain stable, in particular with respect to light and shampooing.

Other characteristics and advantages of the invention will emerge more clearly on reading the description and the examples that follow.

In the text hereinbelow, and unless otherwise indicated, the limits of a range of values are included within that range.

The human keratin fibres treated via the process according to the invention are preferably the hair.

The expression "at least one" is equivalent to the expression "one or more".

In general, the term "addition salts of compounds" means the addition salts of these compounds with a mineral acid such as hydrochloric acid, hydrobromic acid, sulfuric acid or phosphoric acid, with an organic acid such as citric acid, succinic acid, tartaric acid, lactic acid, para-toluenesulfonic acid, benzenesulfonic acid, dodecylbenzenesulfonic acid or acetic acid, preferably hydrochloric acid, citric acid, succinic acid, tartaric acid, phosphoric acid or lactic acid, or with a base which may be chosen from alkali metal or alkaline-earth metal hydroxides or carbonates (in particular for the sodium or potassium salts), ammonia (for the ammonium salts), organic amines and in particular alkanolamines such as triethanolamine or monoethanolamine.

The solvates of compounds more particularly represent the hydrates of such compounds and/or the combination of such compounds with a linear or branched $C_1$-$C_4$ alcohol such as methanol, ethanol, isopropanol or n-propanol. Preferably, the solvates are hydrates.

Metal Catalysts

As indicated previously, the process is performed in the presence of at least one metal catalyst.

Metal catalysts are compounds that comprise one or more metals in their structure.

The metals are chosen from transition metals and rare-earth metals, and alloys thereof.

In particular, the metals are chosen from transition metals and rare-earth metals.

Among the transition metals, mention may be made especially of manganese, iron, cobalt, copper, zinc, platinum, nickel, titanium, silver, zirconium, chromium, molybdenum, tungsten, platinum, gold and vanadium, and among these most particularly manganese.

Among the rare-earth metals, mention may be made especially of cerium.

Thus, the metal catalysts are especially catalysts based on transition metals or on rare-earth metals, and more particularly manganese-based, vanadium-based or cerium-based catalysts.

The metal catalysts used may be chosen from metal salts, metal oxides and metal complexes, and mixtures thereof.

For the purposes of the present invention, the term "metal complexes" means systems in which the metal ion, i.e. the central atom, is bonded to one or more electron donors, called ligands, via chemical bonds. Examples that may be mentioned include porphyrins and phthalocyanines, which are especially cationic.

Preferably, the metal catalysts used in the dyeing process are chosen from metal salts.

For the purposes of the present invention, the term "metal salts" means the salts derived from the action of an acid on a metal.

Preferentially, the metal catalysts used in the dyeing process are chosen from transition metal salts, such as manganese salts, and rare-earth metal salts, such as cerium salts, and also mixtures thereof.

The metal salts may be mineral or organic salts.

According to one variant, the metal salts are mineral and may be chosen from halides, carbonates, sulfates and phosphates, in particular optionally hydrated halides.

According to another preferred variant, the metal salts are in oxidation state II and have two (poly)hydroxy acid-derived ligands.

The term "(poly)hydroxy acid" means any carboxylic acid which comprises a hydrocarbon-based chain which is linear or branched, and saturated or unsaturated, preferably saturated and/or linear, comprising from 1 to 10 carbon atoms and from 1 to 9 hydroxyl groups, and comprising from 1 to 4 carboxylic groups —C(O)—OH, at least one of the said —C(O)—OH functions of which is in the carboxylate form —C(O)—O$^-$ complexed with the metal atom, preferably Mn(II). More particularly, the metal salt is complexed with two carboxylate groups such as that of formula (I):

$$R-C(O)-O-M-O-C(O)-R' \qquad (I)$$

and also the solvates thereof, such as the hydrates, and the enantiomers thereof, in which formula (I):
M represents a metal (II) or metal$^{2+}$ in oxidation state II,
R and R', which may be identical or different, represent a ($C_1$-$C_6$)(poly)hydroxyalkyl group. The metal catalysts are particularly chosen from organic acid salts of transition metals, in particular of manganese, and mineral salts of rare-earth metals, especially of cerium.

According to one particular embodiment of the invention, the manganese is not a manganese oxide, but a manganese salt.

The organic metal salts may be more particularly chosen from organic acid salts such as citrates, lactates, glycolates, gluconates, acetates, propionates, fumarates, oxalates and tartrates, especially gluconates.

More preferentially, the metal catalysts are chosen from manganese gluconate and cerium chloride heptahydrate, in particular manganese gluconate.

Preferably, the metal catalyst(s) are chosen from the compounds of formula (I) and more particularly represent(s) manganese gluconate.

The metal catalyst(s) may constitute all or part of a composition (B). This composition (B) may be anhydrous or aqueous.

The metal catalyst(s) may be present in composition A.

The metal catalyst(s) may be present in a content ranging from 0.001% to 10% by weight, preferably in a content ranging from 0.001% to 1% by weight and better still ranging from 0.01% to 0.5% by weight relative to the total weight of the composition applied to the keratin fibres containing them.

Oxidation Bases of Formula (I) and (II)

Bases of Formula (I)

As indicated previously, the process according to the invention uses a composition that may comprise at least one oxidation base of formula (I) as defined above.

In accordance with a first embodiment of the invention, the oxidation base(s) are chosen from the compounds of formula (I) in which:

$R_1$ represents:
 a hydroxyl radical, $R_2$ and $R_3$, which may be identical or different, represent a hydrogen atom or a $C_1$-$C_4$ alkyl radical, $R_4$, which may be identical or different, represent a hydrogen atom, a $C_1$-$C_4$ alkyl radical, a $C_1$-$C_4$ alkoxy radical, a carboxylic or sulfonic (—$SO_3H$) group, or a halogen, more particularly chosen from chlorine and bromine, two radicals $R_4$ borne by adjacent carbon atoms may form, with the said carbon atoms, a saturated, unsaturated or aromatic 6-membered ring, optionally comprising an endocyclic nitrogen atom, the said ring being optionally fused to another 6-membered aromatic nucleus, the said ring(s) being optionally substituted with sulfonic (—$SO_3H$);

Z represents a hydroxyl group or an amino group optionally substituted with one or two identical or different radicals $R_6$, representing:
 a linear $C_1$-$C_{10}$ alkyl or branched $C_3$-$C_{10}$ alkyl radical, optionally interrupted with a heteroatom chosen from oxygen, an amino group optionally substituted with a $C_1$-$C_4$ alkyl radical;
  the said alkyl radical optionally bearing at least:
   a hydroxyl radical,
   an amino radical optionally substituted with a $C_1$-$C_4$ alkyl group,
 two alkyl radicals $R_6$ may form, with the nitrogen atom that bears them, a saturated or unsaturated 5- to 7-membered heterocycle, optionally comprising another endocyclic heteroatom, in particular of the type such as —O—, —S— or —$NR_{10}$, $R_{10}$ representing a hydrogen atom or a $C_1$-$C_4$ alkyl radical.

In accordance with a second embodiment of the invention, the oxidation base(s) are chosen from the compounds of formula (I) in which:

$R_1$ represents:
 an amino radical optionally substituted with one or two identical or different groups, chosen from:
  $C_1$-$C_{20}$ linear or $C_3$-$C_{20}$ branched or cyclic alkyl, or $C_3$-$C_{20}$ linear or branched alkenyl groups, these alkyl or alkenyl groups optionally bearing at least one hydroxyl or $C_1$-$C_4$ alkoxy radical optionally substituted with a hydroxyl group, or amino optionally substituted with one or two identical or different $C_1$-$C_4$ alkyl groups, or pyridyl or furyl, or combinations thereof; the said alkyl or alkenyl groups possibly forming, together with the nitrogen atom that bears them, a saturated or unsaturated 5- to 7-membered heterocycle optionally comprising one or two identical or different additional endocyclic heteroatoms, chosen from nitrogen, oxygen and sulfur, the said heterocycle being optionally substituted on a carbon or nitrogen atom with at least one $C_1$-$C_4$ alkyl radical; the said heterocycle being optionally fused to a phenyl nucleus;
  groups $R'SO_2$— in which $R'$ represents a $C_1$-$C_4$ alkyl or phenyl radical;
  benzyl($C_6H_6$—$CH_2$—), phenyl or naphthyl groups optionally substituted with at least one $C_1$-$C_4$ alkyl group; trifluoromethyl or hydroxyl groups; $C_1$-$C_{20}$ alkoxy groups; amino groups; sulfonic (—$SO_3H$) groups; a halogen atom, in particular chlorine;
  a saturated, unsaturated or aromatic 5- or 6-membered heterocycle comprising one to three identical or different endocyclic heteroatoms, chosen in particular from nitrogen and sulfur, $R_2$ and $R_3$, which may be identical or different, represent a hydrogen atom or a $C_1$-$C_4$ alkyl radical, $R_4$, which may be identical or different, represent a hydrogen atom or a sulfonamido ($NH_2$—$SO_2$—), Z represents a hydroxyl group or an amino group optionally substituted with one or two identical or different radicals $R_6$, representing:
 a linear $C_1$-$C_{10}$ alkyl or branched $C_3$-$C_{10}$ alkyl radical,
  the said alkyl radical optionally bearing at least:
   a hydroxyl radical,
   an amino radical optionally substituted with a $C_1$-$C_4$ alkyl group,
   a group —$SO_3H$,
   a radical —$SO_2$—$R_7$ in which $R_7$ represents a $C_1$-$C_4$ alkyl radical, or a phenyl radical,
 a benzyl radical, a phenyl radical,
  optionally substituted with at least
   a $C_1$-$C_4$ alkyl radical, optionally bearing at least one hydroxyl radical,
   a hydroxyl radical,
   a $C_1$-$C_4$ alkoxy radical,
   a halogen atom, in particular chlorine,
  two radicals borne by adjacent carbon atoms may form, together with the said carbon atoms, a 6-membered heterocycle; the said heterocycle comprising one or two endocyclic oxygen atoms;
 two alkyl radicals $R_6$ may form, with the nitrogen atom that bears them, a saturated or unsaturated 5- to 7-membered heterocycle, optionally comprising another endocyclic group with a heteroatom, in particular of the type such as —O— or —$NR_{10}$, $R_{10}$ representing a hydrogen atom or a $C_1$-$C_4$ alkyl radical optionally substituted with a hydroxyl group;
  the said heterocycle being optionally fused with a phenyl nucleus;
  the said heterocycle being optionally substituted on one of its carbon atoms with a $C_1$-$C_4$ alkyl radical,
 a radical

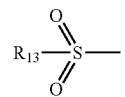

in which $R_{13}$ represents a $C_1$-$C_4$ alkyl radical or a phenyl radical.

According to a third embodiment of the invention, the oxidation base(s) are chosen from the compounds of formula (I) in which:

$R_1$ represents:
 a $C_1$-$C_{10}$ alkyl radical optionally bearing at least one hydroxyl, $C_1$-$C_4$ alkoxy, —O—$SO_3H$, —$SO_3H$, —COOH or halo group, in particular fluoro,
 a phenyl or benzyl radical, optionally substituted with at least one radical chosen from $C_1$-$C_6$ alkyl, $C_1$-$C_{20}$ alkoxy, hydroxyl, amino, trifluoromethyl, ($C_1$-$C_4$)alkylamido (alk-CONH—) and sulfonic (—$SO_3H$) groups or a halogen atom, in particular chlorine;

$R_2$ and $R_3$, which may be identical or different, represent a hydrogen atom or a $C_1$-$C_4$ alkyl radical, $R_4$, which may be identical or different, represent a hydrogen atom, a $C_1$-$C_4$ alkyl radical, a $C_1$-$C_4$ alkoxy radical, or a halogen, more particularly chosen from chlorine and bromine, Z represents a hydroxyl group or an amino group optionally substituted with one or two identical or different radicals $R_6$, representing:

- a linear $C_1$-$C_{10}$ alkyl or branched $C_3$-$C_{10}$ alkyl radical,
  - optionally interrupted with a heteroatom chosen from oxygen, an amino group optionally substituted with a $C_1$-$C_4$ alkyl radical, an ammonium group substituted with three identical or different alkyl radicals;
  - the said alkyl radical optionally bearing at least:
    - a hydroxyl radical,
    - an amino radical optionally substituted with a $C_1$-$C_4$ alkyl group,
    - an ammonium radical substituted with three identical or different $C_1$-$C_4$ alkyl groups, one or more of these groups being optionally substituted with a —COOH or hydroxyl group;
    - a group —O—$SO_3H$,
    - a group —$SO_3H$,
    - a group —COOH,
    - a radical —$SO_2$—$R_7$ in which $R_7$ represents a $C_1$-$C_4$ alkyl radical, optionally bearing a hydroxyl radical, an amino group, an ammonium radical comprising three identical or different radicals, chosen from $C_1$-$C_4$ alkyls optionally bearing a hydroxyl or carboxylic group, in acid or salified form;
    - a group —NHCO—$R_8$ or —NH—CO—NH—$R_8$, with $R_8$ representing a phenyl group or a $C_1$-$C_4$ alkyl radical, optionally bearing a carboxylic group;
- a benzyl radical, a phenyl radical,
  - optionally substituted with at least
    - a hydroxyl radical,
    - a $C_1$-$C_4$ alkoxy radical,
    - an amino radical optionally substituted with one or two $C_1$-$C_4$ alkyl groups optionally bearing a hydroxyl,
    - a sulfonic group (—$SO_3H$),
    - a radical —$SO_2$—$R_9$ in which $R_9$ represents a $C_1$-$C_4$ alkyl radical, optionally bearing a hydroxyl radical, or an amino group,
- two alkyl radicals $R_6$ may form, with the nitrogen atom that bears them, a saturated or unsaturated 5- to 7-membered heterocycle, optionally comprising another endocyclic group with a heteroatom, in particular of the type such as —O— or —$NR_{10}$, $R_{10}$ representing a hydrogen atom or a $C_1$-$C_4$ alkyl radical;
  - the said heterocycle being optionally substituted on one of its carbon atoms with a $C_1$-$C_4$ alkyl radical optionally bearing a hydroxyl radical, with an amino radical optionally substituted with one or two identical or different radicals $R_{11}$, chosen from a $C_1$-$C_4$ alkyl radical; two radicals $R_{11}$ may form a 5- to 6-membered heterocycle optionally comprising another endocyclic heteroatom, in particular of the type such as —O—, —S— or —$NR_{12}$, $R_{12}$ representing a hydrogen atom or a $C_1$-$C_4$ alkyl radical;

a radical

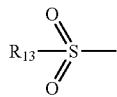

in which $R_{13}$ represents a $C_1$-$C_4$ alkyl radical.

For each of these embodiments, $R_2$ and $R_3$ preferably represent a hydrogen atom.

Among the oxidation bases of formula (I) that are suitable for use in the invention, mention may be made of the following compounds, addition salts thereof, solvates thereof, and mixtures thereof:

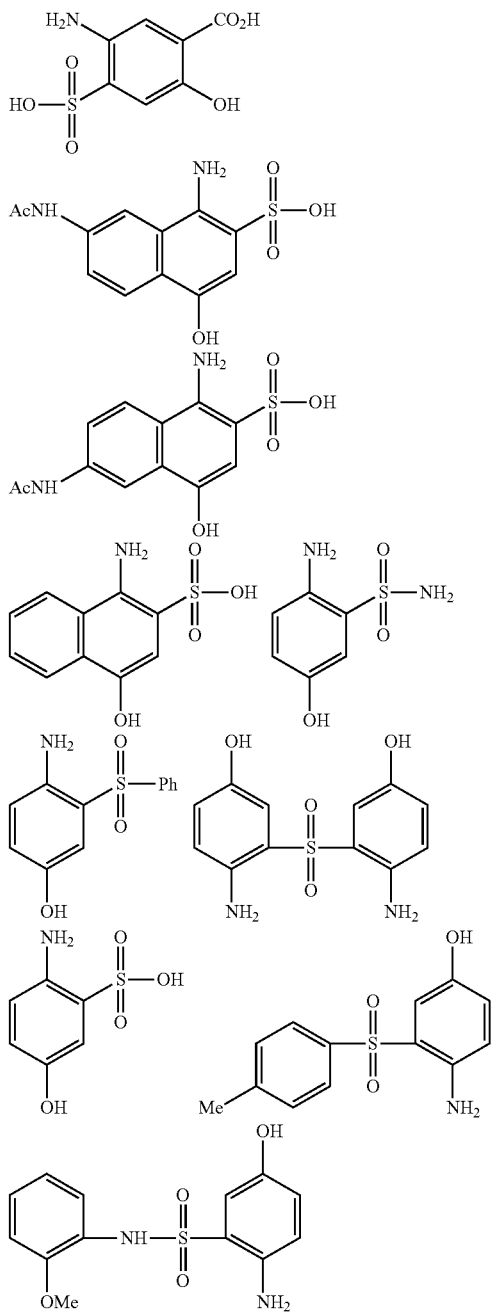

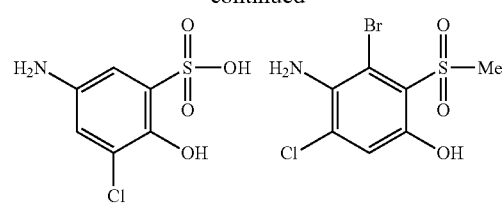
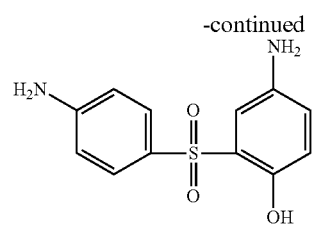
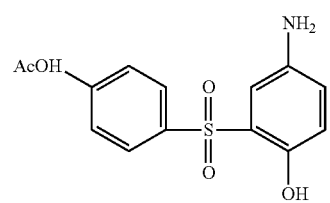
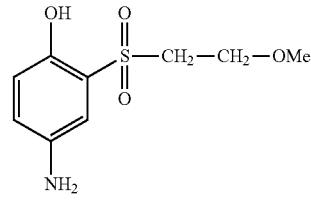
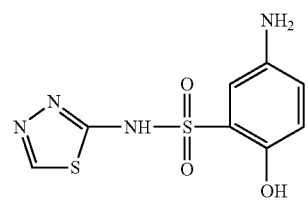
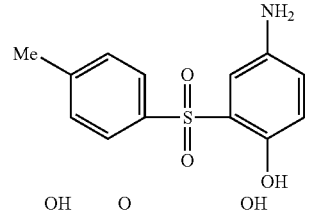
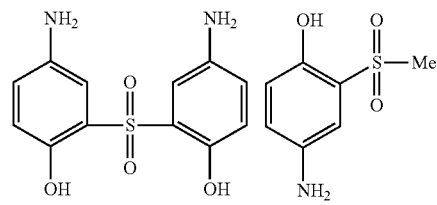
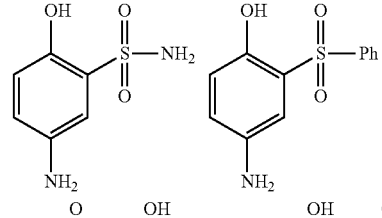
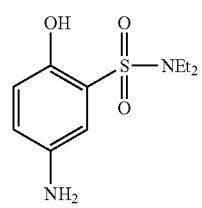
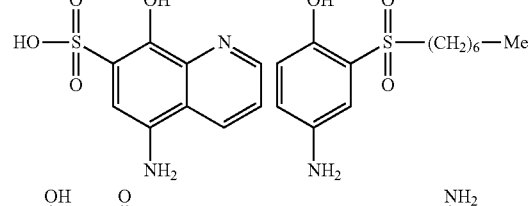
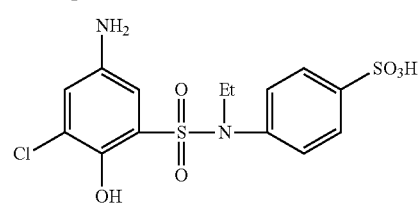
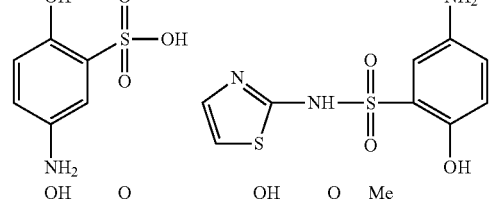
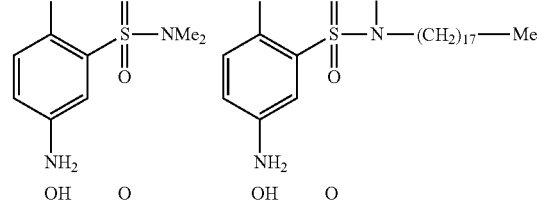
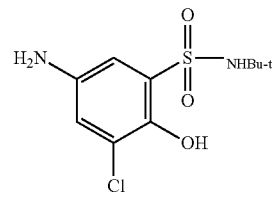
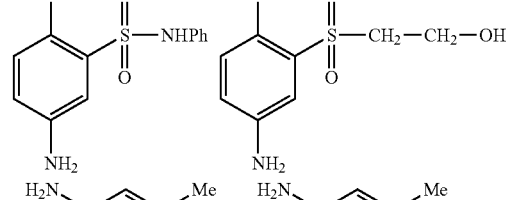
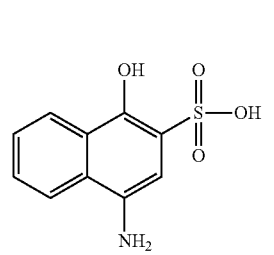
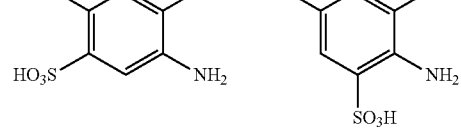

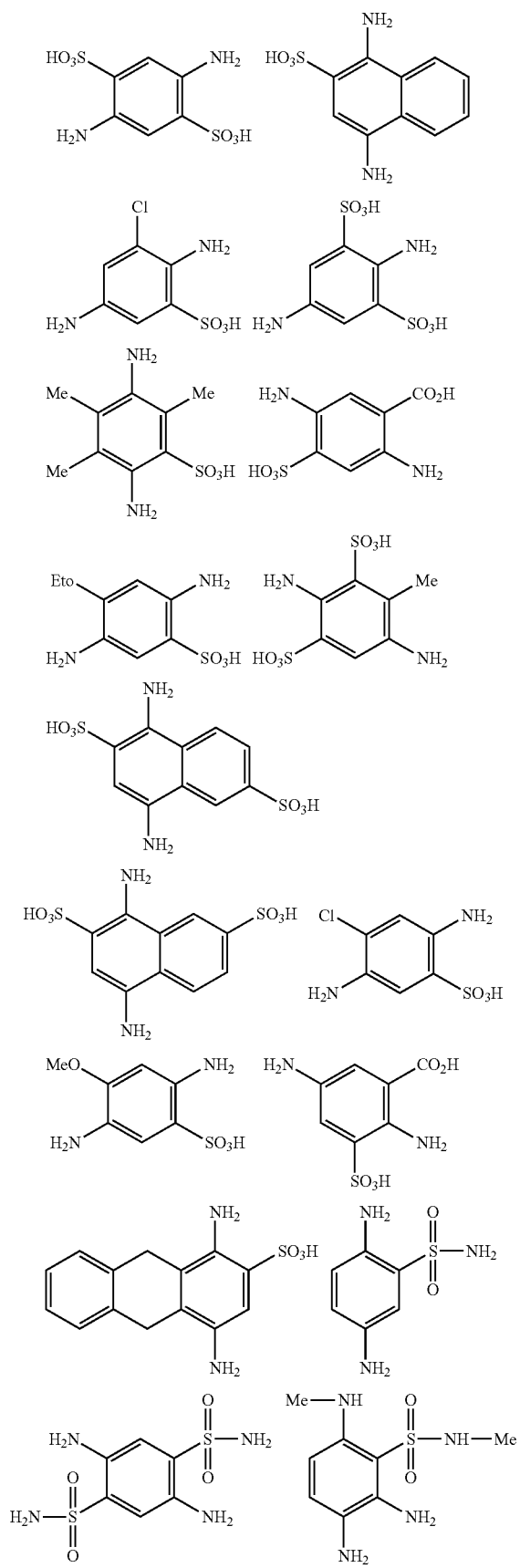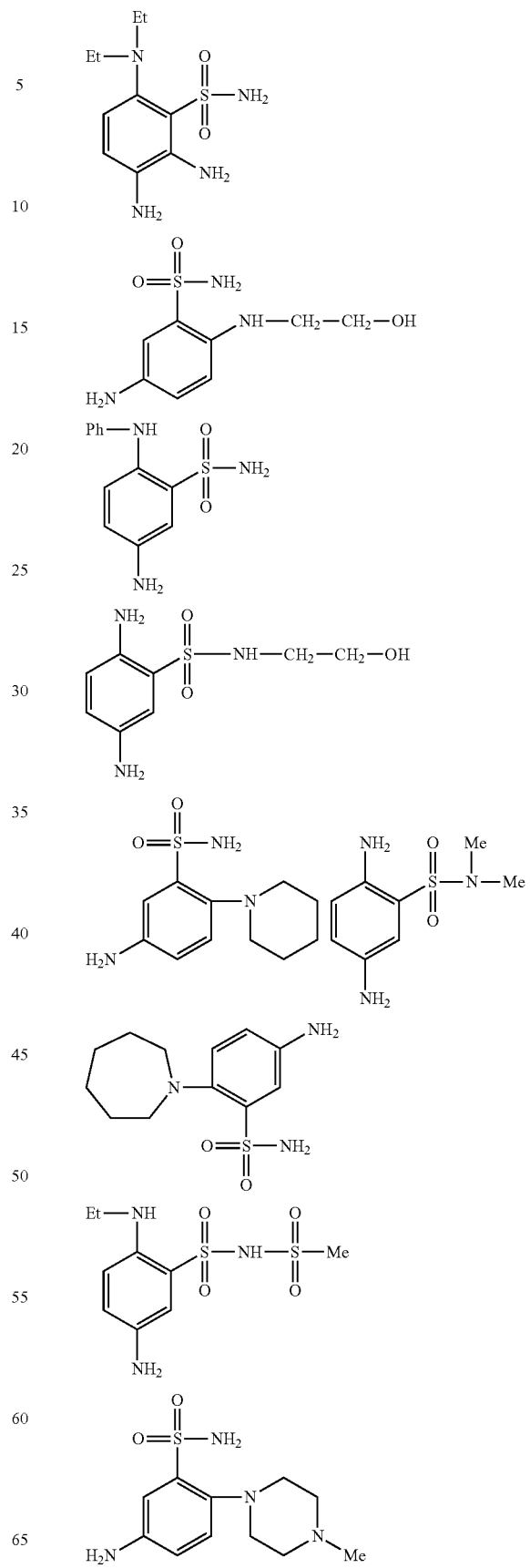

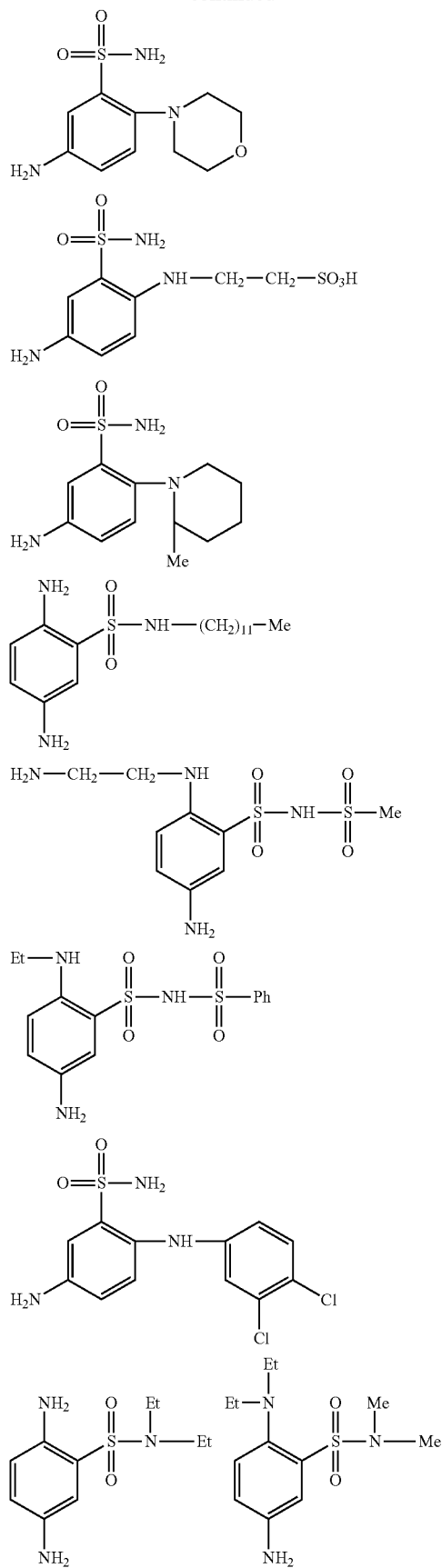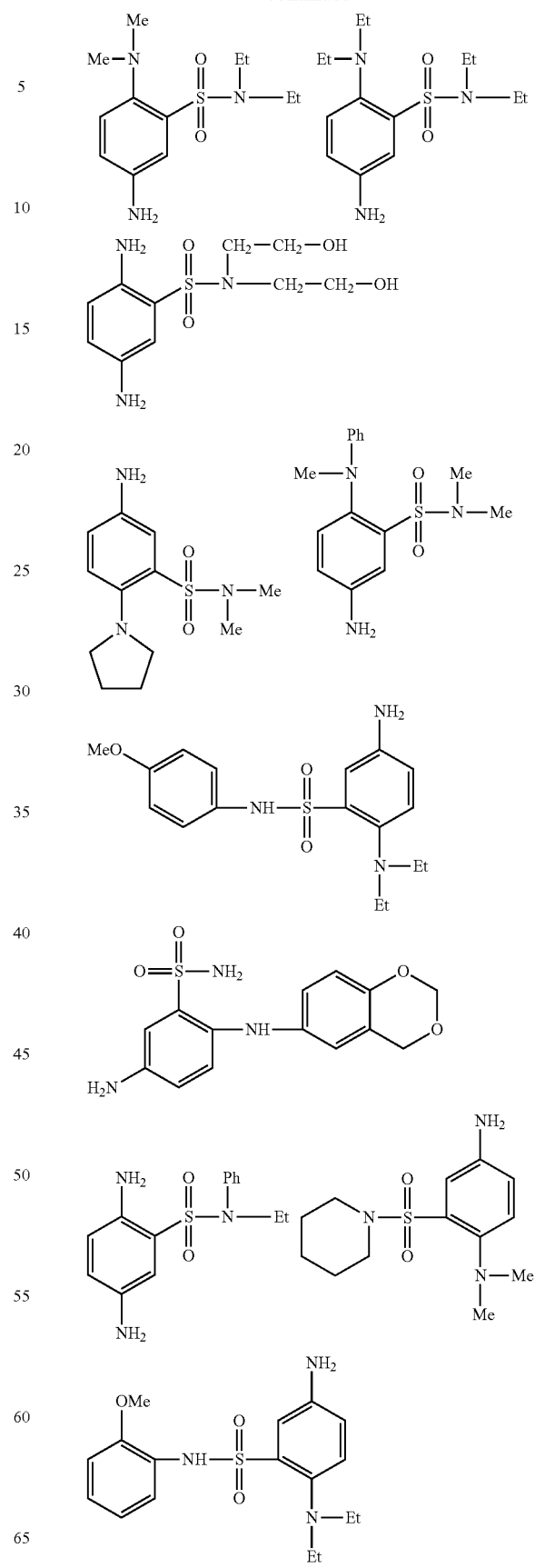

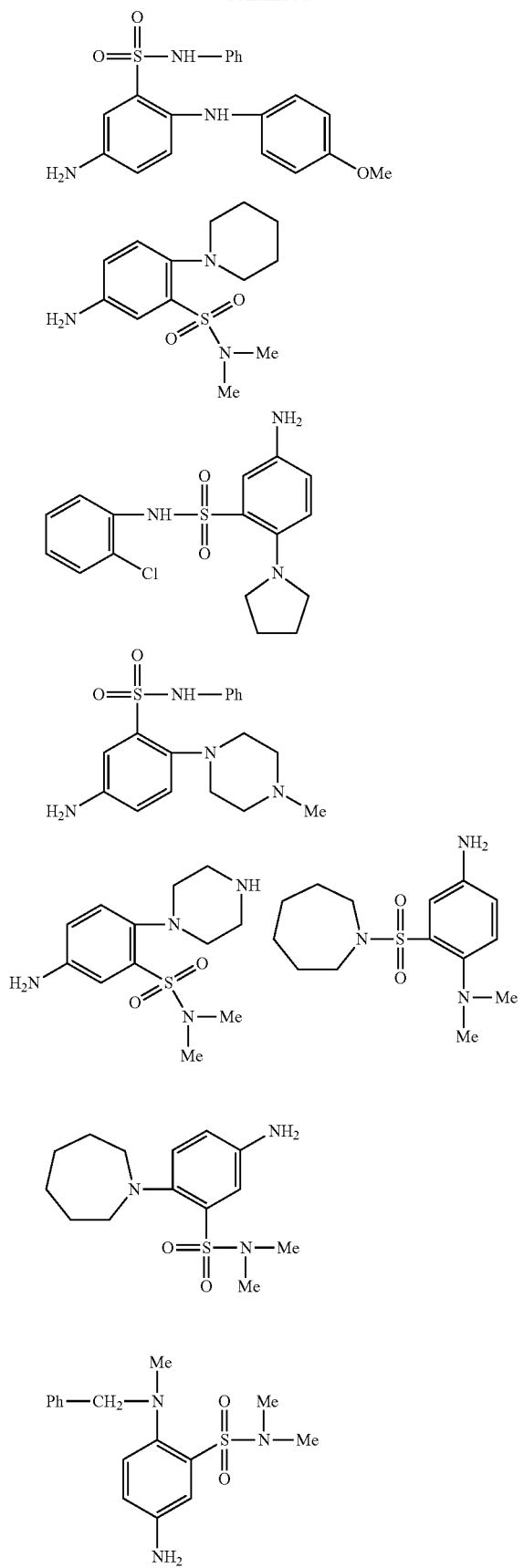

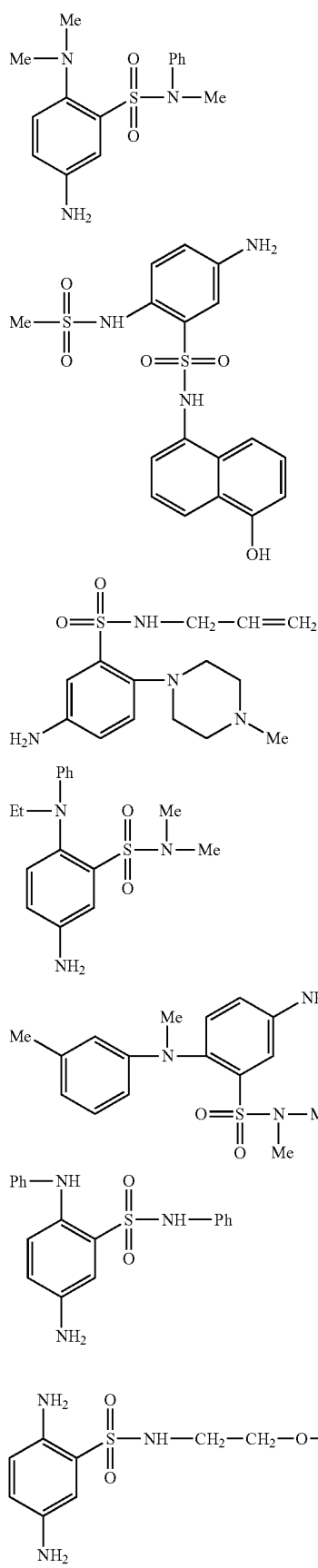
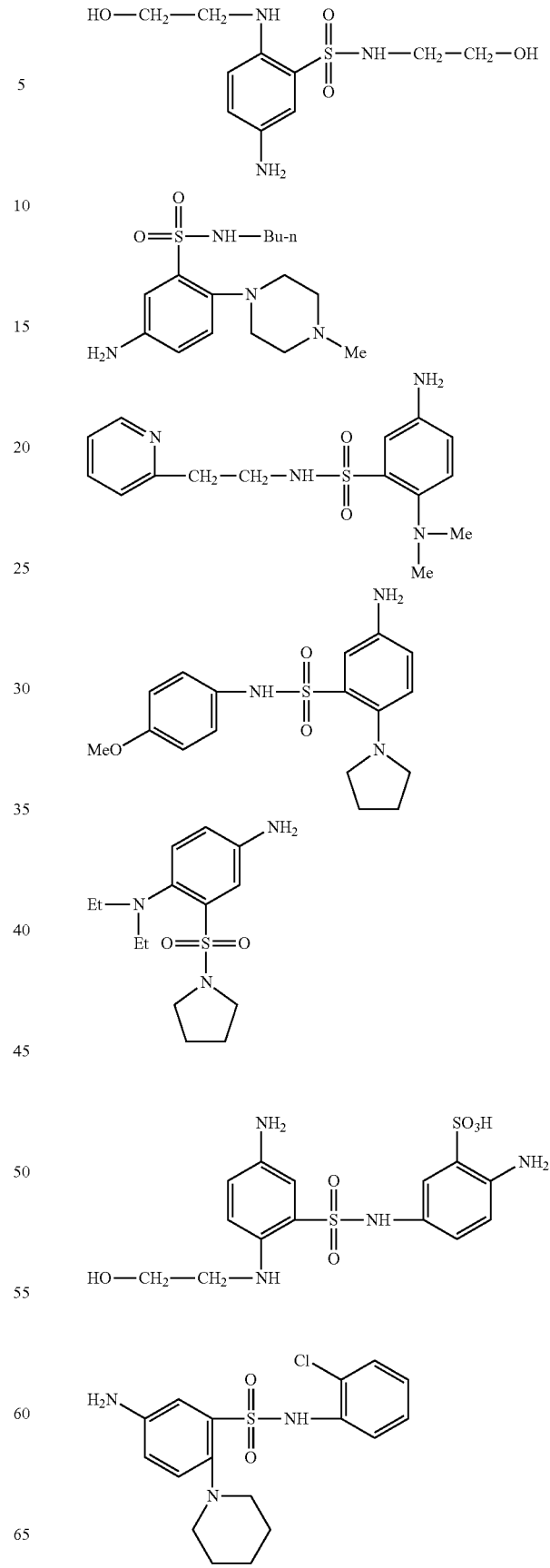

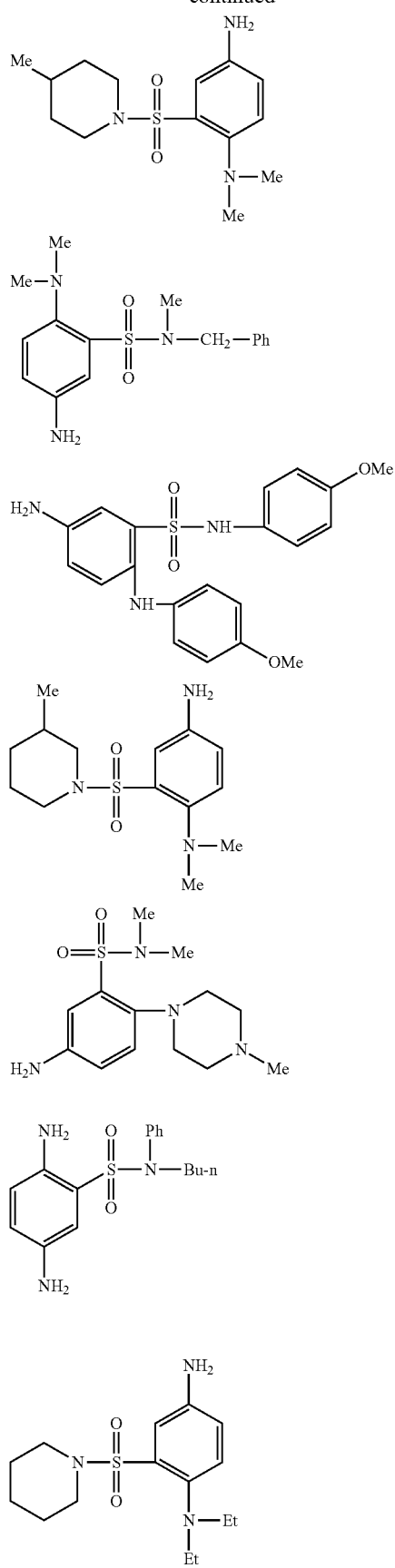
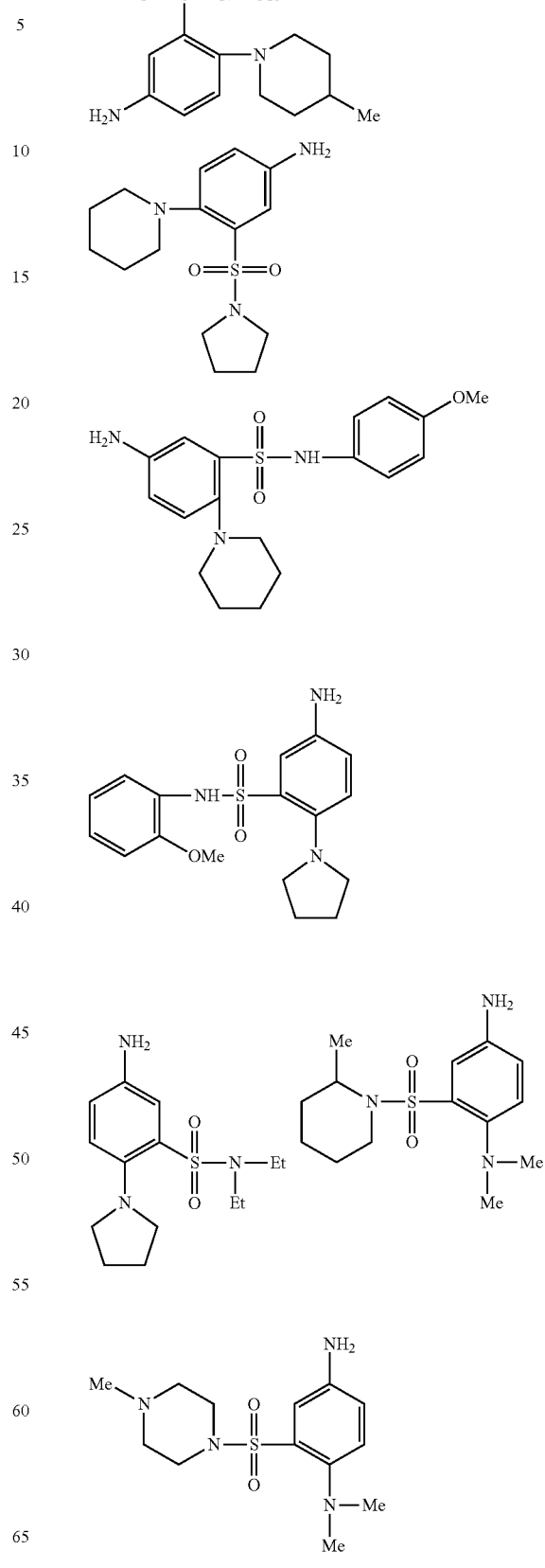

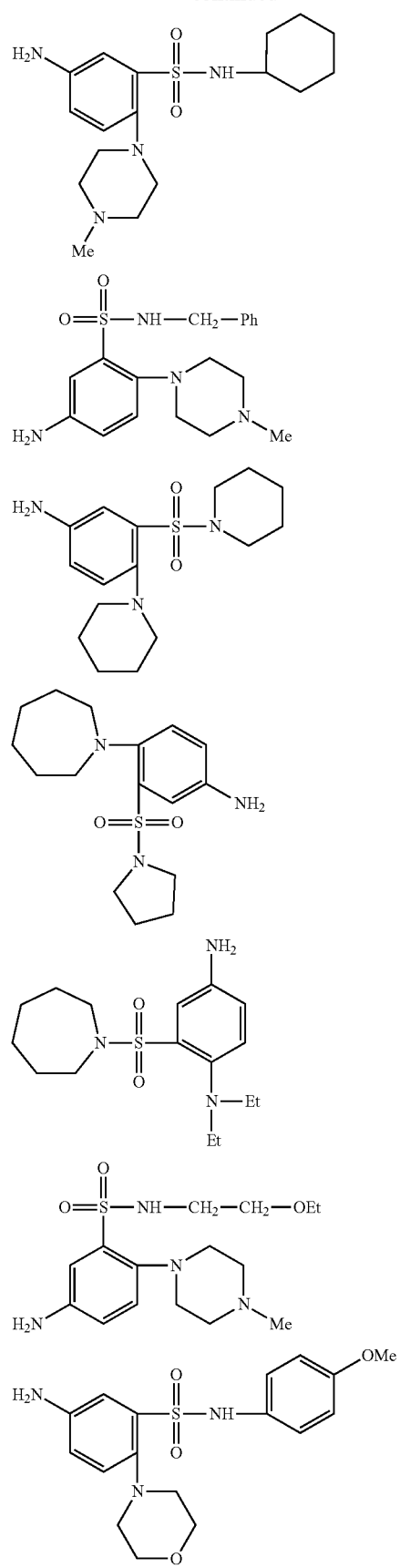
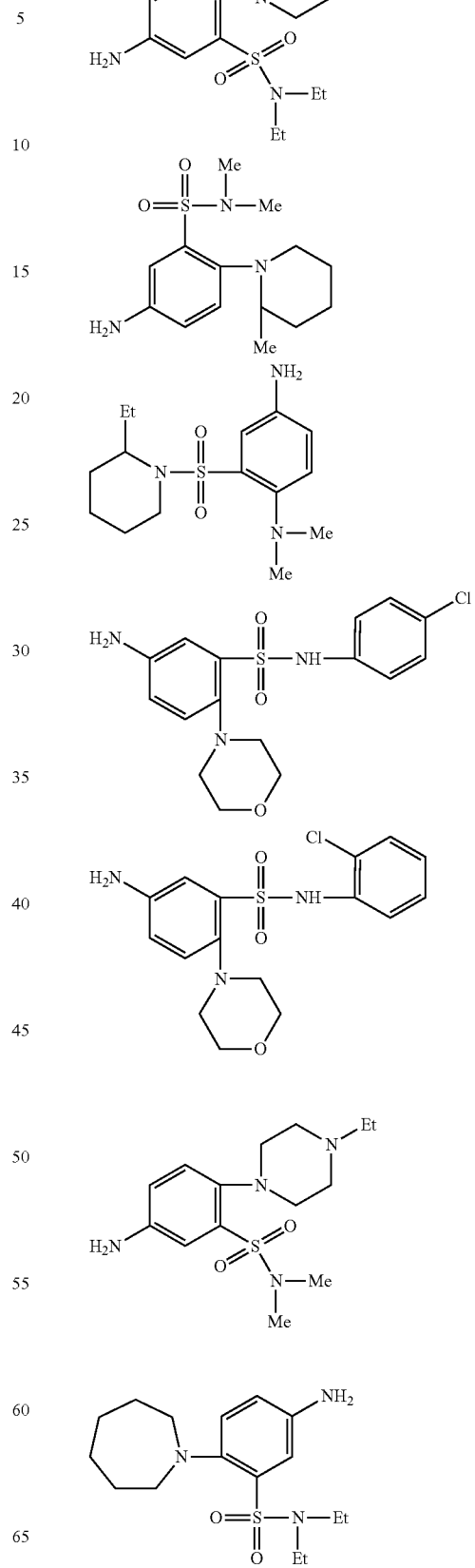

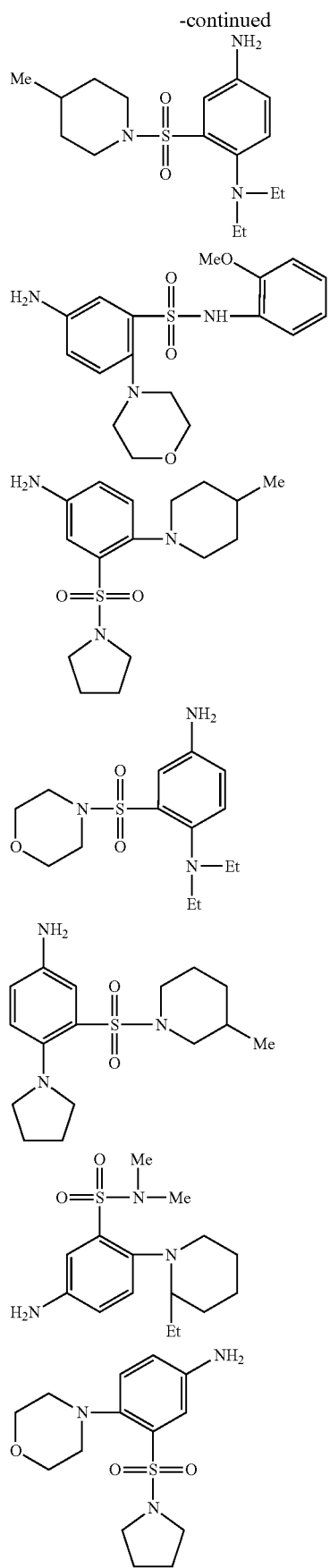
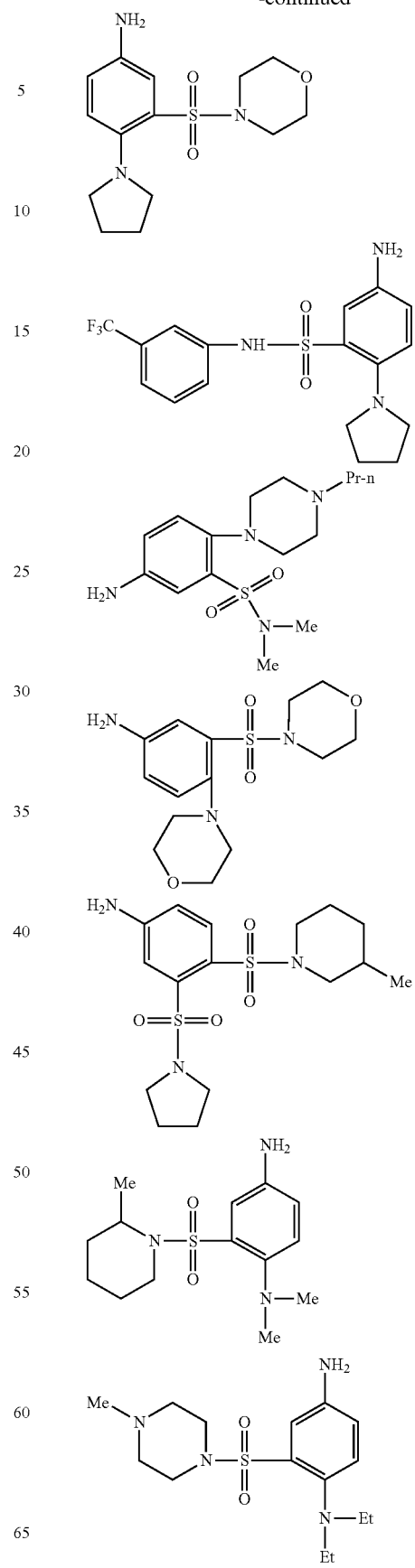

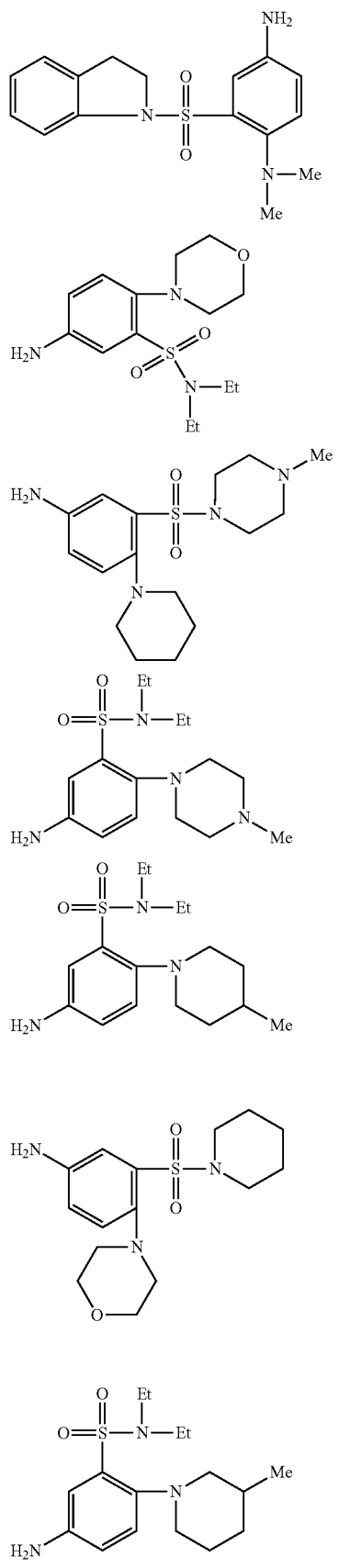
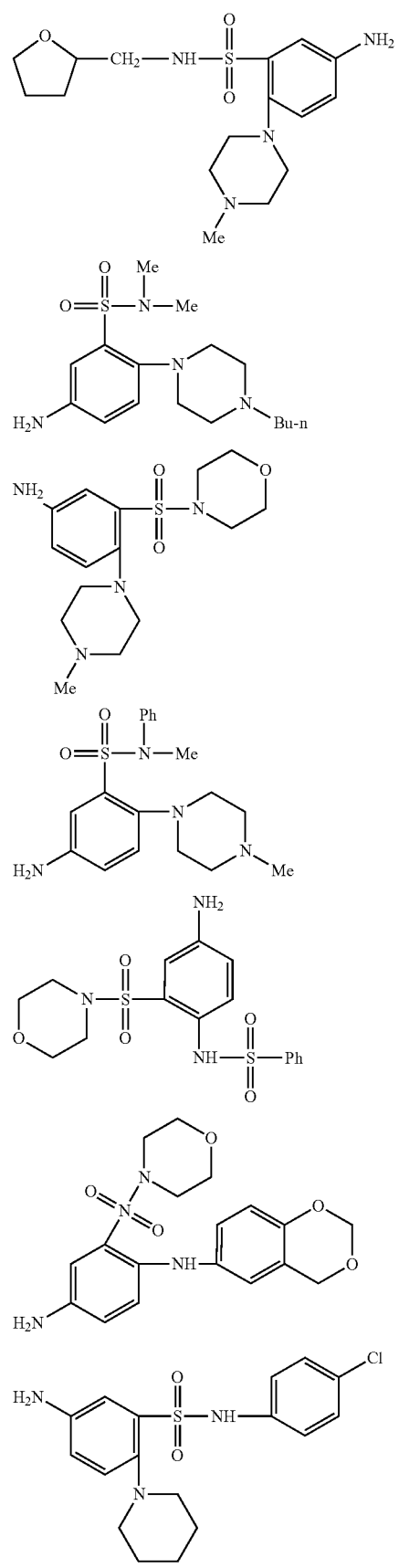

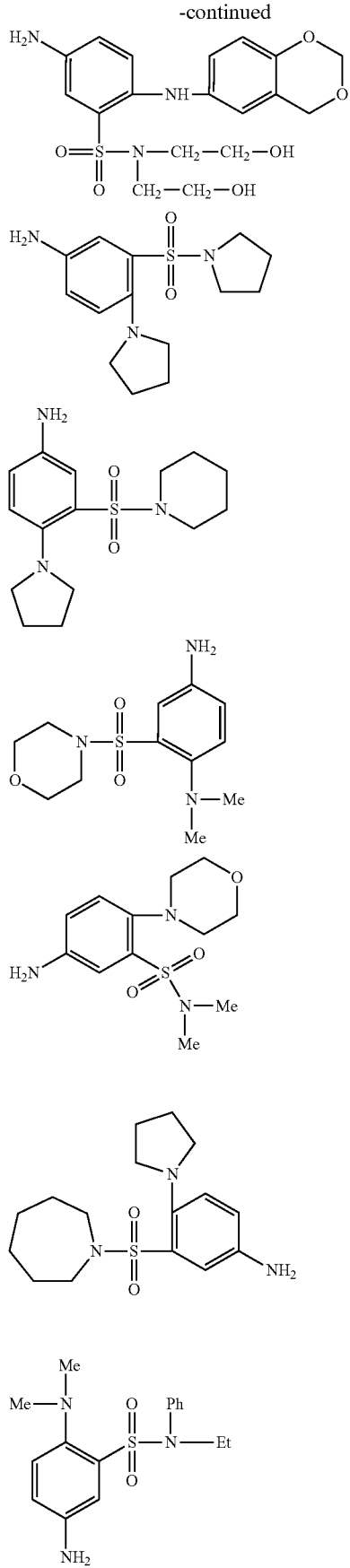
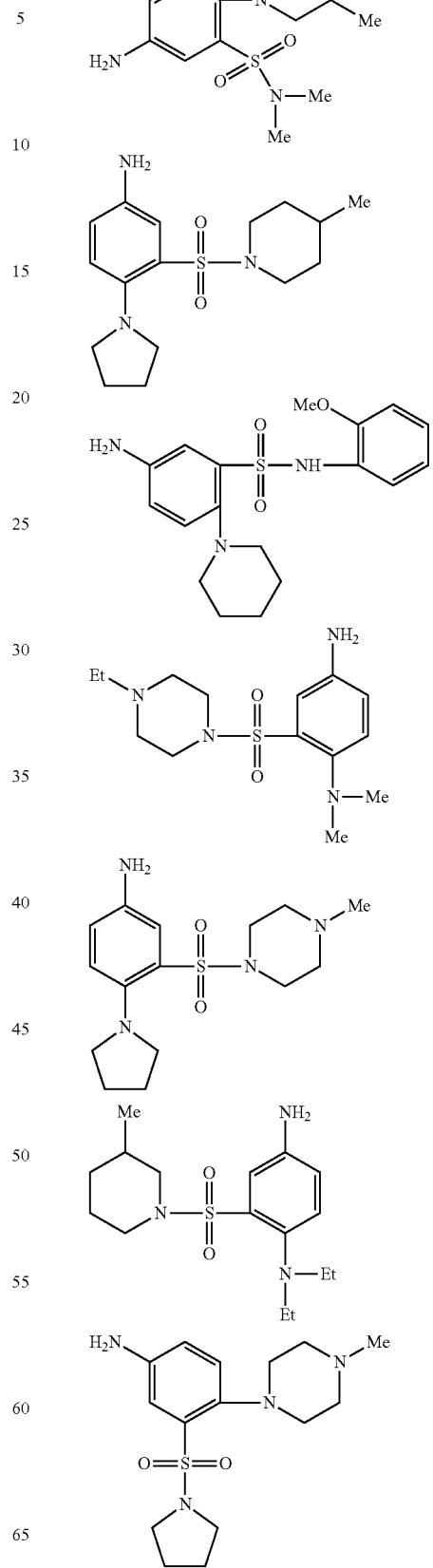

-continued
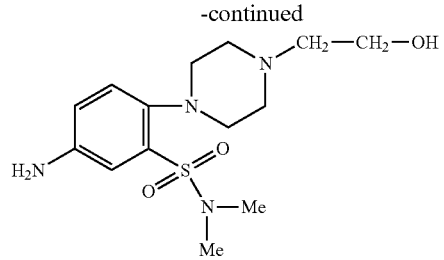
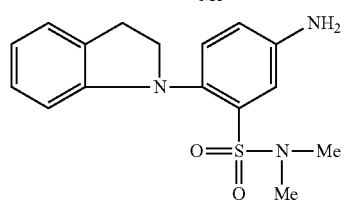
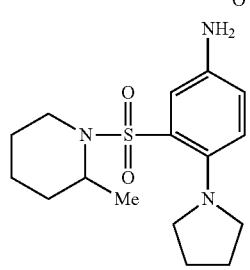
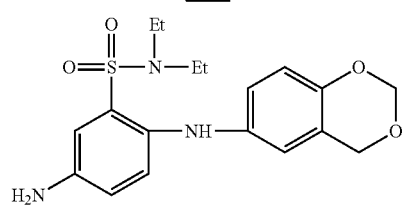
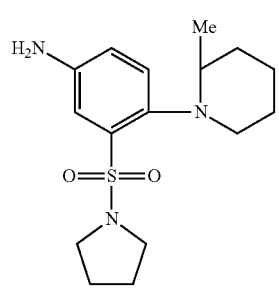
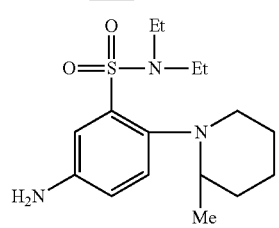
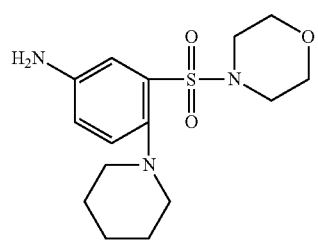
-continued
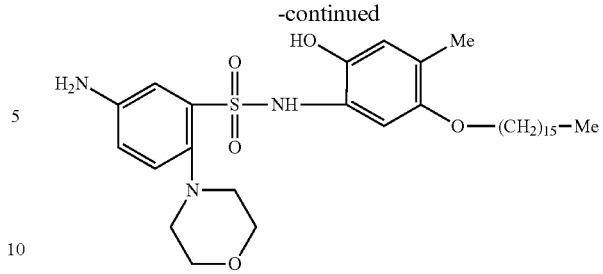
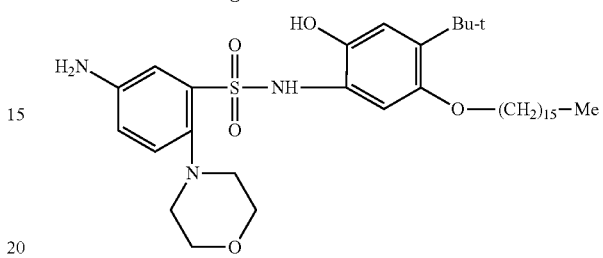
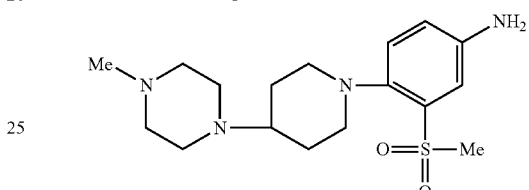
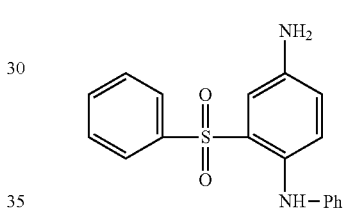
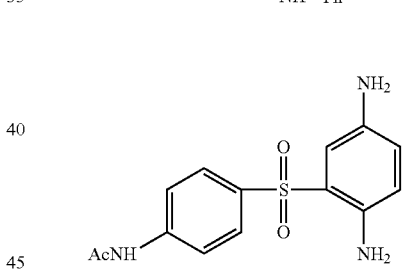
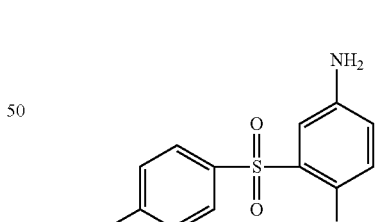
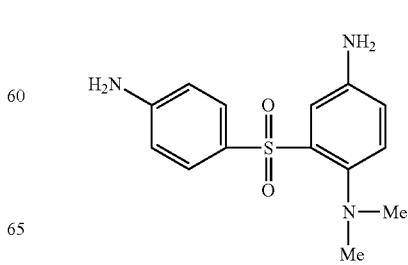

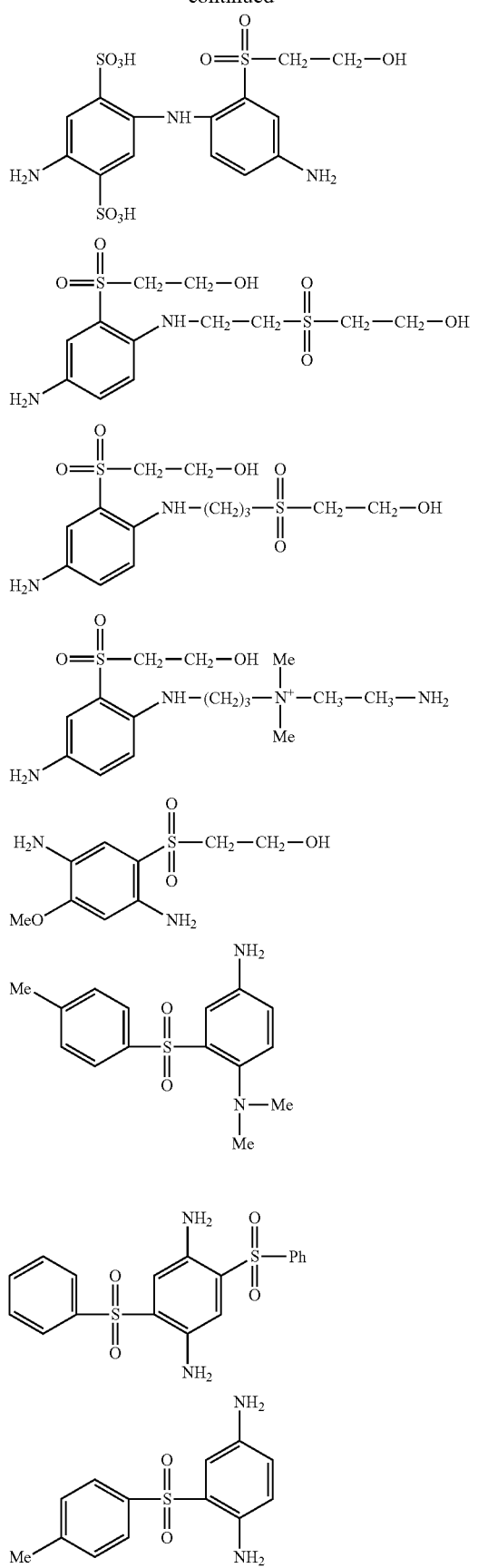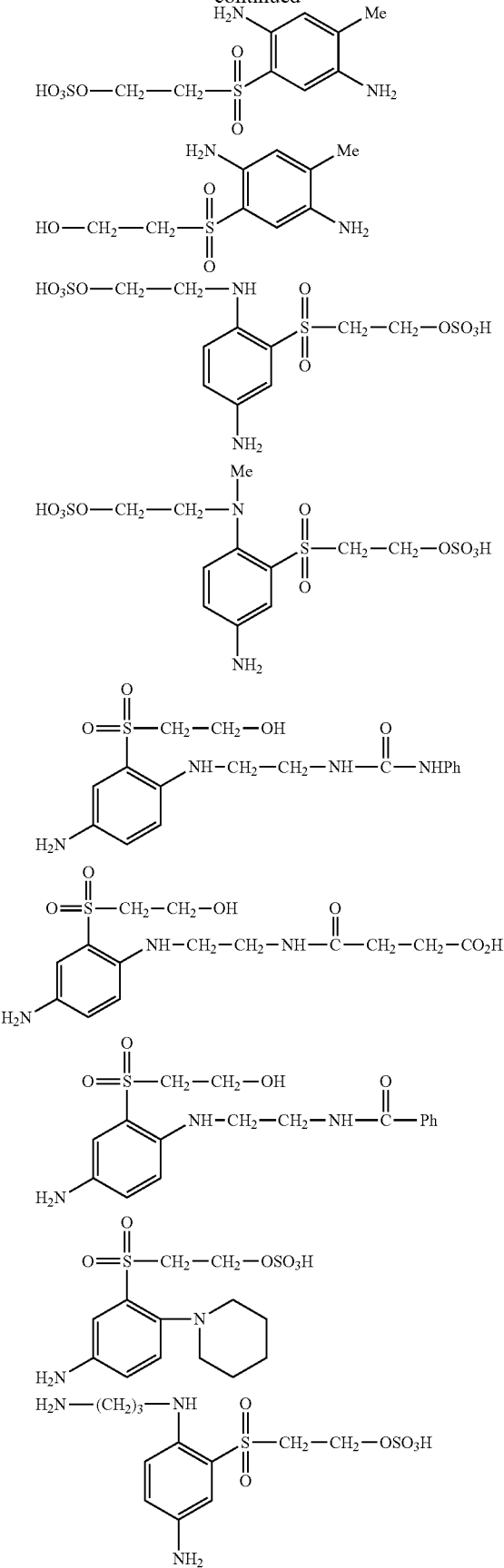

37
-continued
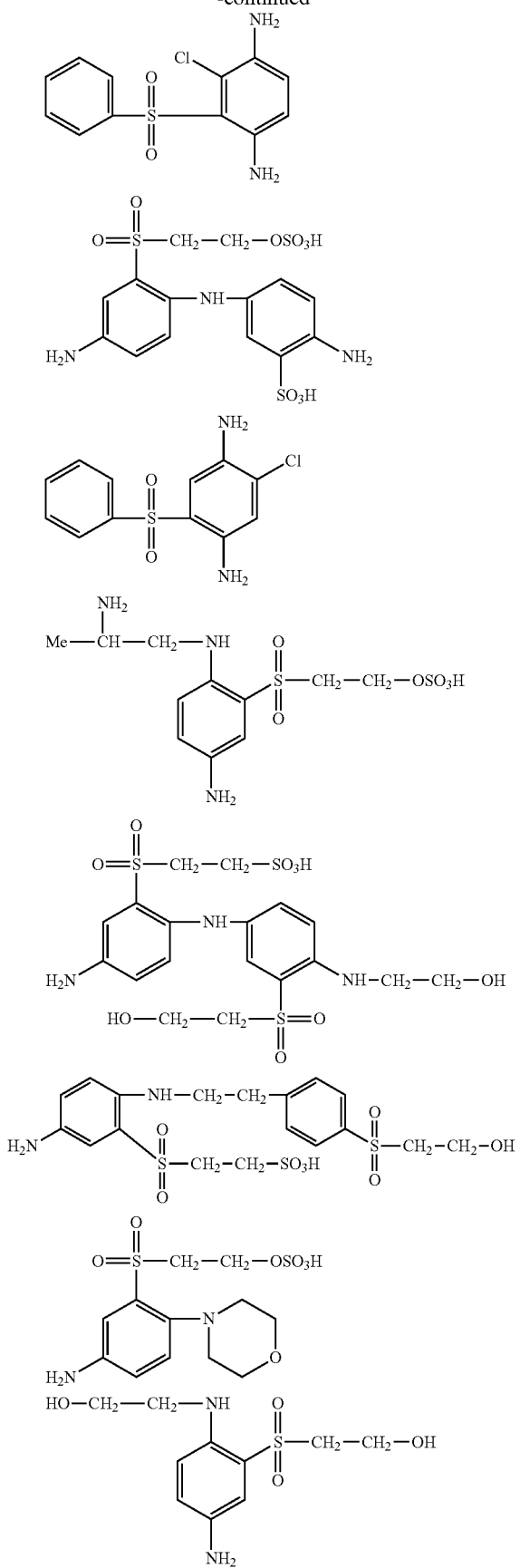
38
-continued
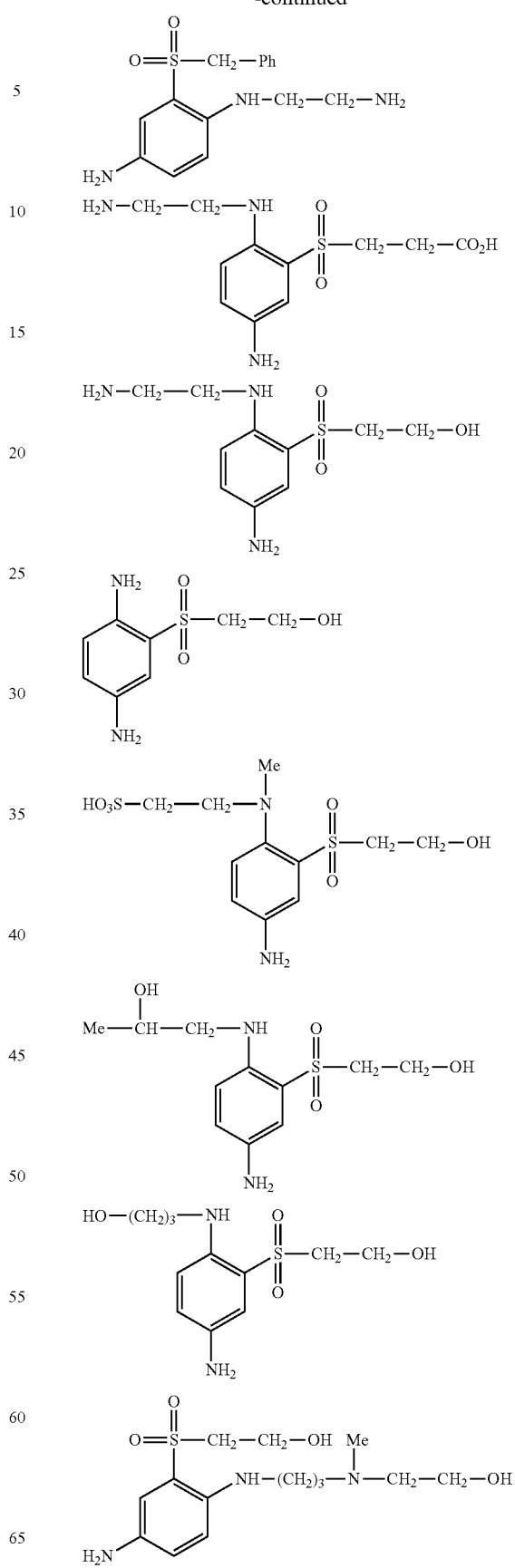

-continued
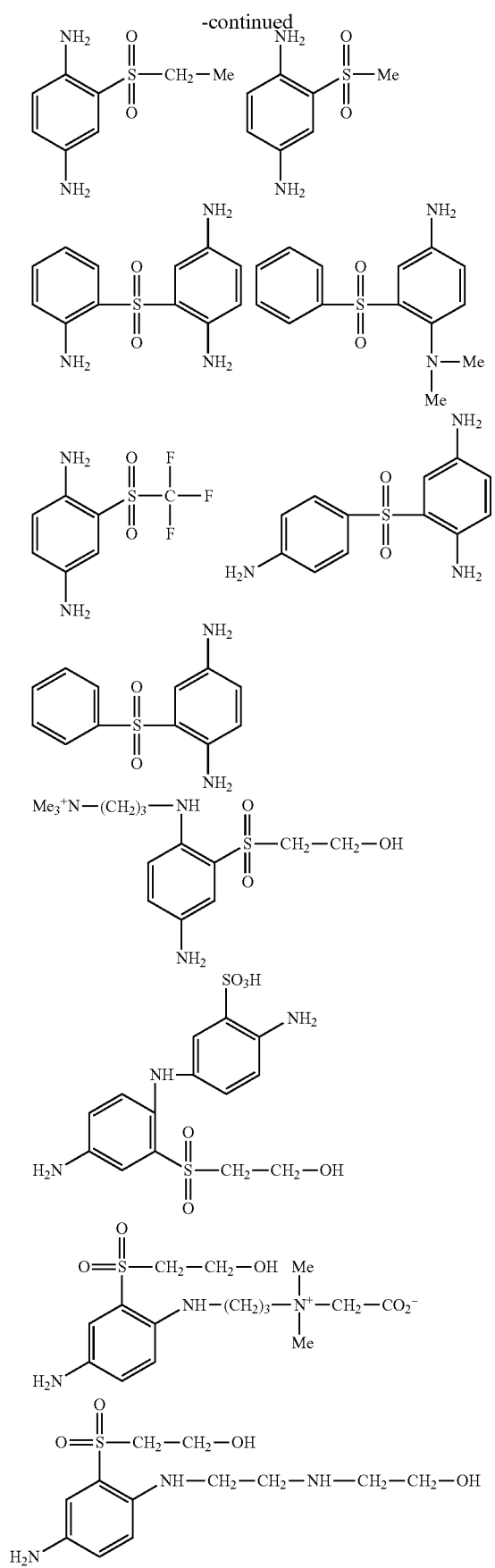
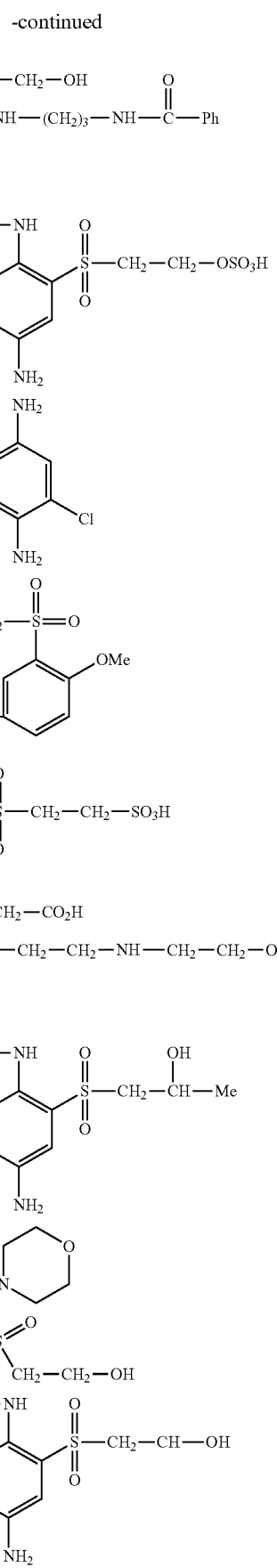

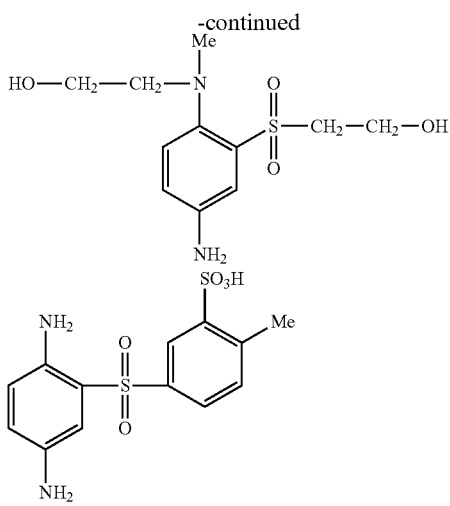

Preferably, the oxidation base(s) of formula (I) belong to the second variant.

Even more preferentially, the oxidation base(s) of formula (I) are chosen from the following compounds:

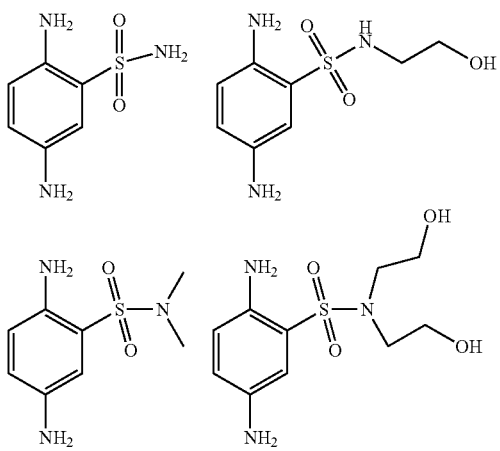

or the addition salts thereof, or solvates thereof.

Bases of Formula (II)

In accordance with a first embodiment of the invention, the oxidation base(s) is (are) chosen from the compounds of formula (II) in which:

Z represents a hydroxyl group;

$R_1$ represents:
- a hydroxyl radical,
- an amino radical —$NR_{11}R_{12}$, in which $R_{11}$ and $R_{12}$, which may be identical or different, represent:
  - a hydrogen atom;
  - a $C_1$-$C_{20}$ alkyl radical, optionally bearing at least:
    - one of the following groups: hydroxyl, $C_1$-$C_{15}$ alkoxy, phenoxy,
    - —COOH, —$SO_3H$,
    - ($C_1$-$C_2$)alkylcarbonyl amino (or ($C_2$-$C_3$)acylamino);
    - amino, optionally substituted with one or two $C_1$-$C_4$ alkyl radicals, which may be identical or different;
    - an aromatic or non-aromatic heterocycle having 5 to 6 ring members, optionally containing 1 or 2 endocyclic additional heteroatoms chosen from nitrogen; the nitrogen optionally bearing a hydrogen or a $C_1$-$C_4$ alkyl;
  - a $C_6$-$C_{10}$ aryl radical comprising an aromatic nucleus, or two fused aromatic nuclei, the aryl radical being optionally substituted with one or more hydroxyls or $C_1$-$C_4$ alkoxys;
  - a $C_6$-$C_{10}$ aryl radical comprising an aromatic nucleus optionally fused with another (hetero)aromatic nucleus, the heteroatom being nitrogen, the aryl radical being optionally substituted with at least one of the following groups: $C_1$-$C_4$ alkyl, hydroxyl, $C_1$-$C_4$ alkoxy, trifluoromethyl, 1 or 2 halogen(s), in particular chlorine(s), ($C_1$-$C_2$)alkylcarbonylamino (($C_2$-$C_3$)acylamino); aminosulfonyl optionally substituted with one or two $C_1$-$C_4$ alkyl groups; acetylenyl; $NH_2$—C(=$NH_2$)—;
  - a saturated or unsaturated, aromatic or non-aromatic heterocycle having 5 ring members, comprising from one to four heteroatoms, more particularly nitrogen,
  - it being possible for the $R_{11}$ and $R_{12}$ radicals to form, together with the nitrogen atom to which they are attached, a cationic or non-cationic saturated heterocycle having 5 to 6 ring members, optionally containing 1 endocyclic additional heteroatom chosen from nitrogen and oxygen; the nitrogen optionally bearing one or two $C_1$-$C_4$ alkyls, which may be identical or different, optionally bearing an —$SO_3H$ group; it being possible for the heterocycle to be substituted, on at least one of its carbon atoms, with a $C_1$-$C_4$ alkyl group optionally bearing a hydroxyl radical; a hydroxyl radical; the heterocycle being optionally fused to a $C_6$ aromatic nucleus; an aminocarbonyl radical; a mono- or di-($C_1$-$C_2$)alkylaminocarbonyl radical;

$R_2$ and $R_3$, which may be identical or different, represent:
- a hydrogen atom;
- a linear $C_1$-$C_{10}$, or branched $C_3$-$C_{10}$ alkyl radical, the alkyl radical being optionally substituted with at least one of the following groups: hydroxyl, $C_1$-$C_4$ alkoxy, amino optionally substituted with one or two $C_1$-$C_4$ alkyl radicals, which may be identical or different, mono- or di-($C_1$-$C_2$)alkylaminocarbonyl;
- two radicals $R_2$ and $R_3$, preferably alkyl, can form, together with the nitrogen atom to which they are connected, a saturated or unsaturated, aromatic or non-aromatic heterocycle having from 5 to 7 ring members, optionally containing 1 endocyclic additional heteroatom chosen from nitrogen and oxygen, the nitrogen optionally bearing one or two $C_1$-$C_4$ alkyl(s), which may be identical or different;

$R_4$, which may be identical or different, represent:
- a hydrogen atom;
- a $C_1$-$C_{20}$ alkyl or $C_2$-$C_6$ alkenyl; said alkyl or alkenyl being optionally substituted with at least one amino group which is unsubstituted or substituted with one or two $C_1$-$C_4$ alkyl groups, which may be identical or different; trifluoromethyl; a saturated or unsaturated (hetero)cycle having 5 or 6 ring members, optionally comprising one or two heteroatoms such as, for example, nitrogen; it being possible for the nitrogen to optionally bear a $C_1$-$C_4$ alkyl group;
- a saturated or unsaturated (hetero)cycle having 5 or 6 ring members, optionally comprising one or two heteroatoms such as, for example, nitrogen or oxygen; it being possible for the nitrogen to optionally bear a hydrogen atom or a $C_1$-$C_4$ alkyl group; it being possible for said (hetero)cycle to comprise an endocyclic carbonyl group, it being possible for said heterocycle to optionally be substituted with a hydroxyl group;

—COOH; —SO$_3$H;

halogens, such as, for example, chlorine, fluorine or bromine;

hydroxyl, C$_1$-C$_4$ alkoxy optionally bearing a carboxylic group, (C$_1$-C$_4$)alkylthio;

(C$_1$-C$_4$)alkylcarbonyl (or C$_2$-C$_4$ acyl); (C$_1$-C$_2$)alkylcarbonyl amino (or (C$_2$-C$_3$)acylamino); (C$_1$-C$_2$)alkylaminocarbonyl; aminocarbonyl;

trifluoromethyl;

aryl(C$_1$-C$_4$)alkyl;

two R$_4$ radicals borne by adjacent carbon atoms can form an aromatic or non-aromatic, fused (hetero)cycle having from 5 to 6 ring members; it being possible for said heterocycle to comprise at least one heteroatom, preferably 1 heteroatom, chosen from nitrogen and oxygen, it being possible for the nitrogen atom to bear a hydrogen atom or a C$_1$-C$_4$ alkyl radical; it being possible for said ring or heterocycle to be substituted, on at least one of the carbon atoms, with a C$_1$-C$_4$ alkyl radical;

it being understood that, if R$_1$ denotes a hydroxyl group, then at most two R$_4$ denote a hydrogen atom.

In accordance with a second embodiment of the invention, the oxidation base(s) are chosen from the compounds of formula (II) in which:

Z represents an amino group optionally substituted with one or two C$_1$-C$_4$ alkyl radicals, which may be identical or different;

R$_1$ represents:

an amino radical —NR$_{11}$R$_{12}$, in which R$_{11}$ and R$_{12}$, which may be identical or different, represent:
a hydrogen atom;
a C$_1$-C$_{20}$ alkyl radical, optionally bearing at least: one hydroxyl, C$_1$-C$_{15}$ alkoxy;
cyano;
mono- or di- (C$_1$-C$_2$)alkylaminocarbonyl;
amino, optionally substituted with one or two C$_1$-C$_4$ alkyl radicals, which may be identical or different;
an aromatic or non-aromatic heterocycle having 5 to 6 ring members, optionally containing 1 or 2 endocyclic heteroatoms chosen from nitrogen; the nitrogen optionally bearing a hydrogen atom or a C$_1$-C$_4$ alkyl;
a C$_6$-C$_{10}$ aryl radical comprising an aromatic nucleus, or two fused aromatic nuclei, the aryl radical being optionally substituted with at least one C$_1$-C$_4$ alkyl radical; a hydroxyl, C$_1$-C$_4$ alkoxy or trifluoromethyl;
a C$_6$-C$_{10}$ aryl radical comprising an aromatic nucleus optionally fused to another (hetero)aromatic nucleus, the heteroatom being nitrogen, the aryl radical being optionally substituted with at least one C$_1$-C$_4$ alkyl, hydroxyl or C$_1$-C$_4$ alkoxy group;
it being possible for the R$_{11}$ and R$_{12}$ radicals to form, together with the nitrogen atom to which they are attached, a saturated or unsaturated heterocycle having 5 or 6 ring members, optionally containing 1 endocyclic additional heteroatom, which may be identical or different, chosen from nitrogen and oxygen; the nitrogen optionally bearing one or two C$_1$-C$_4$ alkyls, which may be identical or different, optionally bearing an —SO$_3$H group; it being possible for the heterocycle to be substituted, on at least one of its carbon atoms, with one or two C$_1$-C$_4$ alkyl groups, which may be identical or different, optionally bearing a hydroxyl radical, an aminocarbonyl radical; a mono- or di-(C$_1$-C$_2$)alkylaminocarbonyl radical;

R$_2$ and R$_3$, which may be identical or different, represent:
a hydrogen atom;
a linear C$_1$-C$_{10}$, branched C$_3$-C$_{10}$, or cyclic C$_5$-C$_{10}$ alkyl radical; the alkyl radical being optionally substituted with at least one of the following groups: (C$_1$-C$_4$) alkylthio (RS—), cyano, hydroxyl, C$_1$-C$_4$ alkoxy, amino optionally substituted with one or two C$_1$-C$_4$ alkyl radicals, which may be identical or different, mono- or di- (C$_1$-C$_2$)alkylaminocarbonyl; a saturated, unsaturated or aromatic heterocycle having from 5 to 7 ring members, comprising 1 or 2 endocyclic heteroatoms chosen from nitrogen, oxygen and sulfur;
a saturated or unsaturated C$_5$-C$_{10}$ heterocyclic radical comprising at least one heteroatom such as nitrogen, the nitrogen atom optionally bearing a hydrogen atom or a C$_1$-C$_4$ alkyl radical;
a C$_6$-C$_{10}$ (hetero)aryl radical optionally comprising at least one endocyclic heteroatom, such as nitrogen; said radical being optionally substituted with one or two C$_1$-C$_4$ alkyl radicals, with one or two C$_1$-C$_4$ alkoxy(s), or with one or two amino(s) optionally substituted with one or two C$_1$-C$_4$ alkyl groups, which may be identical or different; two substituents borne by adjacent carbon atoms of the (hetero)aryl radical may form an aromatic or non-aromatic, fused ring or heterocycle comprising from 5 to 6 ring members, optionally comprising one or two endocyclic heteroatoms such as oxygen or nitrogen;
two radicals R$_2$ and R$_3$, preferably alkyl, can form, together with the nitrogen atom to which they are connected, a saturated or unsaturated, aromatic or non-aromatic heterocycle having 5 or 6 ring members, optionally containing 1 or 2 endocyclic additional heteroatoms, which may be identical or different, chosen from nitrogen, oxygen or sulfur, or else containing a carbonyl group; the nitrogen optionally bearing one or two C$_1$-C$_4$ alkyl(s), which may be identical or different; it being possible, where appropriate, for said heterocycle to be fused to an aromatic nucleus, preferably a C$_6$ aromatic nucleus, or to be fused to a saturated C$_5$-C$_7$, preferably C$_6$, ring, it being possible for said heterocycle to be substituted, on one of the carbon atoms, with one or two of the following radicals, which may be identical or different: C$_1$-C$_4$ alkyl optionally bearing a hydroxyl, C$_1$-C$_4$ alkoxy; hydroxyl; amino optionally substituted with one or two radicals which may be identical or different; aminocarbonyl; mono- or di-(C$_1$-C$_2$)alkylaminocarbonyl;

R$_4$, which may be identical or different, represent:
a hydrogen atom;
a C$_1$-C$_{20}$ alkyl;
halogens, such as, for example, chlorine, fluorine or bromine;
hydroxyl, C$_1$-C$_4$ alkoxy;
mono- or di-(C$_1$-C$_2$)alkylaminocarbonyl; aminocarbonyl.

Preferably, for the compounds of formula (II) in which at least two of the R$_4$ radicals denote a hydrogen atom.

In one preferred variant of the invention, the oxidation base(s) of formula (II) is (are) chosen from the compounds of the second embodiment previously described (i.e. compounds of formula (II) in which Z represents an amino group optionally substituted with one or two C$_1$-C$_4$ alkyl radicals, which may be identical or different), in which R$_1$ represents an amino radical —NR$_{11}$R$_{12}$, R$_{11}$ and R$_{12}$ being defined as previously. In addition, according to this variant, Z preferably represents an amino group optionally substituted with one or two $C_1$-$C_4$ alkyl radicals, which may be identical or different, preferably an amino group (—$NH_2$).

More particularly, the oxidation base(s) of formula (I) and/or (II), addition salts thereof or solvates thereof represent from 0.001% to 20% by weight relative to the weight of composition (A), and more preferentially from 0.1% to 10% by weight relative to the weight of composition (A).

Additional Oxidation Bases

Composition (A) used in the process of the invention may optionally comprise at least one additional oxidation base, other than the oxidation base(s) of formula (I) defined previously.

Additional oxidation bases that may be mentioned include benzene-based or heterocyclic oxidation bases and mixtures thereof, such as para-phenylenediamines, bis(phenyl)alkylenediamines, para-aminophenols, ortho-aminophenols and heterocyclic bases, addition salts thereof and solvates thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, addition salts thereof, solvates thereof and mixtures thereof.

Among the abovementioned para-phenylenediamines, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, addition salts thereof, solvates thereof and mixtures thereof are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, addition salts thereof, solvates thereof and mixtures thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, addition salts thereof, solvates thereof and mixtures thereof.

Among the ortho-aminophenols, examples that may be mentioned include 2-aminophenol, 2-amino-5-methylphenol, 2-amino-6-methylphenol and 5-acetamido-2-aminophenol, addition salts thereof, solvates thereof and mixtures thereof.

Among the heterocyclic bases, examples that may be mentioned include pyridine derivatives, pyrimidine derivatives and pyrazole derivatives, and preferably pyrazole derivatives.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof, described, for example, in patent application FR 2 801 308. Examples that may be mentioned include pyrazolo[1,5-a]pyrid-3-ylamine; 2-acetylaminopyrazolo[1,5-a]pyrid-3-ylamine; 2-(morpholin-4-yl)pyrazolo[1,5-a]pyrid-3-ylamine; 3-aminopyrazolo[1,5-a]pyridine-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-(morpholin-4-yl)pyrazolo[1,5-a]pyrid-3-ylamine; pyrazolo[1,5-a]pyridine-3,5-diamine; 5-(morpholin-4-yl)pyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)(2-hydroxyethyl)amino]ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-aminopyrazolo[1,5-a]pyridin-7-ol; and 2-(2-hydroxyethoxy)-3-aminopyrazolo[1,5-a]pyridine, and 2-(4-methylpiperazinium-1-yl)-3-aminopyrazolo[1,5-a]pyridine salts; addition salts thereof, solvates thereof and mixtures thereof.

Among the pyrimidine derivatives, mention may be made of the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, solvates thereof, and the tautomeric forms thereof, when a tautomeric equilibrium exists, and mixtures thereof.

Among the pyrazole derivatives, mention may be made of the compounds described in patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, addition salts thereof, solvates thereof and mixtures thereof. 4,5-Diamino-1-(β-methoxyethyl)pyrazole may also be used.

Use will preferably be made of a 4,5-diaminopyrazole and even more preferentially of 4,5-diamino-1-(β-hydroxyethyl)pyrazole and/or an addition salt and/or solvate thereof.

Pyrazole derivatives that may also be mentioned include diamino-N,N-dihydropyrazolopyrazolones and in particular those described in application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one, addition salts thereof, solvates thereof and mixtures thereof.

Use will preferably be made of 2,3-diamino-6,7-dihydro-1H,5H-pyrazolo[1,2-a]pyrazol-1-one and/or a salt or solvate thereof.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or a salt or solvate thereof.

The additional oxidation base(s), if they are present, each advantageously represent from 0.0001% to 10% by weight relative to the total weight of the composition, and preferably from 0.005% to 5% by weight relative to the total weight of composition (A).

Additional Couplers

The composition used according to the invention may also optionally comprise at least one coupler.

Among the couplers that may be used, mention may be made of meta-phenylenediamines, meta-aminophenols, meta-diphenols, naphthalene-based couplers, heterocyclic couplers, for instance indole derivatives, indoline derivatives, sesamol and derivatives thereof, pyridine derivatives, pyrazolotriazole derivatives, pyrazolones, indazoles, benzimidazoles, benzothiazoles, benzoxazoles, 1,3-benzodioxoles, quinolines, and the addition salts thereof and solvates thereof.

These couplers are more particularly chosen from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-di hydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, addition salts thereof, solvates thereof and mixtures thereof.

The additional coupler(s), if it (they) are present, each generally represent from 0.0001% to 10% by weight relative to the total weight of the composition, and preferably from 0.005% to 5% by weight relative to the total weight of composition (A) of the invention.

Other Additional Dyes

Composition (A) used in the process according to the invention may optionally comprise one or more synthetic or natural direct dyes, chosen from ionic or nonionic species, preferably cationic or nonionic species.

Examples of suitable synthetic direct dyes that may be mentioned include azo direct dyes; (poly)methine dyes such as cyanins, hemicyanins and styryls; carbonyl dyes; azine dyes; nitro(hetero)aryl dyes; tri(hetero)arylmethane dyes; porphyrin dyes; and phthalocyanin dyes, alone or as mixtures.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Use may also be made of extracts or decoctions comprising these natural dyes and in particular henna-based poultices or extracts.

When they are present, the direct dye(s) more particularly represent from 0.001% to 10% by weight and preferably from 0.005% to 5% by weight of the total weight of composition (A).

Fatty Substance

Composition (A) used in the process according to the invention comprises one or more fatty substances.

The term "fatty substance" means an organic compound that is insoluble in water at ordinary temperature (25° C.) and at atmospheric pressure (760 mmHg or $1.013 \times 10^5$ Pa) (solubility of less than 5%, preferably of less than 1% and even more preferentially of less than 0.1%). They bear in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The fatty substances of the invention do not contain any salified carboxylic acid groups.

In addition, the fatty substances of the invention are not (poly)oxyalkylenated or (poly)glycerolated ethers.

The term "oil" means a "fatty substance" that is liquid at room temperature (25° C.) and at atmospheric pressure (760 mmHg or $1.013 \times 10^5$ Pa).

The term "non-silicone oil" means an oil not containing any silicon atoms (Si) and the term "silicone oil" means an oil containing at least one silicon atom.

More particularly, the fatty substance(s) are chosen from $C_6$-$C_{16}$ hydrocarbons, hydrocarbons containing more than 16 carbon atoms, non-silicone oils of animal origin, triglycerides of plant or synthetic origin, fluoro oils, fatty alcohols, esters of fatty acids and/or of fatty alcohols other than triglycerides and non-silicone waxes, in particular plant waxes, non-silicone waxes other than fatty alcohols, and silicones, and mixtures thereof.

It is recalled that the fatty alcohols, esters and acids more particularly contain at least one saturated or unsaturated, linear or branched hydrocarbon-based group, comprising 6 to 30 and better still from 8 to 30 carbon atoms, which is optionally substituted, in particular, with one or more hydroxyl groups (in particular 1 to 4). If they are unsaturated, these compounds may comprise one to three conjugated or unconjugated carbon-carbon double bonds.

As regards the $C_6$-$C_{16}$ hydrocarbons, they are more particularly linear, branched or optionally cyclic, and are preferably alkanes. Examples that may be mentioned include hexane, cyclohexane, undecane, dodecane, isododecane, tridecane or isoparaffins, such as isohexadecane or isodecane, and mixtures thereof.

The linear or branched hydrocarbons of mineral or synthetic origin containing more than 16 carbon atoms are preferably chosen from liquid paraffins, petroleum jelly, liquid petroleum jelly, polydecenes and hydrogenated polyisobutene such as Parleam®, and mixtures thereof.

A hydrocarbon-based oil of animal origin that may be mentioned is perhydrosqualene.

The triglycerides of vegetable or synthetic origin are preferably chosen from liquid fatty acid triglycerides comprising from 6 to 30 carbon atoms, for instance heptanoic or octanoic acid triglycerides, or alternatively, more particularly from those present in plant oils, for instance sunflower oil, corn oil, soybean oil, marrow oil, grapeseed oil, sesame seed oil, hazelnut oil, apricot oil, macadamia oil, arara oil, castor oil, avocado oil, jojoba oil, shea butter oil or synthetic caprylic/capric acid triglycerides, for instance those sold by the company Stéarineries Dubois or those sold under the names Miglyol® 810, 812 and 818 by the company Dynamit Nobel, and mixtures thereof.

Fluoro oils that may be mentioned include perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for use in the invention are more particularly chosen from linear or branched, saturated or unsaturated alcohols comprising from 6 to 30 carbon atoms and preferably from 8 to 30 carbon atoms. Examples that may be mentioned include cetyl alcohol, isostearyl alcohol, stearyl alcohol and a mixture thereof (cetylstearyl alcohol), octyldodecanol, 2-butyloctanol, 2-hexyldecanol, 2-undecylpentadecanol, oeyl alcohol, linolenyl alcohol, ricinoleyl alcohol, undecylenyl alcohol and linoleyl alcohol, and mixtures thereof.

As regards the esters of fatty acids and/or of fatty alcohols other than the triglycerides mentioned above and non-silicone waxes, mention may be made especially of esters of saturated or unsaturated, linear $C_1$-$C_{26}$ or branched $C_3$-$C_{26}$ aliphatic monoacids or polyacids and of saturated or unsaturated, linear $C_1$-$C_{26}$ or branched $C_3$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oeyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oeyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate, and mixtures thereof.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate, and mixtures thereof.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar and fatty acid esters may be chosen in particular from the group comprising the esters or mixtures of sugar esters described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates or arachidonates, or mixtures thereof such as, in particular, oleate/palmitate, oleate/stearate or palmitate/stearate mixed esters.

More particularly, use is made of monoesters and diesters and especially sucrose, glucose or methylglucose mono- or dioleates, stearates, behenates, oleopalmitates, linoleates, linolenates and oleostearates.

An example that may be mentioned is the product sold under the name Glucate® DO by the company Amerchol, which is a methylglucose dioleate.

Examples of esters or mixtures of esters of sugar and of fatty acid that may also be mentioned include:
the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name Ryoto Sugar Esters, for example referenced B370 and corresponding to sucrose behenate formed from 20% monoester and 80% di-triester-polyester;
the sucrose mono-di-palmitostearate sold by the company Goldschmidt under the name Tegosoft® PSE.

The non-silicone wax(es) other than fatty alcohols are chosen especially from carnauba wax, candelilla wax, esparto wax, paraffin wax, ozokerite, plant waxes, such as olive tree wax, rice wax, hydrogenated jojoba wax or absolute flower waxes, such as the blackcurrant blossom essential wax sold by the company Bertin (France), or animal waxes, such as beeswaxes or modified beeswaxes (cerabellina); other waxes or waxy raw materials that may be used according to the invention are in particular marine waxes, such as the product sold by the company Sophim under the reference M82, polyethylene waxes or polyolefin waxes in general.

The silicones that may be used in the dye composition according to the present invention are volatile or non-volatile, cyclic, linear or branched silicones, which are unmodified or modified with organic groups, having a viscosity from $5 \times 10^{-6}$ to 2.5 m$^2$/s at 25° C., and preferably $1 \times 10^{-5}$ to 1 m$^2$/s.

The silicones that may be used in accordance with the invention may be in the form of oils, waxes, resins or gums.

Preferably, the silicone(s) are chosen from polydialkylsiloxanes, especially polydimethylsiloxanes (PDMSs), and organomodified polysiloxanes comprising at least one functional group preferably chosen from amino groups and alkoxy groups.

Organopolysiloxanes are defined in greater detail in Walter Noll's *Chemistry and Technology of Silicones* (1968), Academic Press. They may be volatile or non-volatile.

When they are volatile, the silicones are more particularly chosen from those with a boiling point of between 60° C. and 260° C., and even more particularly from:

(i) cyclic polydialkylsiloxanes comprising from 3 to 7 and preferably from 4 to 5 silicon atoms. These are, for example, octamethylcyclotetrasiloxane sold in particular under the name Volatile Silicone® 7207 by Union Carbide or Silbione® 70045 V 2 by Rhodia, decamethylcyclopentasiloxane sold under the name Volatile Silicone® 7158 by Union Carbide, and Silbione® 70045 V 5 by Rhodia, and mixtures thereof.

Mention may also be made of cyclocopolymers of the dimethylsiloxanes/methylalkylsiloxane type, such as Volatile Silicone® FZ 3109 sold by the company Union Carbide, of formula:

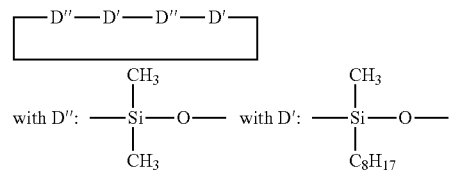

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*.

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:
the Silbione® oils of the 47 and 70 047 series or the Mirasil® oils sold by Rhodia, for instance the oil 70 047 V 500 000;
the oils of the Mirasil® series sold by the company Rhodia;
the oils of the 200 series from the company Dow Corning, such as DC200 with a viscosity of 60 000 mm$^2$/s;
the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of series 48 from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The silicone gums that may be used in accordance with the invention are especially polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:
- the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by the company Dow Corning;
- the mixtures of a polydimethylsiloxane gum and of a cyclic silicone, such as the product SF 1214 Silicone Fluid from the company General Electric; this product is a gum SF 30 corresponding to a dimethicone, having a number-average molecular weight of 500 000, dissolved in the oil SF 1202 Silicone Fluid corresponding to decamethylcyclopentasiloxane;
- mixtures of two PDMSs with different viscosities, and more particularly of a PDMS gum and of a PDMS oil, such as the product SF 1236 from the company General Electric. The product SF 1236 is a mixture of a gum SE 30 defined above with a viscosity of 20 m$^2$/s and of an oil SF 96 with a viscosity of 5×10$^{-6}$ m$^2$/s. This product preferably comprises 15% of gum SE 30 and 85% of an oil SF 96.

The organopolysiloxane resins that may be used in accordance with the invention are crosslinked siloxane systems containing the following units:

$R_2SiO_{2/2}$, $R_3SiO_{1/2}$, $RSiO_{3/2}$ and $SiO_{4/2}$, in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethyl siloxysilicate type resins sold especially under the names X22-4914, X21-5034 and X21-5037 by the company Shin-Etsu.

The organomodified silicones that may be used in accordance with the invention are silicones as defined above and comprising in their structure one or more organofunctional groups as mentioned previously, attached via a hydrocarbon-based group.

Besides the silicones described above, the organomodified silicones may be polydiarylsiloxanes, especially polydiphenylsiloxanes, and polyalkylarylsiloxanes functionalized with the organofunctional groups mentioned previously.

The polyalkylarylsiloxanes are chosen particularly from linear and/or branched polydimethyl/methylphenylsiloxanes and polydimethyl/diphenylsiloxanes with a viscosity ranging from 1×10$^{-5}$ to 5×10$^{-2}$ m$^2$/s at 25° C.

Among these polyalkylarylsiloxanes, examples that may be mentioned include the products sold under the following names:
- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

Among the organomodified silicones, mention may be made of polyorganosiloxanes comprising:
- substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amino groups are in particular $C_1$-$C_4$ aminoalkyl groups;
- alkoxylated groups, such as the product sold under the name Silicone Copolymer F-755 by SWS Silicones, and Abil Wax® 2428, 2434 and 2440 by the company Goldschmidt.

More particularly, the fatty substance(s) are chosen from compounds that are liquid or pasty at room temperature (25° C.) and at atmospheric pressure.

Preferably, the fatty substance(s) are chosen from compounds that are liquid at a temperature of 25° C. and at atmospheric pressure.

The fatty substance(s) are advantageously chosen from hydrocarbons containing more than 16 carbon atoms, $C_6$-$C_{16}$ alkanes, triglyceride oils of plant origin, liquid synthetic triglycerides, fatty alcohols, esters of fatty acids and/or of fatty alcohols other than triglycerides and non-silicone waxes, non-silicone waxes, and silicones, or mixtures thereof.

Preferably, the fatty substance(s) are chosen from liquid petroleum jelly, $C_6$-$C_{16}$ alkanes, polydecenes, liquid esters of fatty acids and/or of fatty alcohols other than triglycerides, and liquid fatty alcohols, or mixtures thereof.

More preferentially, the fatty substance(s) are chosen from liquid petroleum jelly, $C_6$-$C_{16}$ alkanes, polydecenes and liquid fatty alcohols such as 2-octyldodecanol.

The dye composition (A) according to the invention comprises at least 10% by weight of fatty substance, more particularly at least 15% by weight, preferably at least 20% by weight and even more particularly at least 25% by weight of fatty substance, relative to the weight of the dye composition.

Preferably, the fatty substance(s) are present in the dye composition (A) according to the invention in a content ranging from 10% to 80% by weight, advantageously from 15% to 80% by weight and more preferentially from 20% to 80% by weight relative to the weight of the dye composition. According to a more particular embodiment, the fatty substance content ranges from 25% to 80% by weight, preferably from 30% to 70% by weight and even more advantageously from 30% to 60% by weight relative to the weight of the dye composition.

Surfactants

Composition (A) used in the process according to the invention may also comprise one or more surfactants.

In particular, the surfactant(s) are chosen from anionic, amphoteric, zwitterionic, cationic and nonionic surfactants, and preferentially anionic and nonionic surfactants. The term "anionic surfactant" means a surfactant comprising, as ionic or ionizable groups, only anionic groups. These anionic groups are preferably chosen from the following groups: —C(O)OH, —C(O)O$^-$, —SO$_3$H, —S(O)$_2$O$^-$, —OS(O)$_2$OH, —OS(O)$_2$O$^-$, —P(O)OH$_2$, —P(O)$_2$O$^-$, —P(O)O$_2^-$, —P(OH)$_2$, =P(O)OH, —P(OH)O$^-$, =P(O)O$^-$, =POH and =PO$^-$, the anionic parts comprising a cationic counterion such as those derived from an alkali metal, an alkaline-earth metal, an amine or an ammonium.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids, and the corresponding non-salified forms of all these compounds, the alkyl and acyl groups of all these compounds comprising from 6 to 24 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts, and in particular sodium or magnesium salts.

Among the anionic surfactants mentioned, use is preferably made of ($C_6$-$C_{24}$)alkyl sulfates, ($C_6$-$C_{24}$)alkyl ether sulfates comprising from 2 to 50 ethylene oxide units, in particular in the form of alkali metal, ammonium, amino alcohol and alkaline-earth metal salts, or a mixture of these compounds.

In particular, it is preferred to use ($C_{12}$-$C_{20}$)alkyl sulfates, ($C_{12}$-$C_{20}$)alkyl ether sulfates comprising from 2 to 20 ethylene oxide units, especially in the form of alkali metal, ammonium, amino alcohol and alkaline-earth metal salts, or a mixture of these compounds. Better still, it is preferred to use sodium lauryl ether sulfate containing 2.2 mol of ethylene oxide.

The amphoteric or zwitterionic surfactant(s), which are preferably non-silicone surfactant(s), which may be used in the present invention may especially be derivatives of optionally quaternized secondary or tertiary aliphatic amines, in which derivatives the aliphatic group is a linear or branched chain comprising from 8 to 22 carbon atoms, the said amine derivatives containing at least one anionic group, for instance a carboxylate, sulfonate, sulfate, phosphate or phosphonate group. Mention may be made in particular of ($C_8$-$C_{20}$)alkylbetaines, sulfobetaines, ($C_8$-$C_{20}$)alkylamido($C_3$-$C_8$)alkylbetaines and ($C_8$-$C_{20}$)alkylamido($C_6$-$C_8$)alkylsulfobetaines.

Among the optionally quaternized secondary or tertiary aliphatic amine derivatives that can be used, as defined above, mention may also be made of the compounds of respective structures (A1) and (A2) below:

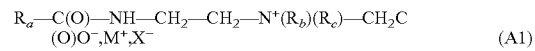

$$R_a\text{—C(O)—NH—CH}_2\text{—CH}_2\text{—N}^+(R_b)(R_c)\text{—CH}_2\text{C}(O)O^-, M^+, X^- \quad (A1)$$

in which formula (A1):
$R_a$ represents a $C_{10}$-$C_{30}$ alkyl or alkenyl group derived from an acid $R_a$COOH preferably present in hydrolysed coconut oil, or a heptyl, nonyl or undecyl group;
$R_b$ represents a β-hydroxyethyl group; and
$R_c$ represents a carboxymethyl group;
$M^+$ represents a cationic counterion derived from an alkali metal or alkaline-earth metal, such as sodium, an ammonium ion or an ion derived from an organic amine; and
$X^-$ represents an organic or mineral anionic counterion, such as that chosen from halides, acetates, phosphates, nitrates, ($C_1$-$C_4$)alkyl sulfates, ($C_1$-$C_4$)alkyl- or ($C_1$-$C_4$) alkylaryl sulfonates, in particular methyl sulfate and ethyl sulfate; or alternatively $M^+$ and $X^-$ are absent;

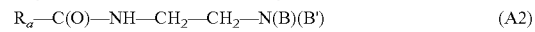

$$R_{a'}\text{—C(O)—NH—CH}_2\text{—CH}_2\text{—N(B)(B')} \quad (A2)$$

in which formula (A2):
B represents the group —$CH_2$—$CH_2$—O—X';
B' represents the group —$(CH_2)_z$Y', with z=1 or 2;
X' represents the group —$CH_2$—C(O)OH, —$CH_2$—C(O)OZ, —$CH_2$—$CH_2$—C(O)OH or —$CH_2$—$CH_2$—C(O)OZ, or a hydrogen atom;
Y' represents the group —C(O)OH, —C(O)OZ', —$CH_2$—CH(OH)—$SO_3$H or the group —$CH_2$—CH(OH)—$SO_3$—Z';
Z' represents a cationic counterion derived from an alkali metal or alkaline-earth metal, such as sodium, an ammonium ion or an ion derived from an organic amine;
$R_{a'}$ represents a $C_{10}$-$C_{30}$ alkyl or alkenyl group of an acid $R_{a'}$—COOH, which is preferably present in coconut oil or in hydrolysed linseed oil, an alkyl group, especially a $C_{17}$ group and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of the compounds of formula (A3):

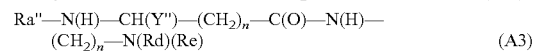

$$Ra''\text{—N(H)—CH(Y'')—(CH}_2)_n\text{—C(O)—N(H)—}(CH_2)_{n'}\text{—N(Rd)(Re)} \quad (A3)$$

in which formula (A3):
Y" represents the group —C(O)OH, —C(O)OZ", —$CH_2$—CH(OH)—$SO_3$H or the group —$CH_2$—CH(OH)—$SO_3$—Z";
Rd and Re, independently of each other, represent a $C_1$-$C_4$ alkyl or hydroxyalkyl radical;
Z" represents a cationic counterion derived from an alkali metal or alkaline-earth metal, such as sodium, an ammonium ion or an ion derived from an organic amine;
Ra" represents a $C_{10}$-$C_{30}$ alkyl or alkenyl group derived from an acid Ra"—C(O)OH, which is preferably present in coconut oil or in hydrolysed linseed oil;
n and n' denote, independently of each other, an integer ranging from 1 to 3.

Among the compounds of formula (B'2), mention may be made of the compound classified in the CTFA dictionary under the name sodium diethylaminopropyl cocoaspartamide and sold by the company Chimex under the name Chimexane HB.

Among the amphoteric or zwitterionic surfactants mentioned above, use is preferably made of $(C_8-C_{20})$alkylbetaines such as cocoylbetaine, and $(C_8-C_{20})$alkylamido$(C_3-C_8)$alkylbetaines such as cocamidopropylbetaine, and mixtures thereof. More preferentially, the amphoteric or zwitterionic surfactant(s) are chosen from cocamidopropylbetaine and cocoylbetaine.

The cationic surfactant(s) that may be used in the composition according to the invention comprise, for example, optionally polyoxyalkylenated primary, secondary or tertiary fatty amine salts, quaternary ammonium salts, and mixtures thereof.

Examples of quaternary ammonium salts that may especially be mentioned include:

those corresponding to the general formula (A4) below:

in which formula (A4):

$R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 8 to 30 carbon atoms and preferably from 12 to 24 carbon atoms; and $X^-$ represents an organic or mineral anionic counterion, such as that chosen from halides, acetates, phosphates, nitrates, $(C_1-C_4)$alkyl sulfates, $(C_1-C_4)$alkyl- or $(C_1-C_4)$ alkylaryl sulfonates, in particular methyl sulfate and ethyl sulfate.

The aliphatic groups of $R_8$ to $R_{11}$ may also comprise heteroatoms especially such as oxygen, nitrogen, sulfur and halogens.

The aliphatic groups of $R_8$ to $R_{11}$ are chosen, for example, from $C_1-C_{30}$ alkyl, $C_1-C_{30}$ alkoxy, polyoxy$(C_2-C_6)$alkylene, $C_1-C_{30}$ alkylamide, $(C_{12}-C_{22})$alkylamido$(C_2-C_6)$alkyl, $(C_{12}-C_{22})$alkyl acetate, and $C_1-C_{30}$ hydroxyalkyl groups; $X^-$ is an anionic counterion chosen from halides, phosphates, acetates, lactates, $(C_1-C_4)$alkyl sulfates, and $(C_1-C_4)$alkyl- or $(C_1-C_4)$alkylarylsulfonates.

Among the quaternary ammonium salts of formula (A4), preference is given firstly to tetraalkylammonium chlorides, for instance dialkyldimethylammonium or alkyltrimethylammonium chlorides in which the alkyl group contains approximately from to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (A5) below:

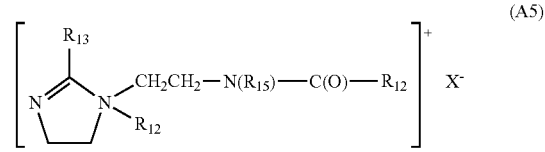

in which formula (A5):

$R_{12}$ represents an alkenyl or alkyl group comprising from 8 to 30 carbon atoms, for example fatty acid derivatives of tallow;

$R_{13}$ represents a hydrogen atom, a $C_1-C_4$ alkyl group or an alkenyl or alkyl group comprising from 8 to 30 carbon atoms;

$R_{14}$ represents a $C_1-C_4$ alkyl group;

$R_{15}$ represents a hydrogen atom or a $C_1-C_4$ alkyl group;

$X^-$ represents an organic or mineral anionic counterion, such as that chosen from halides, phosphates, acetates, lactates, $(C_1-C_4)$alkyl sulfates, $(C_1-C_4)$alkyl- or $(C_1-C_4)$alkylaryl sulfonates.

$R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name Rewoquat® W 75 by the company Rewo;

quaternary diammonium or triammonium salts, particularly of formula (A6) below:

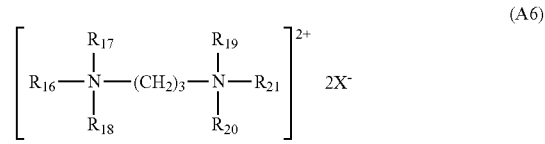

in which formula (A6):

$R_{16}$ denotes an alkyl group comprising approximately from 16 to 30 carbon atoms, which is optionally hydroxylated and/or interrupted with one or more oxygen atoms;

$R_{17}$ is chosen from hydrogen, an alkyl group comprising from 1 to 4 carbon atoms or a group —$(CH_2)_3$—$N^+$ $(R_{16a})(R_{17a})(R_{18a})$, $X^-$;

$R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms; and X—, which may be identical or different, represent an organic or mineral anionic counterion, such as that chosen from halides, acetates, phosphates, nitrates, $(C_1-C_4)$ alkyl sulfates, $(C_1-C_4)$alkyl- or $(C_1-C_4)$alkylaryl sulfonates, in particular methyl sulfate and ethyl sulfate.

Such compounds are, for example, Finquat CT-P, provided by the company Finetex (Quaternium 89), and Finquat CT, provided by the company Finetex (Quaternium 75);

quaternary ammonium salts containing one or more ester functions, such as those of formula (A7) below:

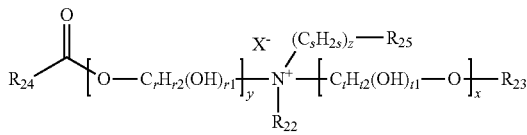
(A7)

in which formula (A7):
$R_{22}$ is chosen from $C_1$-$C_6$ alkyl groups and $C_1$-$C_6$ hydroxyalkyl or $C_1$-$C_6$ dihydroxyalkyl groups;
$R_{23}$ is chosen from:
the group

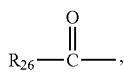, linear or branched, saturated or unsaturated $C_1$-$C_{22}$ hydrocarbon-based groups $R_{27}$,
a hydrogen atom,
$R_{25}$ is chosen from:
the group

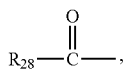, linear or branched, saturated or unsaturated $C_1$-$C_6$ hydrocarbon-based groups $R_{29}$,
a hydrogen atom,
$R_{24}$, $R_{26}$ and $R_{28}$, which may be identical or different, are chosen from linear or branched, saturated or unsaturated $C_7$-$C_{21}$ hydrocarbon-based groups;
r, s and t, which may be identical or different, are integers ranging from 2 to 6,
r1 and t1, which may be identical or different, are equal to 0 or 1, with r2+r1=2r and t1+t2=2t,
y is an integer ranging from 1 to 10,
x and z, which may be identical or different, are integers ranging from 0 to 10,
$X^-$ represents an organic or mineral anionic counterion, with the proviso that the sum x+y+z is from 1 to 15, that when x is 0 then $R_{23}$ denotes $R_{27}$, and that when z is 0 then $R_{25}$ denotes a linear or branched, saturated or unsaturated $C_1$-$C_6$ hydrocarbon-based radical $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anionic counterion $X^-$ is preferably a halide, such as chloride, bromide or iodide; a ($C_1$-$C_4$)alkyl sulfate or a ($C_1$-$C_4$)alkyl- or ($C_1$-$C_4$)alkylarylsulfonate. However, it is possible to use methanesulfonate, phosphate, nitrate, tosylate, an anion derived from an organic acid, such as acetate or lactate, or any other anion that is compatible with the ammonium containing an ester function.

The anionic counterion $X^-$ is even more particularly chloride, methyl sulfate or ethyl sulfate.

Use is made more particularly, in the composition according to the invention, of the ammonium salts of formula (A7) in which:
$R_{22}$ denotes a methyl or ethyl group,
x and y are equal to 1,
z is equal to 0 or 1,
r, s and t are equal to 2,
$R_{23}$ is chosen from:
the group

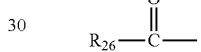

methyl, ethyl or $C_{14}$-$C_{22}$ hydrocarbon-based groups,
a hydrogen atom,
$R_{25}$ is chosen from:
the group

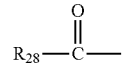

a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based radicals are linear.

Among the compounds of formula (A7), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a vegetable oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

It is also possible to use the ammonium salts containing at least one ester function that are described in patents U.S. Pat. No. 4,874,554 and U.S. Pat. No. 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethylhydroxyethylammonium salts, and mixtures thereof, and more particularly behenyltrimethylammonium chloride, cetyltrimethylammonium chloride and dipalmitoylethylhydroxyethylammonium methosulfate, and mixtures thereof.

Examples of nonionic surfactants that may be used in the composition used according to the invention are described, for example, in the *Handbook of Surfactants* by M. R. Porter, published by Blackie & Son (Glasgow and London), 1991, pp. 116-178.

Examples of oxyalkylenated nonionic surfactants that may be mentioned include:
oxyalkylenated ($C_8$-$C_{24}$)alkylphenols;
saturated or unsaturated, linear or branched, oxyalkylenated $C_8$-$C_{30}$ alcohols;
saturated or unsaturated, linear or branched, oxyalkylenated $C_8$-$C_{30}$ amides;
esters of saturated or unsaturated, linear or branched, $C_8$-$C_{30}$ acids and of polyethylene glycols;
polyoxyethylenated esters of saturated or unsaturated, linear or branched, $C_8$-$C_{30}$ acids and of sorbitan;
esters of fatty acids and of sucrose;
($C_8$-$C_{30}$)alkylpolyglycosides, ($C_8$-$C_{30}$)alkenylpolyglycosides, which are optionally oxyalkylenated (0 to 10 oxyalkylene units) and which comprise 1 to 15 glucose units, ($C_8$-$C_{30}$)alkylglucoside esters;
saturated or unsaturated, oxyethylenated plant oils;
condensates of ethylene oxide and/or of propylene oxide, inter alia, alone or as mixtures;
N—($C_8$-$C_{30}$)alkylglucamine derivatives and N—($C_8$-$C_{30}$)acyl-methylglucamine derivatives;
aldobionamides;
amine oxides;
oxyethylenated and/or oxypropylenated silicones;
the surfactants containing a number of moles of ethylene oxide and/or of propylene oxide ranging advantageously from 1 to 100, more particularly from 2 to 100, preferably from 2 to 50 and more advantageously from 2 to 30. Advantageously, the nonionic surfactants do not comprise any oxypropylene units.

In accordance with a preferred embodiment of the invention, the oxyalkylenated nonionic surfactants are chosen from oxyethylenated $C_8$-$C_{30}$ alcohols comprising from 1 to 100 mol and more particularly from 2 to 100 mol of ethylene oxide; polyoxyethylenated esters of saturated or unsaturated, linear or branched $C_8$-$C_{30}$ acids and of sorbitan comprising from 1 to 100 mol and better still from 2 to 100 mol of ethylene oxide.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to formula (A8) below:

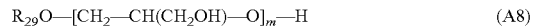

$$R_{29}O-[CH_2-CH(CH_2OH)-O]_m-H \qquad (A8)$$

in which formula (A8):
$R_{29}$ represents a linear or branched $C_8$-$C_{40}$ and preferably $C_8$-$C_{30}$ alkyl or alkenyl radical; and
m represents a number ranging from 1 to 30 and preferably from 1 to 10.

As examples of compounds of formula (A8) that are suitable within the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (A8) may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

Preferentially, the nonionic surfactant used in the process of the invention in the composition is a monooxyalkylenated or polyoxyalkylenated, particularly monooxyethylenated or polyoxyethylenated, or monooxypropylenated or polyoxypropylenated, nonionic surfactant, or a combination thereof, more particularly monooxyethylenated or polyoxyethylenated, monoglycerolated or polyglycerolated surfactants and alkylpolyglucosides.

Even more preferentially, the nonionic surfactants are chosen from polyoxyethylenated sorbitan esters, polyoxyethylenated fatty alcohols and alkylpolyglucosides, and mixtures thereof.

More preferably still, the nonionic surfactants are chosen from polyoxyethylenated sorbitol esters and polyoxyethylenated fatty alcohols, and mixtures thereof.

The surfactants, if they are present, represent in composition (A) used in the process according to the invention a content ranging from 0.1% to 50% by weight and better still from 0.5% to 20% by weight relative to the total weight of composition (A).

Basifying Agents

According to a particularly advantageous embodiment of the invention, composition (A) used in the process of the invention comprises one or more basifying agents.

The basifying agent(s) may be mineral or organic or hybrid.

For the purposes of the present invention, the term "mineral compound" means any compound bearing in its structure one or more elements from columns 1 to 13 of the Periodic Table of the Elements other than hydrogen.

According to one particular embodiment of the invention, the mineral basifying agent contains one or more elements from columns 1 and 2 of the Periodic Table of the Elements other than hydrogen.

In one preferred variant, the mineral basifying agent has the following structure:

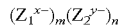

in which:

$Z_2$ denotes a metal from columns 1 to 13 and preferably from column 1 or 2 of the Periodic Table of the Elements, for instance sodium or potassium;

$Z_1{}^{x-}$ denotes an anion chosen from the ions $CO_3{}^{2-}$, $OH^-$, $HCO_3{}^{2-}$, $SiO_3{}^{2-}$, $HPO_4{}^{2-}$, $PO_4{}^{3-}$ and $B_4O_7{}^{2-}$, and preferably from the ions $CO_3{}^{2-}$, $OH^-$ and $SiO_3{}^{2-}$;

x denotes 1, 2 or 3;

y denotes 1, 2, 3 or 4;

m and n denote, independently of each other, 1, 2, 3 or 4; with n·y=m·x.

Preferably, the mineral basifying agent corresponds to the following formula $(Z_1{}^{x-})_m(Z_2{}^{y+})_n$, in which $Z_2$ denotes a metal from columns 1 and 2 of the Periodic Table of the Elements; $Z_1{}^{x-}$ denotes an anion chosen from the ions $CO_3{}^{2-}$, $OH^-$ and $SiO_3{}^{2-}$, x is 1, y denotes 1 or 2, and m and n denote, independently of each other, 1 or 2 with n·y=m·x.

The mineral basifying agent(s) are preferably chosen from aqueous ammonia, alkali metal carbonates or bicarbonates such as sodium or potassium carbonates and sodium or potassium bicarbonates, sodium hydroxide and potassium hydroxide, metasilicates such as sodium metasilicate and potassium metasilicate or mixtures thereof.

The organic basifying agent(s) are preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise any alkyl or alkenyl fatty chains comprising more than ten carbon atoms.

The organic basifying agent(s) are chosen, for example, from alkanolamines, oxyethylenated and/or oxypropylenated ethylenediamines, amino acids and the compounds of formula (i) below:

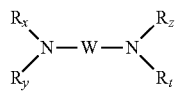

in which formula (i), W is a divalent $C_1$-$C_6$ alkylene radical optionally substituted with one or more hydroxyl groups or a $C_1$-$C_6$ alkyl radical, and/or optionally interrupted with one or more heteroatoms such as O, or NRu, and Rx, Ry, Rz, Rt and Ru, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (i) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

The organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that can be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that can be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (ii) below:

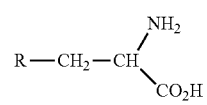

in which formula (III), R represents a group chosen from:

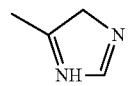

—$(CH_2)_3NH_2$
—$(CH_2)_2NH_2$, —$(CH_2)_2NHCONH_2$; and

The compounds corresponding to formula (II) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino) methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the basifying agent(s) present in the composition of the invention are chosen from aqueous ammonia, alkanolamines, amino acids in neutral or ionic form, in particular basic amino acids, and preferably corresponding to those of formula (ii).

Even more preferentially, the basifying agent(s) are chosen from alkanolamines such as monoethanolamine (MEA).

Advantageously, composition (A) according to the invention has a content of basifying agent(s) ranging from 0.01% to 30% by weight and preferably from 0.1% to 20% by weight relative to the weight of the said composition.

According to a first particular embodiment, composition (A) according to the invention or else the process according to the invention does not use ammonia, or a salt thereof, as basifying agent.

According to a second embodiment, if composition (A) does use ammonia, or a salt thereof, as basifying agent, its content should advantageously not exceed 0.03% by weight (expressed as $NH_3$), preferably should not exceed 0.01% by weight, relative to the weight of the composition of the invention.

Preferably, if composition (A) comprises ammonia, or a salt thereof, then the amount of basifying agent(s) other than ammonia is greater than that of ammonia (expressed as $NH_3$).

Solvent

Composition (A) according to the invention may also comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The organic solvent(s), if they are present, represent a content usually ranging from 1% to 40% by weight and preferably from 5% to 30% by weight relative to the weight of the composition.

Other Additives

Composition (A) according to the invention may also contain various adjuvants conventionally used in hair dye compositions, such as anionic, cationic, nonionic, amphoteric or zwitterionic polymers or mixtures thereof; mineral thickeners, and in particular fillers such as clays or talc; organic thickeners with, in particular, anionic, cationic, nonionic and amphoteric polymeric associative thickeners; antioxidants; penetrants; sequestrants; fragrances; dispersants; film-forming agents; ceramides; preserving agents; opacifiers.

The above adjuvants are generally present in an amount, for each of them, of between 0.01% and 20% by weight relative to the weight of the composition.

The composition may especially comprise one or more mineral thickeners chosen from organophilic clays and fumed silicas, or mixtures thereof.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylarylsulfonates and amine oxides, and mixtures thereof.

Mention may be made, as organophilic clays, of quaternium-18 bentonites, such as those sold under the names Bentone 3, Bentone 38 and Bentone 38V by the company Rheox, Tixogel VP by the company United Catalyst and Claytone 34, Claytone 40 and Claytone XL by the company Southern Clay; stearalkonium bentonites, such as those sold under the names Bentone 27 by the company Rheox, Tixogel LG by the company United Catalyst and Claytone AF and Claytone APA by the company Southern Clay; and quaternium-18/benzalkonium bentonites, such as those sold under the names Claytone HT and Claytone PS by the company Southern Clay.

The fumed silicas may be obtained by high-temperature hydrolysis of a volatile silicon compound in an oxyhydrogen flame, producing a finely divided silica. This process makes it possible especially to obtain hydrophilic silicas which bear a large number of silanol groups at their surface. Such hydrophilic silicas are sold, for example, under the names Aerosil 130®, Aerosil 200®, Aerosil 255®, Aerosil 300® and Aerosil 380® by the company Degussa and Cab-O-Sil HS-5®, Cab-O-Sil EH-5®, Cab-O-Sil LM-130®, Cab-O-Sil MS-55® and Cab-O-Sil M-5® by the company Cabot.

It is possible to chemically modify the surface of the silica via chemical reaction in order to reduce the number of silanol groups. It is possible in particular to replace silanol groups with hydrophobic groups: a hydrophobic silica is then obtained.

The hydrophobic groups may be:

trimethylsiloxyl groups, which are obtained in particular by treating fumed silica in the presence of hexamethyldisilazane. Silicas thus treated are known as "Silica silylate" according to the CTFA (6th Edition, 1995). They are sold, for example, under the references Aerosil R812® by the company Degussa and Cab-O-Sil TS-530® by the company Cabot.

dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA (6th Edition, 1995). They are sold, for example, under the references Aerosil R972® and Aerosil R974® by the company Degussa and Cab-O-Sil TS-610® and Cab-O-Sil TS-720® by the company Cabot.

The fumed silica preferably has a particle size that may be nanometric to micrometric, for example ranging from about 5 to 200 nm.

Preferably, the composition comprises a hectorite, an organomodified bentonite or an optionally modified fumed silica.

When it is present, the mineral thickener represents from 1% to 30% by weight relative to the weight of the composition.

The composition may also comprise one or more organic thickeners.

These thickeners may be chosen from fatty acid amides (coconut monoethanolamide or diethanolamide, oxyethylenated carboxylic acid monoethanolamide alkyl ether), polymeric thickeners such as cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum), acrylic acid or acrylamidopropanesulfonic acid crosslinked homopolymers and associative polymers (polymers comprising hydrophilic regions and fatty-chain hydrophobic regions (alkyl or alkenyl containing at least 10 carbon atoms) that are capable, in an aqueous medium, of reversibly combining with each other or with other molecules).

According to a specific embodiment, the organic thickener is chosen from cellulose-based thickeners (hydroxyethylcellulose, hydroxypropylcellulose, carboxymethylcellulose), guar gum and derivatives thereof (hydroxypropyl guar), gums of microbial origin (xanthan gum, scleroglucan gum) and crosslinked homopolymers of acrylic acid or of acrylamidopropanesulfonic acid, and preferably from cellulose-based thickeners with in particular hydroxyethylcellulose.

The content of organic thickener(s), if they are present, usually ranges from 0.01% to 20% by weight and preferably from 0.1% to 5% by weight relative to the weight of composition (A).

Chemical Oxidizing Agents

As indicated previously, composition (A) according to the invention comprises one or more chemical oxidizing agents other than atmospheric oxygen.

More particularly, the oxidizing agent(s) are chosen from hydrogen peroxide, urea peroxide, alkali metal bromates or ferricyanides, peroxygenated salts, for instance alkali metal or alkaline-earth metal persulfates, perborates, peracids and precursors thereof, and percarbonates, and peracids and precursors thereof.

This chemical oxidizing agent advantageously consists of hydrogen peroxide and especially in aqueous solution (aqueous hydrogen peroxide solution), the concentration of which may range more particularly from 0.1% to 50% by weight, even more preferably from 0.5% to 20% by weight and better still from 1% to 15% by weight relative to composition (A).

Processes According to the Invention

Advantageously, composition (A) used in the process according to the invention results from the mixing of a composition (A1) comprising one or more oxidation bases of formula (I) and/or (II) as defined previously and of a composition (A2) comprising one or more chemical oxidizing agents other than atmospheric oxygen, and as defined previously.

Compositions (A1) and (A2) are preferably aqueous. They may especially be in the form of direct or inverse emulsions.

Composition (A) may also result from the mixing of three compositions, the first two being the compositions (A1) and (A2) as defined above and the third composition being a composition (A3) comprising at least one fatty substance as defined previously.

This composition (A3) may be anhydrous or aqueous. It is preferably anhydrous.

Usually, the pH of the oxidizing composition (A2) is less than 7.

In accordance with a first variant of the present invention, composition (A) and composition (B) comprising one or more metal catalysts as defined previously are mixed together extemporaneously just before application to the fibres, and the mixture produced is then applied to wet or dry fibres; (A) resulting from the prior mixing, just before application, of compositions (A1), (A2) and, where appropriate, (A3).

Compositions (A1), (A2), (A3) and (B) may contain, independently of each other, compounds chosen from surfactants, fatty substances, solvents, thickeners and basifying agents as described for composition (A).

Preferably, composition (A1) comprises at least one basifying agent as described previously.

In a second variant of the invention, composition (B) and composition (A) are successively applied to wet or dry keratin fibres, with or without intermediate rinsing; (A) possibly resulting from the extemporaneous mixing, just before application, of compositions (A1), (A2) and, where appropriate, (A3).

Preferably, in this second variant, a rinsing step is performed between the application of compositions (A) and (B) or (B) and (A).

Preferably, in this second variant, composition (B) is applied before composition (A).

After the rinsing step, the fibres are preferably manually dried.

The leave-on time of composition (B) on the keratin fibres may range from 5 to 15 minutes and is preferably 10 minutes.

In particular, composition (B) is applied to the keratin fibres and is left on for 10 minutes at room temperature.

Preferably, composition (B) is sprayed onto the keratin fibres.

In addition, composition (A), advantageously resulting from the extemporaneous mixing of compositions (A1), (A2) and, where appropriate, (A3), may be left in place on the keratin fibres for a time generally from about 1 minute to 1 hour, preferably from 5 minutes to 40 minutes and preferably for 35 minutes.

The temperature during the process is conventionally between room temperature (between 15 and 25° C.) and 80° C. and preferably between room temperature and 60° C.

After the treatment, the human keratin fibres are optionally rinsed with water, optionally washed with a shampoo and then rinsed with water, before being dried or left to dry.

Preferably, after the treatment, the keratin fibres are dried under a hood at a temperature ranging from 50 to 80° C.

According to a particularly advantageous embodiment, the process for dyeing keratin fibres comprises the use:

(a) of a composition (B) comprising one or more metal catalysts chosen from inorganic metal salts chosen from halides, carbonates, sulfates and phosphates, especially hydrated or non-hydrated halides, metal salts of organic acids chosen from citrates, lactates, glycolates, gluconates, acetates, propionates, fumarates, oxalates and tartrates, especially gluconates, and mixtures thereof, (b) of a composition (A1) comprising one or more oxidation bases of formula (I), optionally one or more alkaline agents chosen from alkanolamines, amino acids in neutral or ionic form, and optionally at least one fatty substance, and (c) of a composition (A2) comprising one or more chemical oxidizing agents other than atmospheric oxygen, optionally at least one fatty substance, and optionally (d) of a composition (A3) comprising one or more fatty substances chosen from liquid petroleum jelly, C6-C16 alkanes, polydecenes, liquid esters of fatty acids and/or of fatty alcohols, and liquid fatty alcohols, or mixtures thereof, in which composition (B) is applied to the keratin fibres, the keratin fibres are rinsed, the said fibres are advantageously manually dried, and composition (A) resulting from the extemporaneous mixing of compositions (A1), (A2) and optionally (A3) is then applied; the content of fatty substances representing at least 10% by weight relative to the weight of composition (A).

Finally, the invention relates to a multi-compartment device comprising a first compartment containing a cosmetic composition (B) comprising one or more metal catalysts as defined previously, a second compartment containing a cosmetic composition (A1) comprising one or more oxidation bases of formula (I) and/or (I I) as defined previously, and a third compartment containing a composition (A2) comprising one or more chemical oxidizing agents other than atmospheric oxygen, as defined previously; compositions (A1) and/or (A2) possibly comprising at least one fatty substance; composition (A) resulting from the mixing of compositions (A1) and (A2) comprising at least 10% by weight of fatty substance, relative to the total weight of composition (A).

According to a particular embodiment, the device comprises a fourth compartment comprising a composition (A3) comprising one or more fatty substances, the said composition (A3) being intended to be mixed with compositions (A1) and (A2); composition (A1) and/or composition (A2) possibly comprising at least one fatty substance; the content of fatty substance in composition (A) resulting from the mixing of compositions (A1), (A2) and (A3) being greater than or equal to 10% by weight relative to the weight of composition (A).

The device is suitable for implementing the dyeing process according to the invention.

One of the other subjects of the invention is a composition corresponding to composition (A) also comprising at least one metal catalyst.

The examples that follow serve to illustrate the invention without, however, being limiting in nature.

Example 2

The following compositions are prepared from the following ingredients in the following proportions (indicated in grams)

1) Composition containing the metal salt

| | B (g %) |
|---|---|
| Laureth-2 | 2 g |
| Decyl glucoside | 2 g |
| Mineral oil | 78.5 g |
| PEG-150/decyl glucoside/SMDI copolymer | 0.5 g |
| Manganese gluconate (CAS No. 6485-39-8) | 0.4 g |
| Water | qs 100 g |

2) Dye Compositions

The dye composition is prepared at the time of the use by mixing:

6.7 g of composition A3
2.7 g of composition A1
10 g of composition A2

Each of the compositions is specified in the tables below (the proportions are expressed in gram %, unless otherwise indicated):

| Composition A3 | A3 (g %) |
|---|---|
| Liquid petroleum jelly | 64.5 |
| 2-Octyldodecanol | 11.5 |
| Distearyldimethylammonium-modified hectorite | 3 |
| Propylene carbonate | 1 |
| Oxyethylenated (4 OE) sorbitan monolaurate | 11 |
| Glycol distearate | 8 |
| Oxyethylenated (2 OE) lauryl alcohol | 1 |

| Composition A'1 | A'1 (g %) |
|---|---|
| Base according to the invention of formula (II) | $20 \times 10^{-3}$ mol % |
| 1-β-Hydroxyethyloxy-2,4-diarninobenzene dihydrochloride | $20 \times 10^{-3}$ mol % |
| Free monoethanolamine | 14.37 |
| Sodium metabisulfite | 0.7 |
| L-Ascorbic acid | 0.25 |
| EDTA | 0.287 |
| Propylene glycol | 6.2 |
| Ethanol | 15 |
| Hexylene glycol | 3 |
| Dipropylene glycol | 3 |
| Benzyl alcohol | 5 |
| Deionized water | qs 100 |

| Composition A2 (oxidizing agent) | A2 (g %) |
|---|---|
| 50% hydrogen peroxide solution | 12 |
| Liquid petroleum jelly | 20 |
| Cetylstearyl alcohol (30/70 C16/C18) | 8 |
| Oxyethylenated cetylstearyl alcohol (33 OE) | 3 |
| Tetrasodium pyrophosphate, decahydrate | 0.03 |
| Crystalline sodium hexahydroxystannate | 0.04 |
| Diethylenetriaminepentaacetic acid, pentasodium salt as a 40% aqueous solution | 0.15 |
| Polydimethyldiallylammonium chloride at 40% in water, non-stabilized | 0.5 |
| Poly[(dimethyliminio)-1,3-propanediyl(dimethyliminio)-1,6-hexanediyl dichloride] as a 60% aqueous solution | 0.25 |
| Phosphoric acid | qs pH 2 ± 0.2 |
| Protected oxyethylenated (4 OE) rapeseed acid amides | 1.3 |
| Vitamin E | 0.1 |
| Glycerol | 0.5 |
| Deionized water | qs 100 |

3) Dyeing Process

Locks of natural Caucasian hair containing 90% white hairs are successively treated with:

composition B, which is left on for 10 minutes at room temperature and then rinsed out, and the locks are manually dried (variant in accordance with the invention and which is not performed for the comparative test)

the dye composition resulting from the extemporaneous mixing, before application, of A'1+A2+A3 which is then left on for 35 minutes at room temperature (in accordance with the two processes, according to the invention and comparative), after this leave-on time, the locks are washed with iNOA POST shampoo, rinsed and then dried under a hood.

4) Results

The colorations obtained are measured using a Minolta CM2600D spectrocolorimeter.

The colour build-up ($\Delta E_{Lab}^*$) was evaluated in the CIE L*a*b* system. In this L*a*b* system, L* represents the intensity of the colour, a* indicates the green/red colour axis and b* indicates the blue/yellow colour axis. The lower the value of L*, the darker or more intense the colour.

The value of $\Delta E_{Lab}^*$ was calculated from the values of L*a*b* according to equation (i) below:

$$\Delta E_{Lab}^* = \sqrt{(L^* - L_o^*)^2 + (a^* + a_o^*)^2 + (b^* + b_o^*)^2} \quad \text{(i)}$$

The coloration build-up ($\Delta E_{Lab}*$) was calculated on locks of untreated hair ($L_o*$, $a_o*$ and $b_o*$) and on locks of dyed hair ($L*$, $a*$ and $b*$). The higher the value of $\Delta E*$, the better the colour build-up.

| Base used/Structure | | $L*$ | $a*$ | $b*$ | ($\Delta E_{Lab}*$) build-up | Gain in $\Delta E_{Lab}*$ |
|---|---|---|---|---|---|---|
| Uncoloured | | 59.14 | 1.14 | 16.16 | | |
| 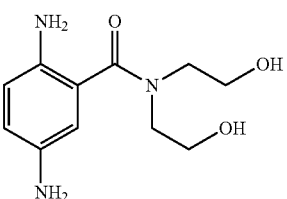 | Comparative | 25.78 | 3.7 | −7.26 | 40.84 | 4.75 |
| | Invention | 18.34 | 2.29 | −4.15 | 45.59 | |
| 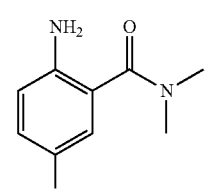 | Comparative | 24.35 | 3.81 | −6.49 | 41.6 | 4.35 |
| | Invention | 17.21 | 1.81 | −2.63 | 45.95 | |

The invention claimed is:

1. A composition comprising:
   (a) at least one fatty substance, the fatty substance present in an amount of at least 10% by weight, relative to the total weight of the composition;
   (b) at least one oxidation base chosen from:
   i) compounds of formula (I), the addition salts thereof, solvates thereof, or mixtures thereof:

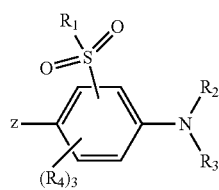

(I)

wherein:
$R_1$ is chosen from:
   a hydroxyl radical,
   a $C_1$-$C_{10}$ alkyl radical optionally bearing at least one hydroxyl, $C_1$-$C_4$ alkoxy, —O—$SO_3H$, —$SO_3H$, —COOH, halo group, or fluoro,
   an amino radical optionally substituted with one or two identical or different groups, chosen from:
      a $C_1$-$C_{20}$ linear or $C_3$-$C_{20}$ branched or cyclic alkyl group or a $C_3$-$C_{20}$ linear or branched alkenyl group, the alkyl or alkenyl group optionally bearing at least one hydroxyl or $C_1$-$C_4$ alkoxy radical optionally substituted with a hydroxyl group, an amino optionally substituted with one or two identical or different $C_1$-$C_4$ alkyl groups, pyridyl, furyl, or combinations thereof; the alkyl or alkenyl group optionally forming, together with the nitrogen atom that bears them, a saturated or unsaturated 5- to 7-membered heterocycle optionally comprising one or two identical or different additional endocyclic heteroatoms, chosen from nitrogen, oxygen or sulfur, the heterocycle being optionally substituted on a carbon or nitrogen atom with at least one $C_1$-$C_4$ alkyl radical, and the heterocycle being optionally fused to a phenyl nucleus;
   a R'$SO_2$— group wherein R' is chosen from a $C_1$-$C_4$ alkyl or phenyl radical;
   benzyl ($C_6H_6$—$CH_2$—), phenyl, or naphthyl groups optionally substituted with at least one $C_1$-$C_4$ alkyl group; trifluoromethyl or hydroxyl groups; a $C_1$-$C_{20}$ alkoxy group; an amino group; a sulfonic (—$SO_3H$) group; a halogen atom, or chlorine; or
   a saturated, unsaturated, or aromatic 5- or 6-membered heterocycle comprising one to three identical or different endocyclic heteroatoms, nitrogen, or sulfur,
a phenyl or benzyl radical, optionally substituted with at least one radical chosen from $C_1$-$C_6$ alkyl, $C_1$-$C_{20}$ alkoxy, hydroxyl, amino, trifluoromethyl, a ($C_1$-$C_4$) alkylamido (alk-CONH—) groups, a sulfonic (—$SO_3H$) group, a halogen atom, or chlorine;
$R_2$ and $R_3$, which may be identical or different, are chosen from a hydrogen atom or a $C_1$-$C_4$ alkyl radical,
$R_4$, which may be identical or different, is chosen from a hydrogen atom, a $C_1$-$C_4$ alkyl radical, a $C_1$-$C_4$ alkoxy radical, a carboxylic (—COOH) group, a sulfonic (—$SO_3H$) group, a ($C_1$-$C_4$)alkyl($C_6$)arylsulfonyl (alk-aryl—$SO_2$—) group, a sulfonamido ($NH_2$—$SO_2$—) group, a halogen, chlorine, or bromine,
   with the proviso that two radicals $R_4$ borne by adjacent carbon atoms may optionally form, with the carbon atoms, a saturated, unsaturated or aromatic 6-membered ring, optionally comprising an endocyclic nitrogen atom, the ring being optionally fused to another 6-membered aromatic nucleus or optionally substituted with a ($C_1$-$C_4$)alkylamido (alk-CONH—) or sulfonic (—$SO_3H$) radical; and
Z is chosen from a hydroxyl group or an amino group optionally substituted with one or two identical or different radicals $R_6$ chosen from:

a linear $C_1$-$C_{10}$ alkyl or branched $C_3$-$C_{10}$ alkyl radical,
the linear $C_1$-$C_{10}$ alkyl or branched $C_3$-$C_{10}$ alkyl radical optionally interrupted with a heteroatom chosen from oxygen, an amino group optionally substituted with a $C_1$-$C_4$ alkyl radical, or an ammonium group substituted with three identical or different $C_1$-$C_4$ alkyl radicals;
the alkyl radical optionally bearing at least one group chosen from:
  a hydroxyl radical;
  an amino radical optionally substituted with a $C_1$-$C_4$ alkyl group;
  an ammonium radical substituted with three identical or different $C_1$-$C_4$ alkyl groups, wherein at least one of the groups is optionally substituted with a —COOH group or a hydroxyl group;
  a phenyl optionally bearing a radical —$SO_2$—$R_7$ wherein $R_7$ is a $C_1$-$C_4$ alkyl radical, optionally bearing a hydroxyl radical, or an amino group;
  a —O—$SO_3H$ group;
  a —$SO_3H$ group;
  a —COOH group;
  a radical —$SO_2$—$R_7$ wherein $R_7$ is chosen from a $C_1$-$C_4$ alkyl radical, a phenyl group optionally bearing a hydroxyl radical, an amino group, or an ammonium radical comprising three identical or different radicals chosen from $C_1$-$C_4$ alkyls optionally bearing a carboxylic group in acid or salified form; or
  a —NHCO—$R_8$ or —NH—CO—NH—$R_8$ group, wherein $R_8$ is chosen from a phenyl group or a $C_1$-$C_4$ alkyl radical, optionally bearing a carboxylic group;
a benzyl radical or a phenyl radical,
  optionally substituted with at least one group chosen from:
    a $C_1$-$C_4$ alkyl radical optionally bearing at least one hydroxyl radical;
    a hydroxyl radical;
    a $C_1$-$C_4$ alkoxy radical;
    a halogen atom or chlorine;
    an amino radical optionally substituted with one or two $C_1$-$C_4$ alkyl groups optionally bearing a hydroxyl;
    a sulfonic group (—$SO_3H$); or
    a radical —$SO_2$—$R_9$ wherein $R_9$ is a $C_1$-$C_4$ alkyl radical, optionally bearing a hydroxyl radical or an amino group,
  with the proviso that two radicals borne by adjacent carbon atoms may form, together with the carbon atoms, a 6-membered heterocycle; the heterocycle comprising one or two endocyclic oxygen atoms;
two alkyl radicals $R_6$, which may form, together with the nitrogen atom that bears them, a saturated or unsaturated 5- to 7-membered heterocycle, the heterocycle optionally comprising another endocyclic group having a heteroatom, —O—, —S—, or —$NR_{10}$, wherein $R_{10}$ is chosen from a hydrogen atom or a $C_1$-$C_4$ alkyl radical optionally substituted with a hydroxyl group;
the heterocycle being optionally fused with a phenyl nucleus;
the heterocycle being optionally substituted on one of its carbon atoms with a group chosen from: a $C_1$-$C_4$ alkyl radical optionally bearing a hydroxyl radical;
an amino radical optionally substituted with one or two identical or different radicals $R_{11}$ chosen from a $C_1$-$C_4$ alkyl radical optionally bearing a hydroxyl radical; or an amino radical optionally substituted with one or two identical or different $C_1$-$C_4$ alkyl radicals, wherein two of the radicals $R_{11}$ may form a 5- to 6-membered heterocycle optionally comprising another endocyclic heteroatom, —O—, —S—, or —$NR_{12}$, wherein $R_{12}$ is chosen from a hydrogen atom or a $C_1$-$C_4$ alkyl radical; or a radical

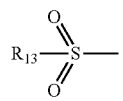

wherein $R_{13}$ is chosen from a $C_1$-$C_4$ alkyl radical or a phenyl radical;
with the proviso that if $R_1$ is a hydroxyl radical, then at least one of the groups $R_4$ or $R_6$ is not hydrogen; or ii) compounds of formula (II), the addition salts thereof, solvates thereof, or mixtures thereof:

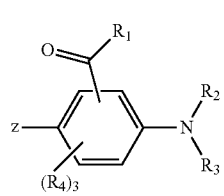

(II)

wherein:
Z is chosen from a hydroxyl group or an amino group optionally substituted with one or two $C_1$-$C_4$ alkyl radicals, which may be identical or different;
$R_1$ is chosen from:
  a hydroxyl radical,
  an amino radical —$NR_{11}R_{12}$, wherein $R_{11}$ and $R_{12}$, which may be identical or different, are chosen from:
    a hydrogen atom;
    a $C_1$-$C_{20}$ alkyl radical, optionally bearing at least one group chosen from:
      a hydroxyl, $C_1$-$C_{15}$ alkoxy, or phenoxy group,
      a —COOH group;
      a —$SO_3H$ group;
      a cyano group;
      a ($C_1$-$C_4$)alkylcarbonyl amino (or ($C_2$-$C_4$)acylamino) group, or mono- or di-($C_1$-$C_4$)alkylaminocarbonyl;
      an amino, optionally substituted with one or two $C_1$-$C_4$ alkyl radicals, which may be identical or different;
      a saturated or unsaturated, aromatic or non-aromatic heterocycle having from 5 to 7 ring members, optionally containing from 1 to 3 endocyclic heteroatoms chosen from nitrogen, oxygen or sulfur, the nitrogen optionally bearing a hydrogen or a $C_1$-$C_4$ alkyl; or
      a $C_6$-$C_{10}$ aryl radical comprising an aromatic nucleus, or two fused aromatic nuclei, the aryl radical being optionally substituted with at least one $C_1$-$C_4$ alkyl, hydroxyl, $C_1$-$C_4$ alkoxy, or trifluoromethyl radical,
    a $C_6$-$C_{10}$ aryl radical comprising an aromatic nucleus optionally fused to another aromatic or heteroaromatic nucleus, wherein the heteroatom is nitrogen, the aryl radical being optionally substituted with at least one group chosen from $C_1$-$C_4$ alkyl, hydroxyl, $C_1$-$C_4$ alkoxy, cyano, trifluoromethyl, halogen, ($C_1$-$C_4$)alkylcarbonylamino, amino, aminosulfonyl, $C_2$-$C_4$ alkynyl, or $NH_2$—C($=NH_2$)—;

a saturated or unsaturated, aromatic or non-aromatic heterocycle having from 5 to 6 ring members, comprising from one to four heteroatoms, nitrogen, or oxygen;

with the proviso that the $R_{11}$ and $R_{12}$ radicals optionally form, together with the nitrogen atom to which they are attached, a heterocycle having from 5 to 7 ring members, optionally fused to a $C_6$ aromatic nucleus, which is cationic or non-cationic, saturated or unsaturated, and aromatic or non-aromatic, optionally containing one endocyclic additional heteroatom chosen from nitrogen, oxygen, or sulfur; the nitrogen optionally bearing one or two $C_1$-$C_4$ alkyls, which may be identical or different, the alkyl group optionally bearing an —$SO_3H$ group; the heterocycle being optionally substituted on at least one of its carbon atoms with one or two groups, which may be identical or different, chosen from a $C_1$-$C_4$ alkyl radical optionally bearing a hydroxyl radical, a hydroxyl radical, an aminocarbonyl radical or a mono- or di-($C_1$-$C_4$) alkylaminocarbonyl radical;

$R_2$ and $R_3$, which may be identical or different, are chosen from:

a hydrogen atom;

a linear $C_1$-$C_{10}$, branched $C_3$-$C_{10}$, or cyclic $C_5$-$C_{10}$ alkyl radical; the alkyl radical being optionally substituted with at least one group chosen from ($C_1$-$C_4$)alkylthio (RS-), cyano, hydroxyl, $C_1$-$C_4$ alkoxy, amino optionally substituted with one or two $C_1$-$C_4$ alkyl radicals which may be identical or different, a mono- or di-($C_1$-$C_4$)alkylaminocarbonyl radical, a saturated, unsaturated or aromatic heterocycle having from 5 to 7 ring members, comprising at least one endocyclic heteroatom chosen from nitrogen, oxygen, or sulfur, the nitrogen atom optionally bearing a $C_1$-$C_4$ alkyl radical;

a saturated or unsaturated, aromatic or non-aromatic $C_5$-$C_{10}$ heterocyclic radical comprising at least one heteroatom or nitrogen, the nitrogen atom optionally bearing a hydrogen or a $C_1$-$C_4$ alkyl radical;

a $C_6$-$C_{10}$ (hetero)aryl radical optionally comprising at least one endocyclic heteroatom; said radical being optionally substituted with one or two $C_1$-$C_4$ alkyl radicals, one or two $C_1$-$C_4$ alkoxy groups, or one or two amino groups optionally substituted with one or two $C_1$-$C_4$ alkyl groups, which may be identical or different; with the provisio that two substituents borne by adjacent carbon atoms of the (hetero)aryl radical may form an aromatic or non-aromatic, fused ring or heterocycle comprising from 5 to 6 ring members, optionally comprising one or two endocyclic heteroatoms, oxygen, or nitrogen;

with the proviso that the $R_2$ and $R_3$ radicals optionally form, together with the nitrogen atom to which they are connected, a saturated or unsaturated, aromatic or non-aromatic heterocycle having from 5 to 7 ring members, optionally containing from 1 to 4 endocyclic additional heteroatoms, which may be identical or different, chosen from nitrogen, oxygen or sulfur, or containing a carbonyl group; the nitrogen optionally bearing one or two $C_1$-$C_4$ alkyl groups, which may be identical or different; wherein the heterocycle is optionally fused to an aromatic nucleus or to a saturated $C_5$-$C_7$ ring, the heterocycle being optionally substituted, on one of the carbon atoms with one or two groups, which may be identical or different, chosen from $C_1$-$C_4$ alkyl optionally bearing a hydroxyl, $C_1$-$C_4$ alkoxy, hydroxyl, amino optionally substituted with one or two radicals which may be identical or different, aminocarbonyl, or mono- or di-($C_1$-$C_4$)alkylaminocarbonyl;

$R_4$, which may be identical or different, is chosen from:

a hydrogen atom;

a $C_1$-$C_{20}$ alkyl or $C_2$-$C_6$ alkenyl; the alkyl or alkenyl being optionally substituted with at least one amino group which is unsubstituted or substituted with one or two $C_1$-$C_4$ alkyl groups which may be identical or different, hydroxyl, $C_1$-$C_4$ alkoxy, cyano, —COOH, ($C_1$-$C_4$) alkylcarbonyl, trifluoromethyl, a saturated or unsaturated (hetero)cycle having from 5 to 7 ring members, optionally comprising one or two heteroatoms, nitrogen or oxygen, wherein the nitrogen optionally bears a $C_1$-$C_4$ alkyl group;

a saturated or unsaturated cycle or heterocycle having 5 to 7 ring members, optionally comprising one or two heteroatoms, nitrogen, or oxygen; wherein the nitrogen optionally bears a hydrogen atom or a $C_1$-$C_4$ alkyl group; wherein the cycle or heterocycle optionally comprises an endocyclic carbonyl group, wherein the cycle or heterocycle is optionally substituted with a hydroxyl group;

a —COOH group;

a —$SO_3H$ group;

halogens, chlorine, fluorine, or bromine;

hydroxyl, $C_1$-$C_4$ alkoxy optionally bearing a carboxylic group, or ($C_1$-$C_4$)alkylthio;

($C_1$-$C_4$)alkylcarbonyl, or $C_2$-$C_4$ acyl, ($C_1$-$C_4$)alkylcarbonylamino, or ($C_2$-$C_4$)acylamino, mono- or di-($C_1$-$C_4$) alkylaminocarbonyl, or am inocarbonyl;

trifluoromethyl;

aryl($C_1$-$C_4$)alkyl;

with the proviso that two $R_4$ groups borne by adjacent carbon atoms may optionally form an aromatic or non-aromatic, fused cycle or heterocycle having from 5 to 6 ring members; the heterocycle optionally comprising at least one heteroatom, chosen from nitrogen, sulfur, or oxygen, wherein the nitrogen atom may optionally bear a $C_1$-$C_4$ alkyl radical; and the cycle or heterocycle may optionally be substituted, on at least one of the carbon atoms, with a $C_1$-$C_4$ alkyl radical;

wherein, if Z and $R_1$ each represent a hydroxyl group, then at most two $R_4$ groups represent hydrogen atoms;

or mixtures thereof;

(c) at least one chemical oxidizing agent other than atmospheric oxygen; and (d) at least one metal catalyst.

2. A method for dyeing keratin fibers comprising at least one metal catalyst and a composition (A) comprising:

(a) at least one fatty substance, the fatty substance present in an amount of at least 10% by weight, relative to the total weight of the composition;

(b) at least one oxidation base chosen from:

i) compounds of formula (I), the addition salts thereof, solvates thereof, or mixtures thereof:

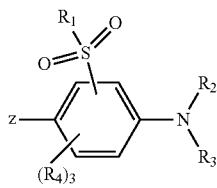 (I)

wherein:
R₁ is chosen from:
a hydroxyl radical,
a $C_1$-$C_{10}$ alkyl radical optionally bearing at least one hydroxyl, $C_1$-$C_4$ alkoxy, —O—SO₃H, —SO₃H, —COOH, halo group, or fluoro,
an amino radical optionally substituted with one or two identical or different groups, chosen from:
a $C_1$-$C_{20}$ linear or $C_3$-$C_{20}$ branched or cyclic alkyl group or a $C_3$-$C_{20}$ linear or branched alkenyl group, the alkyl or alkenyl group optionally bearing at least one hydroxyl or $C_1$-$C_4$ alkoxy radical optionally substituted with a hydroxyl group, an amino optionally substituted with one or two identical or different $C_1$-$C_4$ alkyl groups, pyridyl, furyl, or combinations thereof; the alkyl or alkenyl group optionally forming, together with the nitrogen atom that bears them, a saturated or unsaturated 5- to 7-membered heterocycle optionally comprising one or two identical or different additional endocyclic heteroatoms, chosen from nitrogen, oxygen or sulfur, the heterocycle being optionally substituted on a carbon or nitrogen atom with at least one $C_1$-$C_4$ alkyl radical, and the heterocycle being optionally fused to a phenyl nucleus;
a R'SO₂— group wherein R' is chosen from a $C_1$-$C_4$ alkyl or phenyl radical;
benzyl (C₆H₆—CH₂—), phenyl, or naphthyl groups optionally substituted with at least one $C_1$-$C_4$ alkyl group; trifluoromethyl or hydroxyl groups; a $C_1$-$C_{20}$ alkoxy group; an amino group; a sulfonic (—SO₃H) group; a halogen atom, or chlorine; or
a saturated, unsaturated, or aromatic 5- or 6-membered heterocycle comprising one to three identical or different endocyclic heteroatoms, nitrogen, or sulfur,
a phenyl or benzyl radical, optionally substituted with at least one radical chosen from $C_1$-$C_6$ alkyl, $C_1$-$C_{20}$ alkoxy, hydroxyl, amino, trifluoromethyl, a ($C_1$-$C_4$) alkylamido (alk-CONH—) groups, a sulfonic (—SO₃H) group, a halogen atom, or chlorine;
R₂ and R₃, which may be identical or different, are chosen from a hydrogen atom or a $C_1$-$C_4$ alkyl radical,
R₄, which may be identical or different, is chosen from a hydrogen atom, a $C_1$-$C_4$ alkyl radical, a $C_1$-$C_4$ alkoxy radical, a carboxylic (—COOH) group, a sulfonic (—SO₃H) group, a ($C_1$-$C_4$)alkyl($C_6$)arylsulfonyl (alk-aryl-SO₂—) group, a sulfonamido (NH₂—SO₂—) group, a halogen, chlorine, or bromine,
with the proviso that two radicals R₄ borne by adjacent carbon atoms may optionally form, with the carbon atoms, a saturated, unsaturated or aromatic 6-membered ring, optionally comprising an endocyclic nitrogen atom, the ring being optionally fused to another 6-membered aromatic nucleus or optionally substituted with a ($C_1$-$C_4$)alkylamido (alk-CONH—) or sulfonic (—SO₃H) radical; and Z is chosen from a hydroxyl group or an amino group optionally substituted with one or two identical or different radicals R₆ chosen from:
a linear $C_1$-$C_{10}$ alkyl or branched $C_3$-$C_{10}$ alkyl radical,
the linear $C_1$-$C_{10}$ alkyl or branched $C_3$-$C_{10}$ alkyl radical optionally interrupted with a heteroatom chosen from oxygen, an amino group optionally substituted with a $C_1$-$C_4$ alkyl radical, or an ammonium group substituted with three identical or different $C_1$-$C_4$ alkyl radicals;
the alkyl radical optionally bearing at least one group chosen from:
a hydroxyl radical;
an amino radical optionally substituted with a $C_1$-$C_4$ alkyl group;
an ammonium radical substituted with three identical or different $C_1$-$C_4$ alkyl groups, wherein at least one of the groups is optionally substituted with a —COOH group or a hydroxyl group;
a phenyl optionally bearing a radical —SO₂—R₇ wherein R₇ is a $C_1$-$C_4$ alkyl radical, optionally bearing a hydroxyl radical, or an amino group;
a —O—SO₃H group;
a —SO₃H group;
a —COOH group;
a radical —SO₂—R₇ wherein R₇ is chosen from a $C_1$-$C_4$ alkyl radical, a phenyl group optionally bearing a hydroxyl radical, an amino group, or an ammonium radical comprising three identical or different radicals chosen from $C_1$-$C_4$ alkyls optionally bearing a carboxylic group in acid or salified form; or
a —NHCO—R₈ or —NH—CO—NH—R₈ group, wherein R₈ is chosen from a phenyl group or a $C_1$-$C_4$ alkyl radical, optionally bearing a carboxylic group;
a benzyl radical or a phenyl radical,
optionally substituted with at least one group chosen from:
a $C_1$-$C_4$ alkyl radical optionally bearing at least one hydroxyl radical;
a hydroxyl radical;
a $C_1$-$C_4$ alkoxy radical;
a halogen atom or chlorine;
an amino radical optionally substituted with one or two $C_1$-$C_4$ alkyl groups optionally bearing a hydroxyl;
a sulfonic group (—SO₃H); or
a radical —SO₂—R₉ wherein R₉ is a $C_1$-$C_4$ alkyl radical, optionally bearing a hydroxyl radical or an amino group,
with the proviso that two radicals borne by adjacent carbon atoms may form, together with the carbon atoms, a 6-membered heterocycle; the heterocycle comprising one or two endocyclic oxygen atoms;
two alkyl radicals R₆, which may form, together with the nitrogen atom that bears them, a saturated or unsaturated 5- to 7-membered heterocycle, the heterocycle optionally comprising another endocyclic group having a heteroatom, —O—, —S—, or —NR₁₀, wherein R₁₀ is chosen from a hydrogen atom or a $C_1$-$C_4$ alkyl radical optionally substituted with a hydroxyl group;
the heterocycle being optionally fused with a phenyl nucleus;
the heterocycle being optionally substituted on one of its carbon atoms with a group chosen from: a $C_1$-$C_4$ alkyl radical optionally bearing a hydroxyl radical;

an amino radical optionally substituted with one or two identical or different radicals $R_{11}$ chosen from a $C_1$-$C_4$ alkyl radical optionally bearing a hydroxyl radical; or an amino radical optionally substituted with one or two identical or different $C_1$-$C_4$ alkyl radicals, wherein two of the radicals $R_{11}$ may form a 5- to 6-membered heterocycle optionally comprising another endocyclic heteroatom, —O—, —S—, or —$NR_{12}$, wherein $R_{12}$ is chosen from a hydrogen atom or a $C_1$-$C_4$ alkyl radical; or a radical

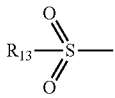

wherein $R_{13}$ is chosen from a $C_1$-$C_4$ alkyl radical or a phenyl radical;

with the proviso that if $R_1$ is a hydroxyl radical, then at least one of the groups $R_4$ or $R_6$ is not hydrogen; or ii) compounds of formula (II), the addition salts thereof, solvates thereof, or mixtures thereof:

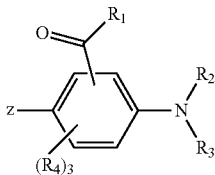

(II)

wherein:

Z is chosen from a hydroxyl group or an amino group optionally substituted with one or two $C_1$-$C_4$ alkyl radicals, which may be identical or different;

$R_1$ is chosen from:
  a hydroxyl radical,
  an amino radical —$NR_{11}R_{12}$, wherein $R_{11}$ and $R_{12}$, which may be identical or different, are chosen from:
    a hydrogen atom;
    a $C_1$-$C_{20}$ alkyl radical, optionally bearing at least one group chosen from:
      a hydroxyl, $C_1$-$C_{15}$ alkoxy, or phenoxy group,
      a —COOH group;
      a —$SO_3H$ group;
      a cyano group;
      a ($C_1$-$C_4$)alkylcarbonyl amino (or ($C_2$-$C_4$)acylamino) group, or mono- or di-($C_1$-$C_4$)alkylaminocarbonyl;
      an amino, optionally substituted with one or two $C_1$-$C_4$ alkyl radicals, which may be identical or different;
      a saturated or unsaturated, aromatic or non-aromatic heterocycle having from 5 to 7 ring members, optionally containing from 1 to 3 endocyclic heteroatoms chosen from nitrogen, oxygen or sulfur, the nitrogen optionally bearing a hydrogen or a $C_1$-$C_4$ alkyl; or
      a $C_6$-$C_{10}$ aryl radical comprising an aromatic nucleus, or two fused aromatic nuclei, the aryl radical being optionally substituted with at least one $C_1$-$C_4$ alkyl, hydroxyl, $C_1$-$C_4$ alkoxy, or trifluoromethyl radical,
      a $C_6$-$C_{10}$ aryl radical comprising an aromatic nucleus optionally fused to another aromatic or heteroaromatic nucleus, wherein the heteroatom is nitrogen, the aryl radical being optionally substituted with at least one group chosen from $C_1$-$C_4$ alkyl, hydroxyl, $C_1$-$C_4$ alkoxy, cyano, trifluoromethyl, halogen, ($C_1$-$C_4$)alkylcarbonylamino, amino, aminosulfonyl, $C_2$-$C_4$ alkynyl, or $NH_2$—C(=$NH_2$)—;
      a saturated or unsaturated, aromatic or non-aromatic heterocycle having from 5 to 6 ring members, comprising from one to four heteroatoms, nitrogen, or oxygen;
    with the proviso that the $R_{11}$ and $R_{12}$ radicals optionally form, together with the nitrogen atom to which they are attached, a heterocycle having from 5 to 7 ring members, optionally fused to a $C_6$ aromatic nucleus, which is cationic or non-cationic, saturated or unsaturated, and aromatic or non-aromatic, optionally containing one endocyclic additional heteroatom chosen from nitrogen, oxygen, or sulfur; the nitrogen optionally bearing one or two $C_1$-$C_4$ alkyls, which may be identical or different, the alkyl group optionally bearing an —$SO_3H$ group; the heterocycle being optionally substituted on at least one of its carbon atoms with one or two groups, which may be identical or different, chosen from a $C_1$-$C_4$ alkyl radical optionally bearing a hydroxyl radical, a hydroxyl radical, an aminocarbonyl radical or a mono- or di-($C_1$-$C_4$) alkylaminocarbonyl radical;

$R_2$ and $R_3$, which may be identical or different, are chosen from:
  a hydrogen atom;
  a linear $C_1$-$C_{10}$, branched $C_3$-$C_{10}$, or cyclic $C_5$-$C_{10}$ alkyl radical; the alkyl radical being optionally substituted with at least one group chosen from ($C_1$-$C_4$)alkylthio (RS-), cyano, hydroxyl, $C_1$-$C_4$ alkoxy, amino optionally substituted with one or two $C_1$-$C_4$ alkyl radicals which may be identical or different, a mono- or di-($C_1$-$C_4$)alkylaminocarbonyl radical, a saturated, unsaturated or aromatic heterocycle having from 5 to 7 ring members, comprising at least one endocyclic heteroatom chosen from nitrogen, oxygen, or sulfur, the nitrogen atom optionally bearing a $C_1$-$C_4$ alkyl radical;
  a saturated or unsaturated, aromatic or non-aromatic $C_5$-$C_{10}$ heterocyclic radical comprising at least one heteroatom or nitrogen, the nitrogen atom optionally bearing a hydrogen or a $C_1$-$C_4$ alkyl radical;
  a $C_6$-$C_{10}$ (hetero)aryl radical optionally comprising at least one endocyclic heteroatom; said radical being optionally substituted with one or two $C_1$-$C_4$ alkyl radicals, one or two $C_1$-$C_4$ alkoxy groups, or one or two amino groups optionally substituted with one or two $C_1$-$C_4$ alkyl groups, which may be identical or different; with the proviso that two substituents borne by adjacent carbon atoms of the (hetero)aryl radical may form an aromatic or non-aromatic, fused ring or heterocycle comprising from 5 to 6 ring members, optionally comprising one or two endocyclic heteroatoms, oxygen, or nitrogen;

with the proviso that the $R_2$ and $R_3$ radicals optionally form, together with the nitrogen atom to which they are connected, a saturated or unsaturated, aromatic or non-aromatic heterocycle having from 5 to 7 ring members, optionally containing from 1 to 4 endocyclic additional heteroatoms, which may be identical or different, chosen from nitrogen, oxygen or sulfur, or containing a carbonyl group; the nitrogen optionally bearing one or two $C_1$-$C_4$ alkyl groups, which may be identical or different; wherein the heterocycle is optionally fused to an aromatic nucleus or to a saturated $C_5$-$C_7$ ring, the heterocycle being optionally substituted, on one of the carbon atoms with one or two groups, which may be identical or different, chosen from $C_1$-$C_4$ alkyl optionally bearing a hydroxyl, $C_1$-$C_4$ alkoxy, hydroxyl, amino optionally substituted with one or two radicals which may be identical or different, aminocarbonyl, or mono- or di-($C_1$-$C_4$)alkylaminocarbonyl;

$R_4$, which may be identical or different, is chosen from:
  a hydrogen atom;
  a $C_1$-$C_{20}$ alkyl or $C_2$-$C_6$ alkenyl; the alkyl or alkenyl being optionally substituted with at least one amino group which is unsubstituted or substituted with one or two $C_1$-$C_4$ alkyl groups which may be identical or different, hydroxyl, $C_1$-$C_4$ alkoxy, cyano, —COOH, ($C_1$-$C_4$) alkylcarbonyl, trifluoromethyl, a saturated or unsaturated (hetero)cycle having from 5 to 7 ring members, optionally comprising one or two heteroatoms, nitrogen or oxygen, wherein the nitrogen optionally bears a $C_1$-$C_4$ alkyl group;
  a saturated or unsaturated cycle or heterocycle having 5 to 7 ring members, optionally comprising one or two heteroatoms, nitrogen, or oxygen; wherein the nitrogen optionally bears a hydrogen atom or a $C_1$-$C_4$ alkyl group; wherein the cycle or heterocycle optionally comprises an endocyclic carbonyl group, wherein the cycle or heterocycle is optionally substituted with a hydroxyl group;
  a —COOH group;
  a —$SO_3H$ group;
  halogens, chlorine, fluorine, or bromine;
  hydroxyl, $C_1$-$C_4$ alkoxy optionally bearing a carboxylic group, or ($C_1$-$C_4$)alkylthio;
  ($C_1$-$C_4$)alkylcarbonyl, or $C_2$-$C_4$ acyl, ($C_1$-$C_4$)alkylcarbonyl amino, or ($C_2$-$C_4$)acylamino, mono- or di-($C_1$-$C_4$) alkylaminocarbonyl, or aminocarbonyl;
  trifluoromethyl;
  aryl($C_1$-$C_4$)alkyl;
  with the proviso that two $R_4$ groups borne by adjacent carbon atoms may optionally form an aromatic or non-aromatic, fused cycle or heterocycle having from 5 to 6 ring members; the heterocycle optionally comprising at least one heteroatom, chosen from nitrogen, sulfur, or oxygen, wherein the nitrogen atom may optionally bear a $C_1$-$C_4$ alkyl radical; and the cycle or heterocycle may optionally be substituted, on at least one of the carbon atoms, with a $C_1$-$C_4$ alkyl radical;
  wherein, if Z and $R_1$ each represent a hydroxyl group, then at most two $R_4$ groups represent hydrogen atoms;
or mixtures thereof; and
  (c) at least one chemical oxidizing agent other than atmospheric oxygen.

3. The method according to claim 2, wherein the at least one oxidation base is chosen from the compounds of formula (I) wherein:
  $R_1$ represents a hydroxyl radical;
  $R_2$ and $R_3$, which may be identical or different, are chosen from a hydrogen atom or a $C_1$-$C_4$ alkyl radical;
  $R_4$, which may be identical or different, is chosen from a hydrogen atom, a $C_1$-$C_4$ alkyl radical, a $C_1$-$C_4$ alkoxy radical, a carboxylic (—COOH) group, a sulfonic (—$SO_3H$) group, a halogen, chlorine, or bromine;
  with the proviso that two radicals $R_4$ borne by adjacent carbon atoms may optionally form, together with the carbon atoms, a saturated, unsaturated or aromatic 6-membered ring, optionally comprising an endocyclic nitrogen atom, the ring being optionally fused to another 6-membered aromatic nucleus and/or optionally substituted with a sulfonic (—$SO_3H$) radical; and
  Z is chosen from a hydroxyl group or an amino group optionally substituted with one or two identical or different radicals $R_6$, chosen from:
    a linear $C_1$-$C_{10}$ alkyl or branched $C_3$-$C_{10}$ alkyl radical, the linear $C_1$-$C_{10}$ alkyl or branched $C_3$-$C_{10}$ alkyl radical optionally interrupted with a heteroatom chosen from oxygen or an amino group optionally substituted with a $C_1$-$C_4$ alkyl radical;
    the alkyl radical optionally bearing at least one group chosen from:
      a hydroxyl radical; or
      an amino radical optionally substituted with a $C_1$-$C_4$ alkyl group,
    wherein two alkyl radicals $R_6$ may form, together with the nitrogen atom that bears them, a saturated or unsaturated 5- to 7-membered heterocycle, the heterocycle optionally comprising another endocyclic group having a heteroatom, —O—, —S—, or —$NR_{10}$, wherein $R_{10}$ is chosen from a hydrogen atom or a $C_1$-$C_4$ alkyl radical.

4. The method according to claim 2, wherein the at least one oxidation base is chosen from the compounds of formula (I) wherein:
  $R_1$ is an amino radical optionally substituted with one or two identical or different groups chosen from:
    a $C_1$-$C_{20}$ linear or $C_3$-$C_{20}$ branched or cyclic alkyl group or a $C_3$-$C_{20}$ linear or branched alkenyl group, the alkyl or alkenyl group optionally bearing at least one hydroxyl or $C_1$-$C_4$ alkoxy radical optionally substituted with a hydroxyl group, an amino optionally substituted with one or two identical or different $C_1$-$C_4$ alkyl groups, pyridyl, furyl, or combinations thereof; the alkyl or alkenyl group optionally forming, together with the nitrogen atom that bears it, a saturated or unsaturated 5- to 7-membered heterocycle optionally comprising one or two identical or different additional endocyclic heteroatoms chosen from nitrogen, oxygen, or sulfur, the heterocycle being optionally substituted on a carbon or nitrogen atom with at least one $C_1$-$C_4$ alkyl radical; and the heterocycle being optionally fused to a phenyl nucleus;
    a $R'SO_2$— group wherein $R'$ is chosen from a $C_1$-$C_4$ alkyl or phenyl radical;
    benzyl ($C_6H_6$—$CH_2$—), phenyl, or naphthyl groups optionally substituted with at least one $C_1$-$C_4$ alkyl group; trifluoromethyl or hydroxyl groups; $C_1$-$C_{20}$ alkoxy group; an amino group; a sulfonic (—$SO_3H$) group; a halogen atom; or chlorine; or
    a saturated, unsaturated, or aromatic 5- or 6-membered heterocycle comprising one to three identical or different endocyclic heteroatoms, nitrogen, or sulfur;
  $R_2$ and $R_3$, which may be identical or different, are chosen from a hydrogen atom or a $C_1$-$C_4$ alkyl radical;
  $R_4$, which may be identical or different, is chosen from a hydrogen atom or a sulfonamido ($NH_2$—$SO_2$—) group; and
  Z is chosen from a hydroxyl group or an amino group optionally substituted with one or two identical or different radicals $R_6$, chosen from:

a linear $C_1$-$C_{10}$ alkyl or branched $C_3$-$C_{10}$ alkyl radical,
the linear $C_1$-$C_{10}$ alkyl or branched $C_3$-$C_{10}$ alkyl radical optionally bearing at least one group chosen from:
a hydroxyl radical;
an amino radical optionally substituted with a $C_1$-$C_4$ alkyl group;
a —$SO_3H$ group; or
a radical —$SO_2$—$R_7$ wherein $R_7$ is chosen from a $C_1$-$C_4$ alkyl radical or a phenyl radical;
a benzyl radical or a phenyl radical,
wherein the benzyl radical or phenyl radical is optionally substituted with at least one group chosen from:
a $C_1$-$C_4$ alkyl radical optionally bearing at least one hydroxyl radical;
a hydroxyl radical;
a $C_1$-$C_4$ alkoxy radical; or
a halogen atom or chlorine;
with the proviso that two radicals borne by adjacent carbon atoms may form, together with the carbon atoms, a 6-membered heterocycle; the heterocycle comprising one or two endocyclic oxygen atoms;
two alkyl radicals $R_6$, which may form, together with the nitrogen atom that bears them, a saturated or unsaturated 5- to 7-membered heterocycle, the heterocycle optionally comprising another endocyclic group having a heteroatom, —O—, or —$NR_{10}$, $R_{10}$ chosen from a hydrogen atom or a $C_1$-$C_4$ alkyl radical optionally substituted with a hydroxyl group; the heterocycle being optionally fused with a phenyl nucleus; or
the heterocycle being optionally substituted on one of its carbon atoms with a $C_1$-$C_4$ alkyl radical, or a radical

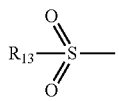

wherein $R_{13}$ is chosen from a $C_1$-$C_4$ alkyl radical or a phenyl radical.

5. The method according to claim 2, wherein the at least one oxidation base is chosen from the compounds of formula (I) wherein:

$R_1$ is chosen from:
a $C_1$-$C_{10}$ alkyl radical optionally bearing at least one hydroxyl, $C_1$-$C_4$ alkoxy, —O—$SO_3H$ group, —$SO_3H$ group, —COOH group, halo group, or fluoro; or
a phenyl or benzyl radical, optionally substituted with at least one radical chosen from $C_1$-$C_6$ alkyl, $C_1$-$C_{20}$ alkoxy, hydroxyl, amino, trifluoromethyl, a ($C_1$-$C_4$) alkylamido (alk-CONH—) group, a sulfonic (—$SO_3H$) group, or a halogen atom;
$R_2$ and $R_3$, which may be identical or different, are chosen from a hydrogen atom or a $C_1$-$C_4$ alkyl radical;
$R_4$, which may be identical or different, is chosen from a hydrogen atom, a $C_1$-$C_4$ alkyl radical, a $C_1$-$C_4$ alkoxy radical, a halogen, chlorine, or bromine; and
Z is chosen from a hydroxyl group or an amino group optionally substituted with one or two identical or different radicals $R_6$ chosen from:

a linear $C_1$-$C_{10}$ alkyl or branched $C_3$-$C_{10}$ alkyl radical,
the linear $C_1$-$C_{10}$ alkyl or branched $C_3$-$C_{10}$ alkyl radical optionally interrupted with a heteroatom chosen from oxygen, an amino group optionally substituted with a $C_1$-$C_4$ alkyl radical, or an ammonium group substituted with three identical or different alkyl radicals;
the alkyl radicals optionally bearing at least one group chosen from:
a hydroxyl radical;
an amino radical optionally substituted with a $C_1$-$C_4$ alkyl group;
an ammonium radical substituted with three identical or different $C_1$-$C_4$ alkyl groups, wherein at least one of these groups is optionally substituted with a —COOH or hydroxyl group;
a —O—$SO_3H$ group;
a —$SO_3H$ group;
a —COOH group;
a radical —$SO_2$—$R_7$ wherein $R_7$ is chosen from a $C_1$-$C_4$ alkyl radical optionally bearing a hydroxyl radical, an amino group, or an ammonium radical comprising three identical or different radicals chosen from $C_1$-$C_4$ alkyls optionally bearing a hydroxyl or carboxylic group in acid or salified form; or
a —NHCO—$R_8$ or —NH—CO—NH—$R_8$ group, wherein $R_8$ is chosen from a phenyl group or a $C_1$-$C_4$ alkyl radical, optionally bearing a carboxylic group,
a benzyl radical or a phenyl radical,
optionally substituted with at least one group chosen from:
a hydroxyl radical;
a $C_1$-$C_4$ alkoxy radical;
an amino radical optionally substituted with one or two $C_1$-$C_4$ alkyl groups optionally bearing a hydroxyl;
a sulfonic group (—$SO_3H$); or
a radical —$SO_2$-$R_9$ wherein $R_9$ is a $C_1$-$C_4$ alkyl radical, optionally bearing a hydroxyl radical, or an amino group,
with the proviso that two alkyl radicals $R_6$ may form, together with the nitrogen atom that bears them, a saturated or unsaturated 5- to 7-membered heterocycle optionally comprising another endocyclic group with a heteroatom, —O— or —$NR_{10}$, wherein $R_{10}$ is chosen from a hydrogen atom or a $C_1$-$C_4$ alkyl radical;
the heterocycle being optionally substituted on one of its carbon atoms with a $C_1$-$C_4$ alkyl radical optionally bearing a hydroxyl radical; an amino radical optionally substituted with one or two identical or different radicals $R_{11}$ chosen from a $C_1$-$C_4$ alkyl radical; wherein two radicals $R_{11}$ may form a 5- to 6-membered heterocycle optionally comprising another endocyclic heteroatom, —O—, —S—, or —$NR_{12}$, wherein $R_{12}$ is chosen from a hydrogen atom or a $C_1$-$C_4$ alkyl radical; or
a radical

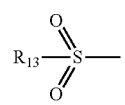

wherein $R_{13}$ is a $C_1$-$C_4$ alkyl radical.

6. The method according to claim 2, wherein the at least one oxidation base is chosen from the compounds of formula (I) wherein $R_2$ and $R_3$ are each a hydrogen atom.
7. The method according to claim 2, wherein the at least one oxidation base of formula (I) is chosen from the following compounds, addition salts thereof, solvates thereof or mixtures thereof:
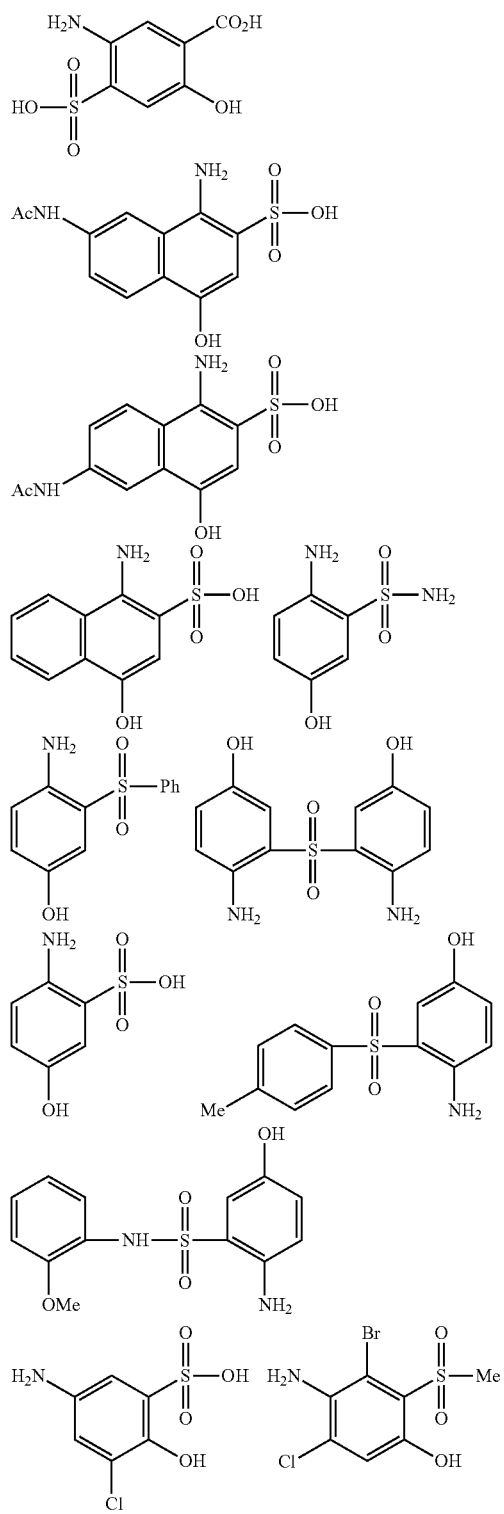
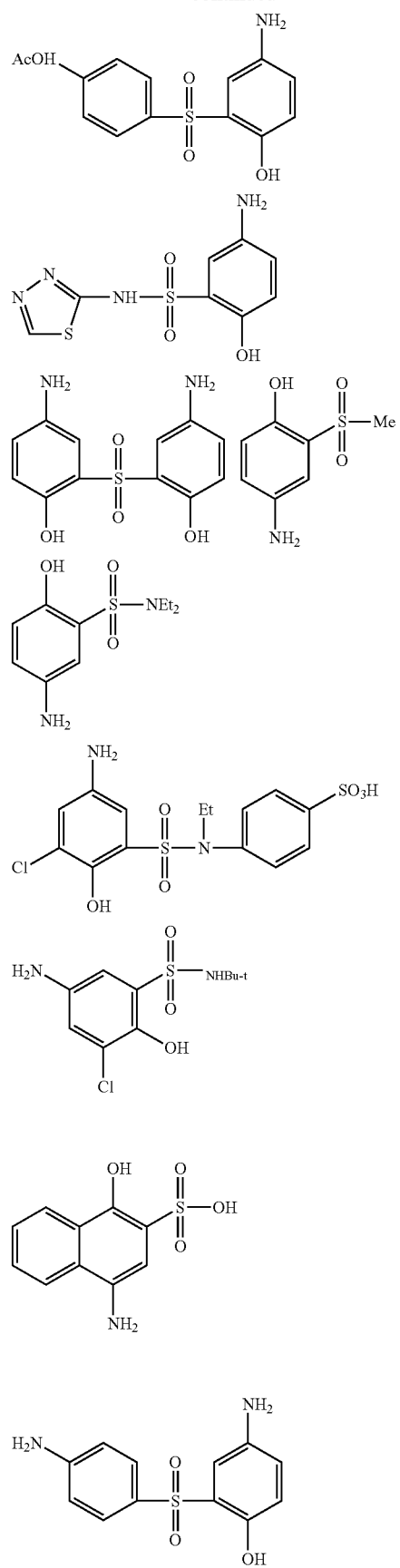
-continued

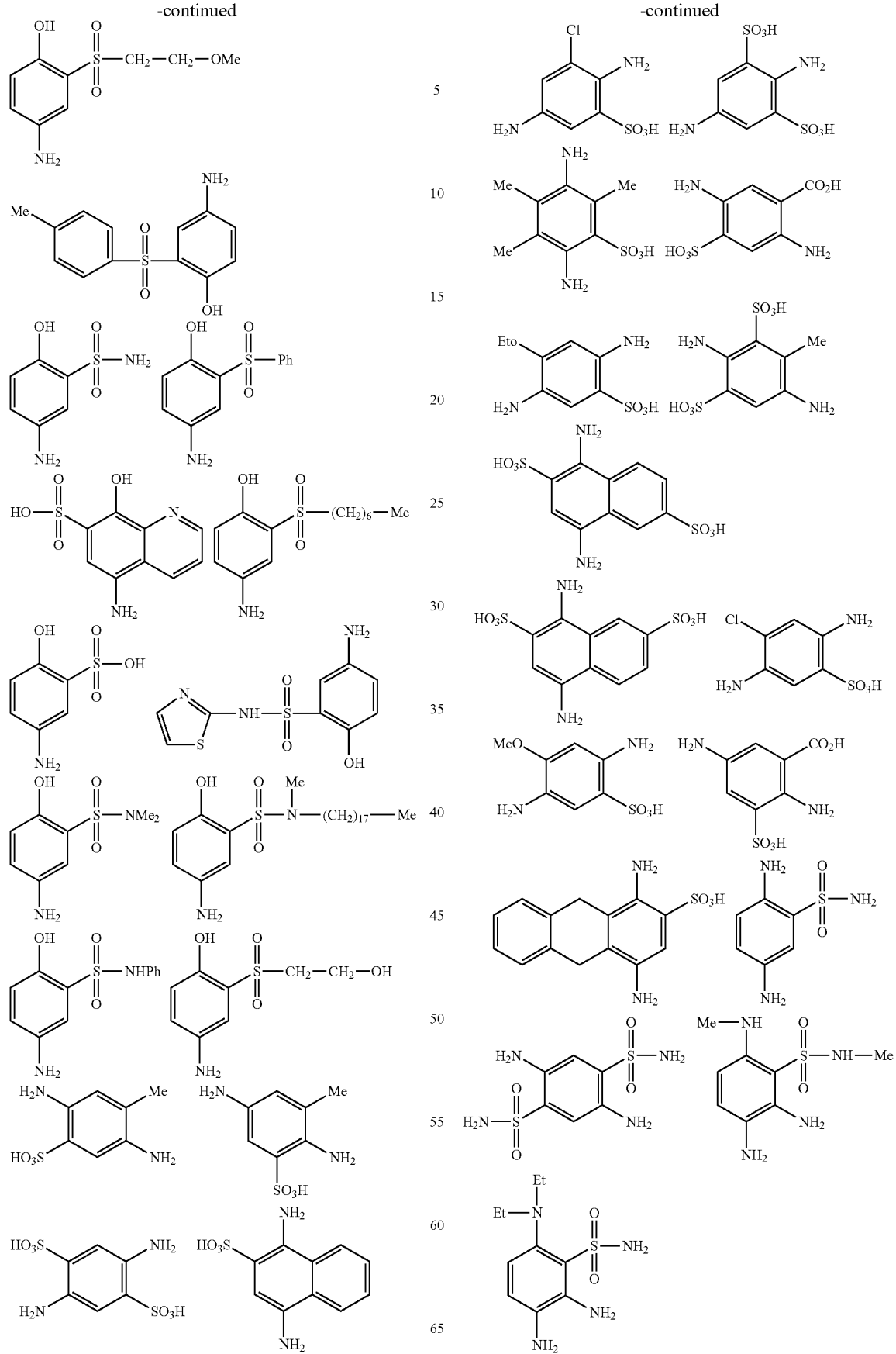

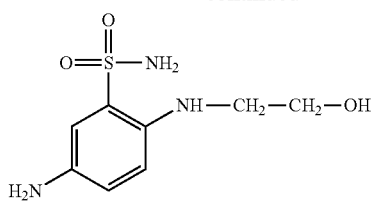
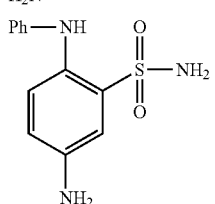
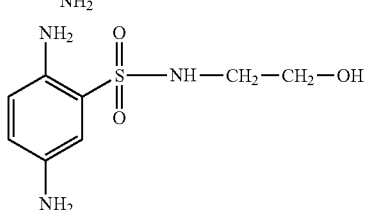
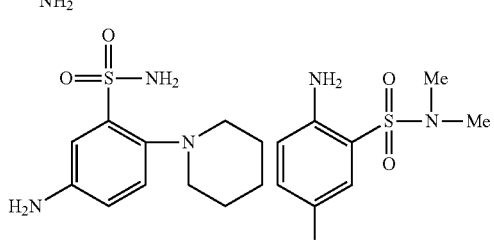
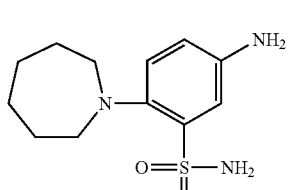
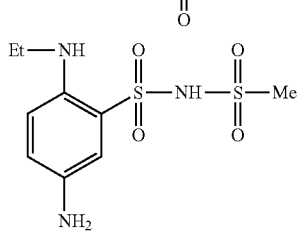
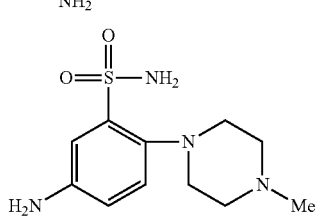
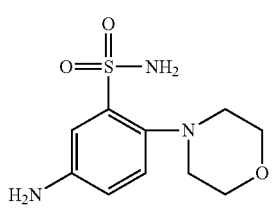
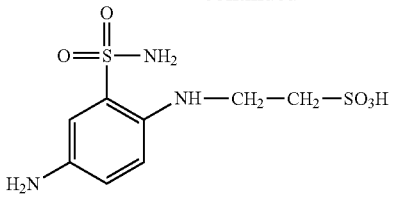
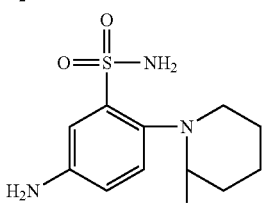
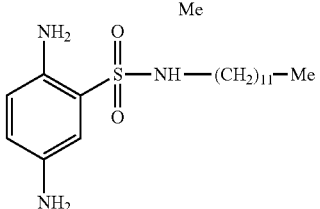
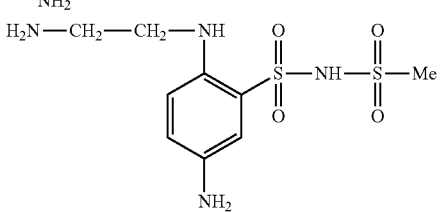
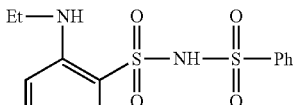
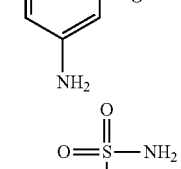
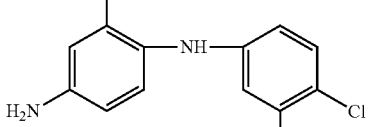
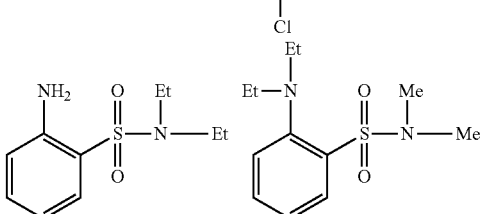
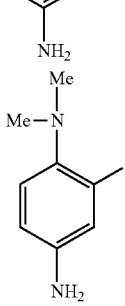

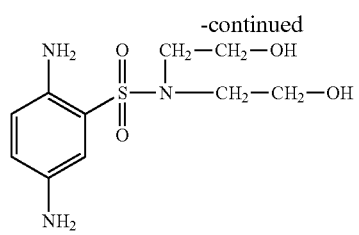
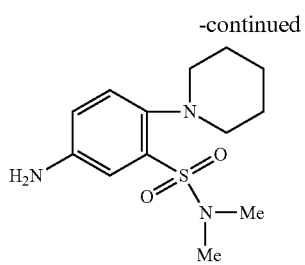
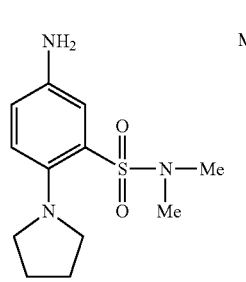
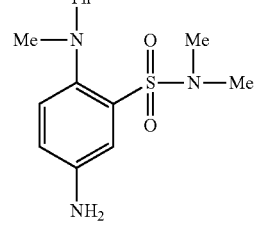
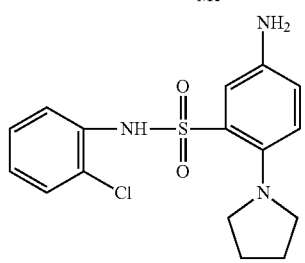
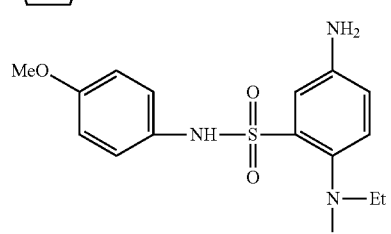
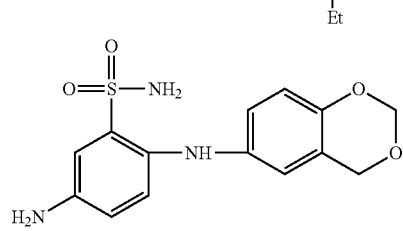
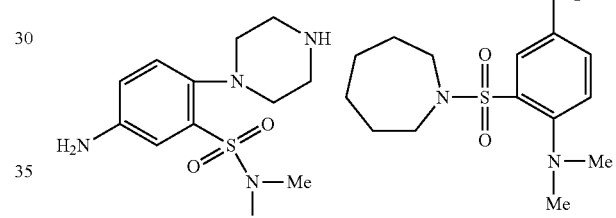
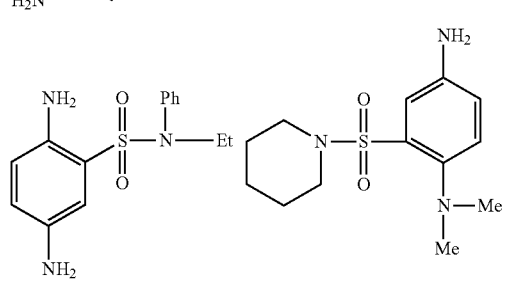
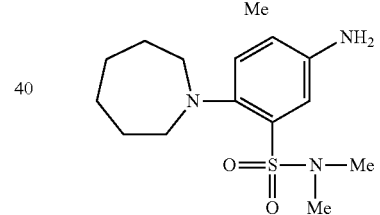
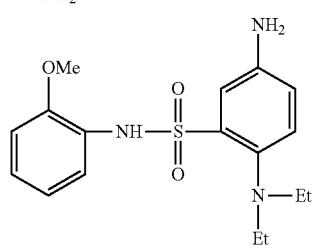
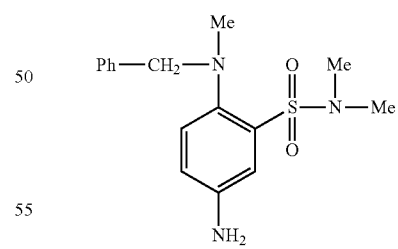
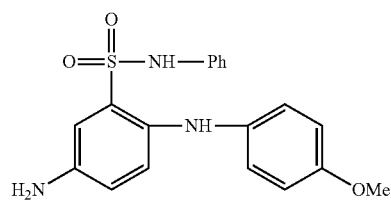
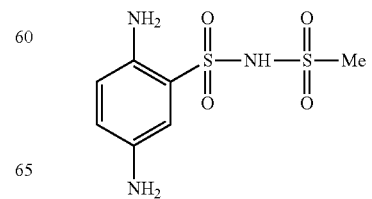

93
-continued
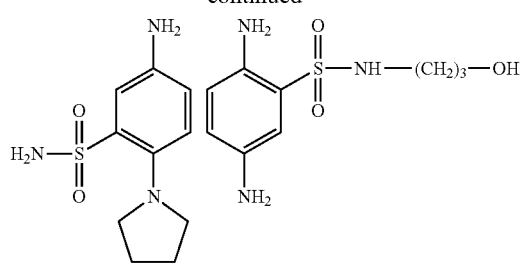
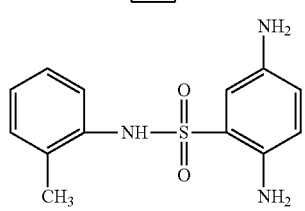
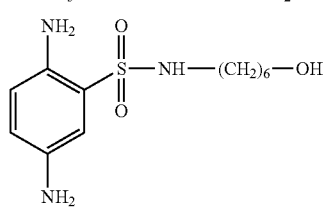
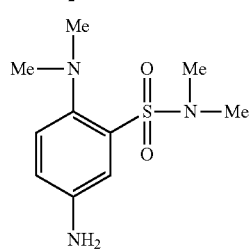
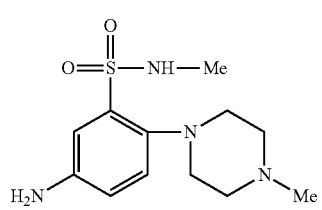
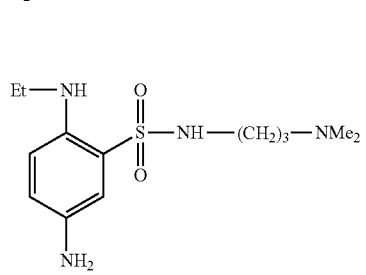
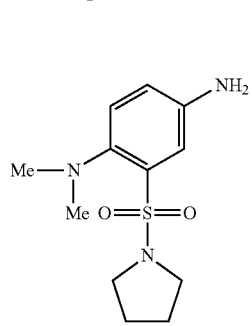
94
-continued
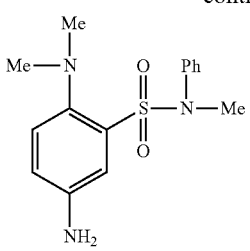
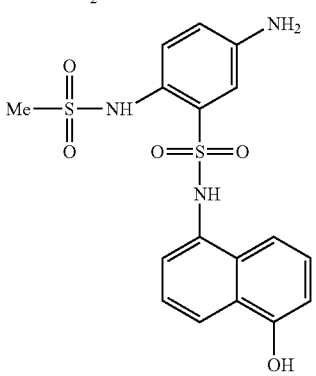
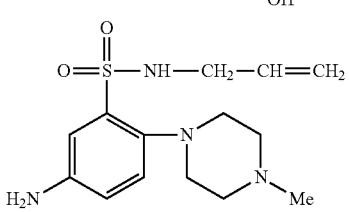
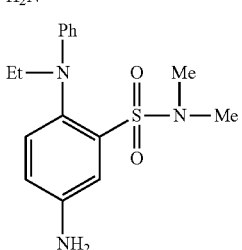
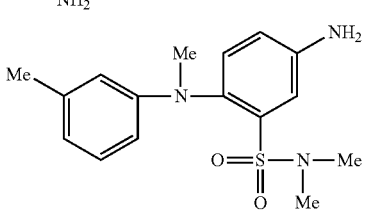
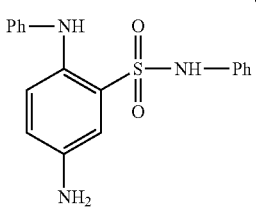
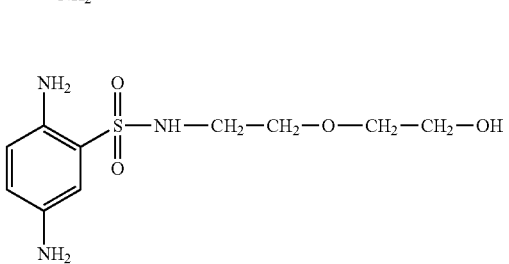

-continued
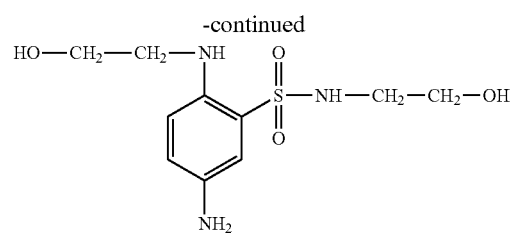
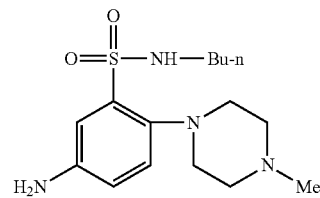
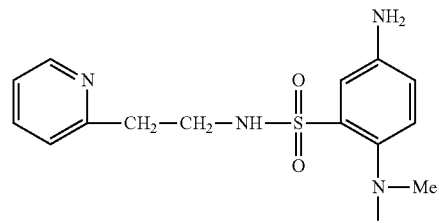
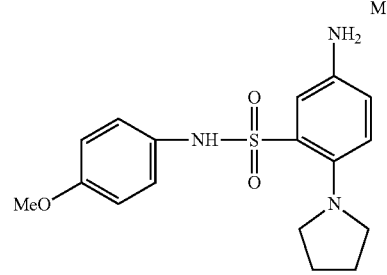
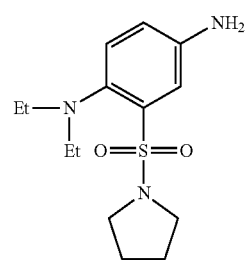
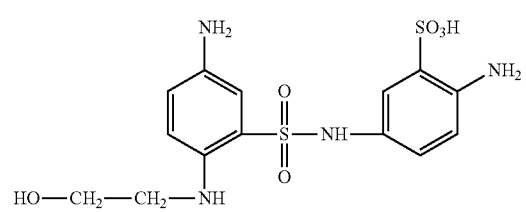
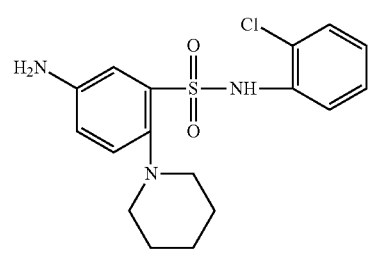
-continued
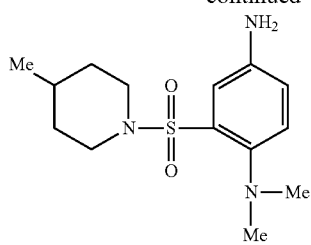
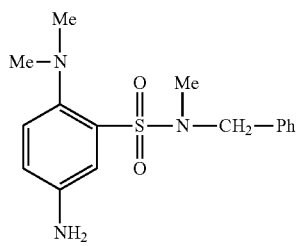
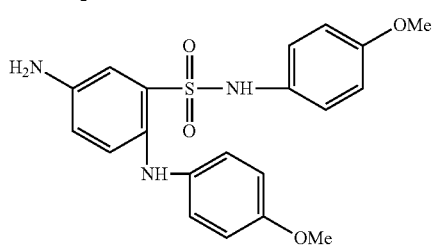
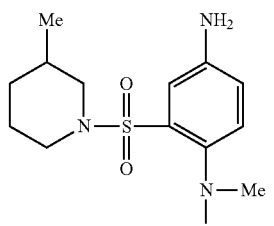
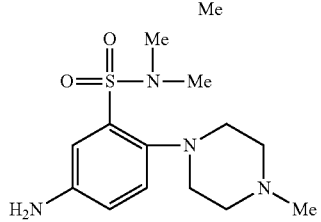
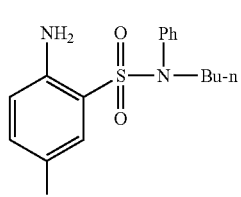
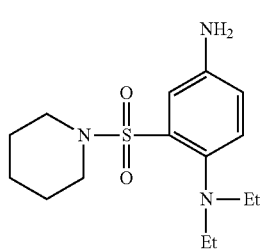

97
-continued
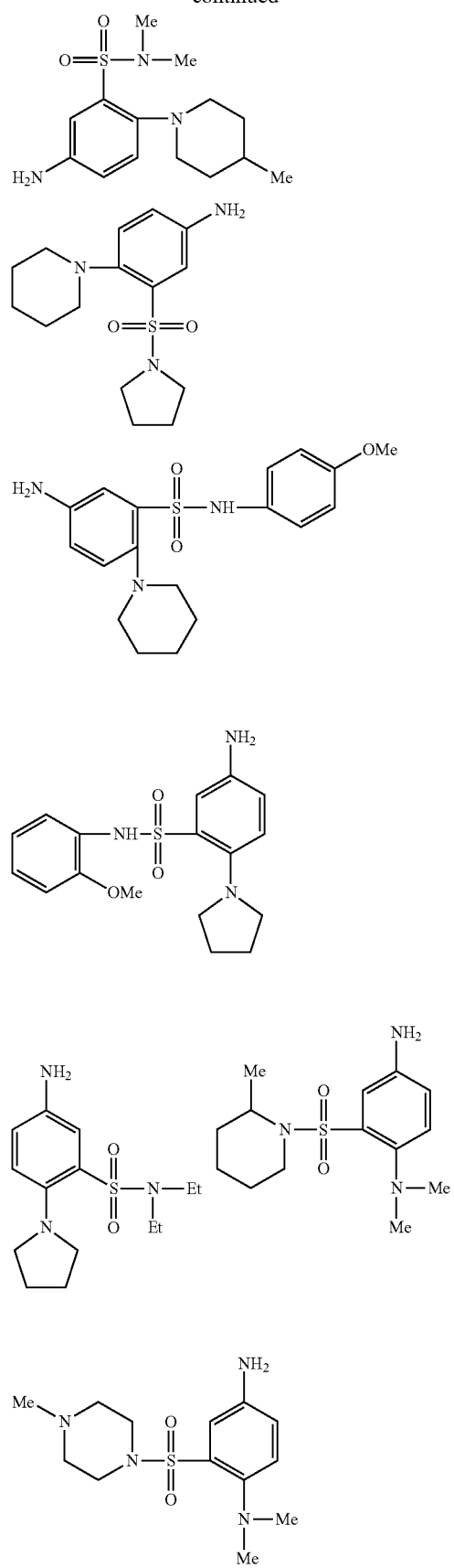
98
-continued
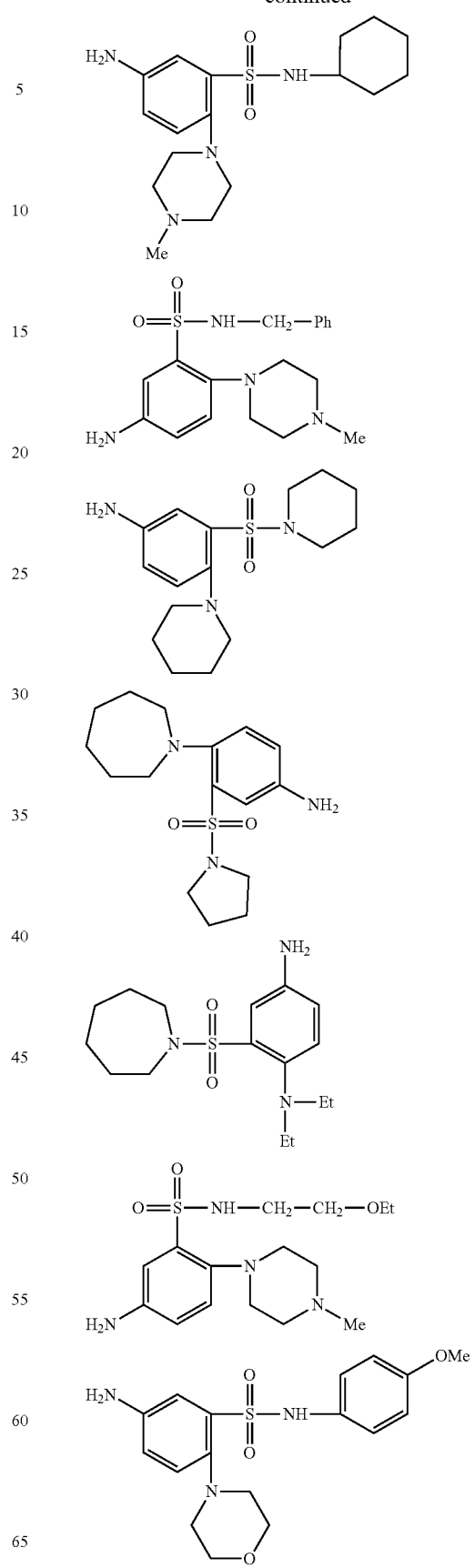

-continued
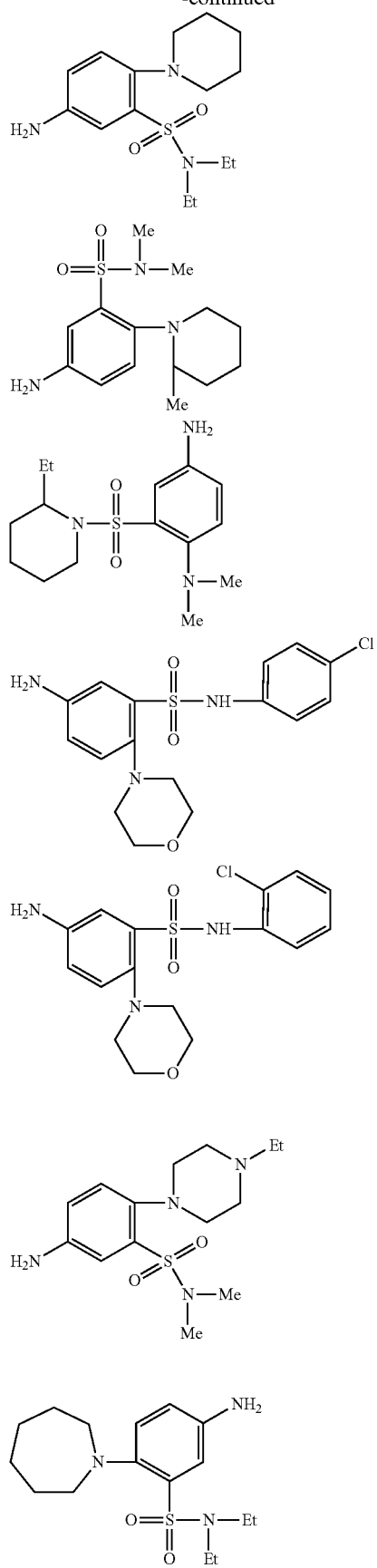
-continued
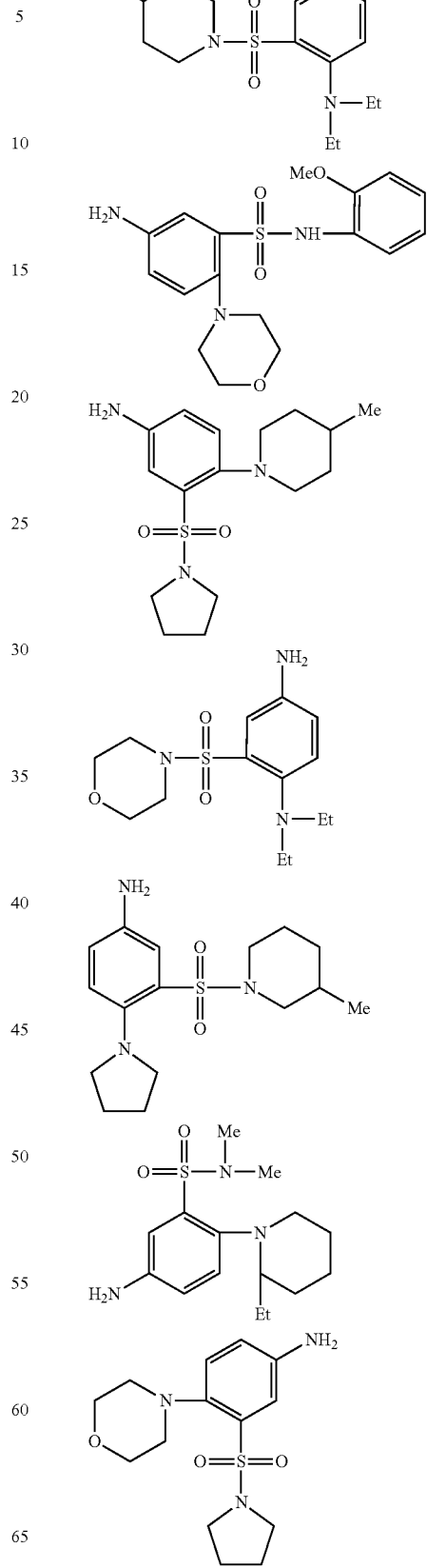

101
-continued
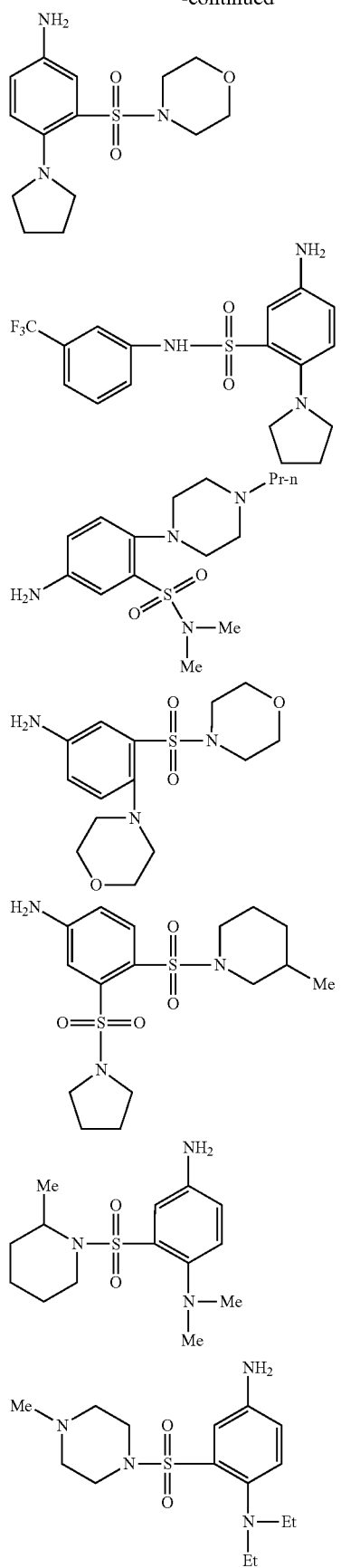
102
-continued
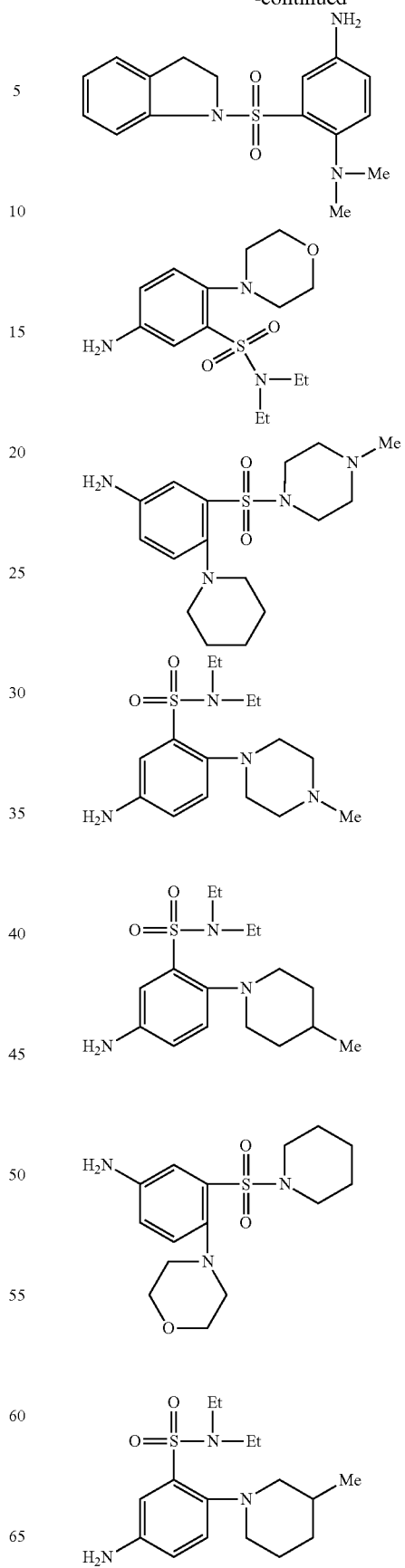

-continued
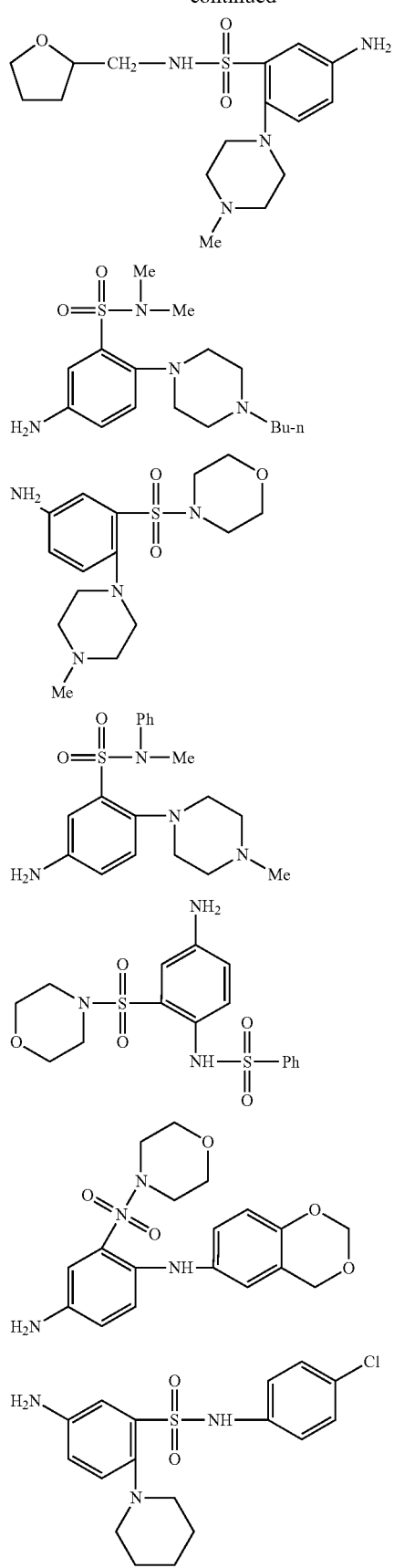
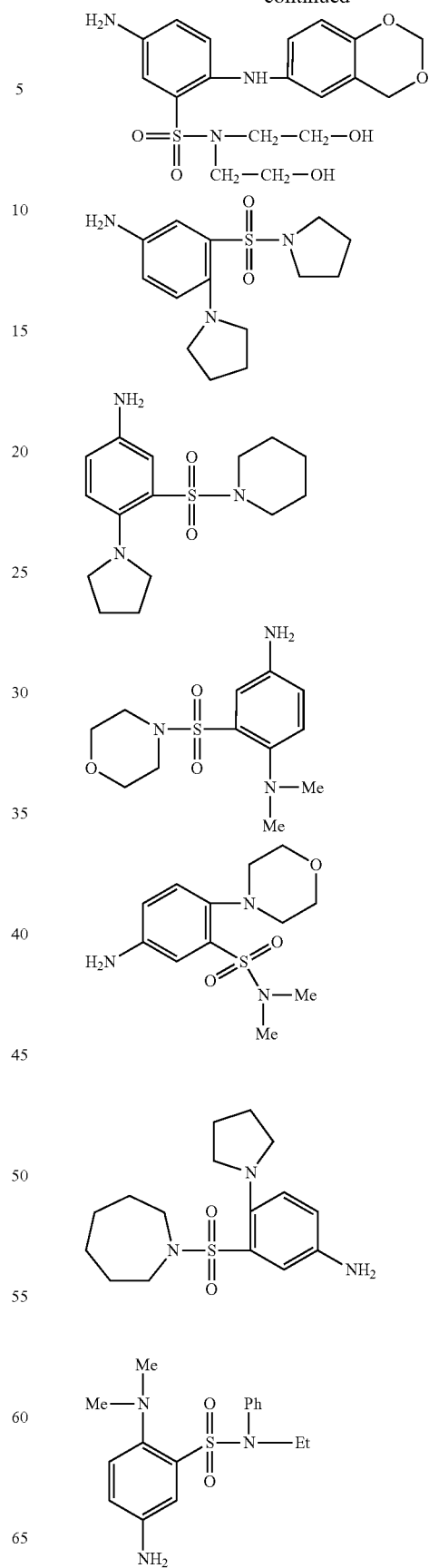

-continued
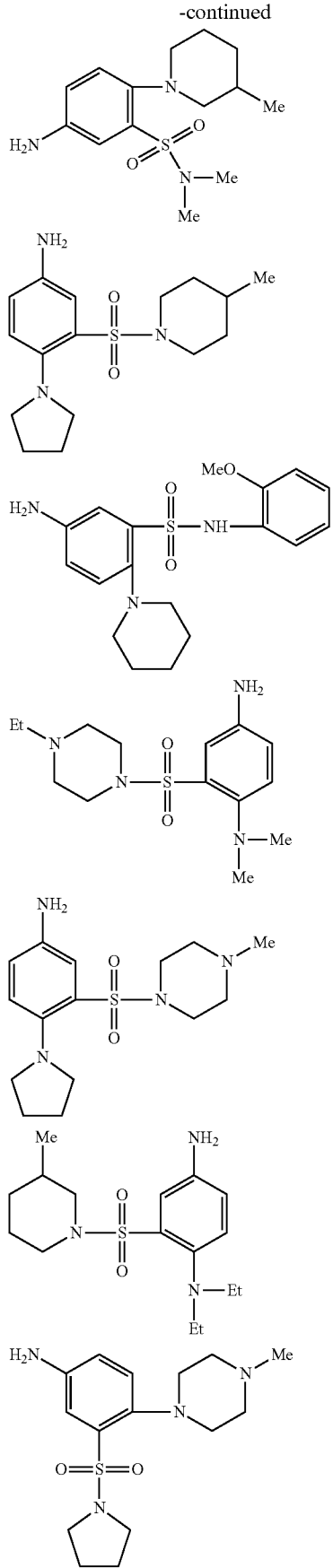
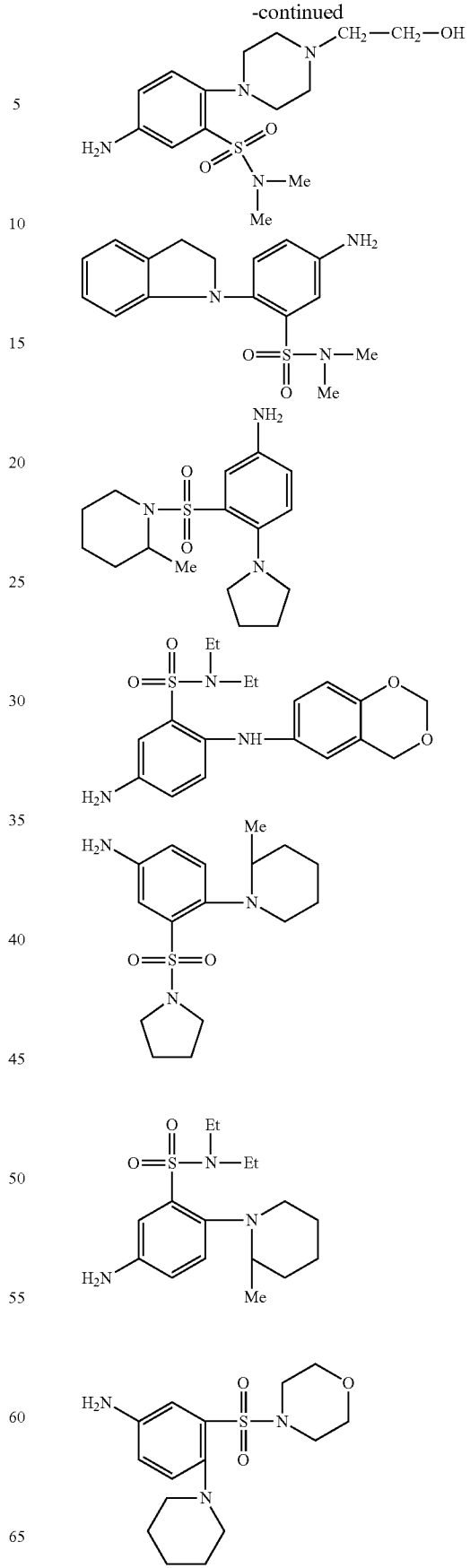

107
-continued
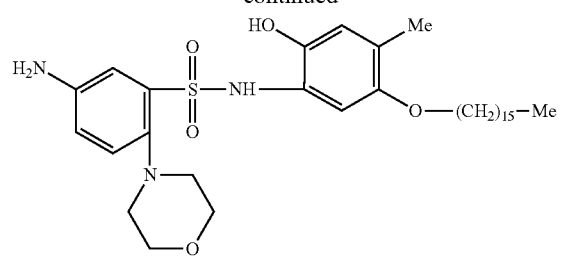
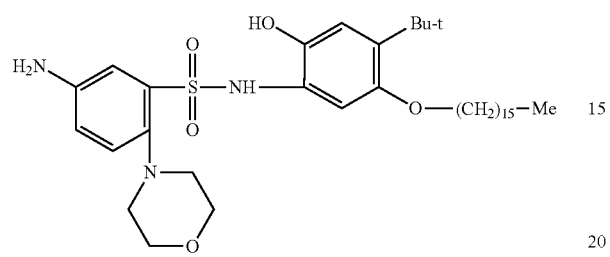
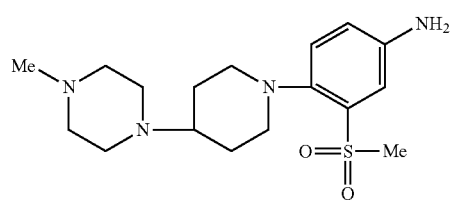
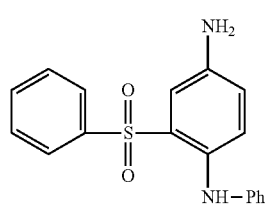
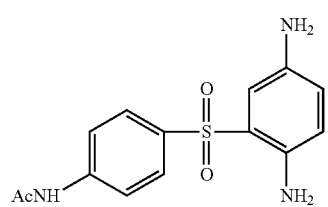
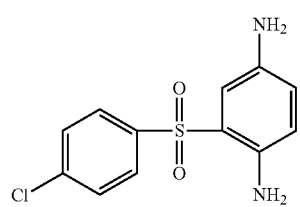
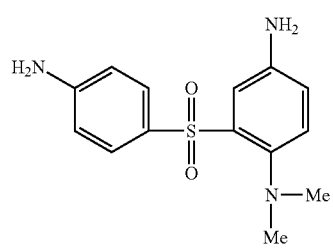
108
-continued
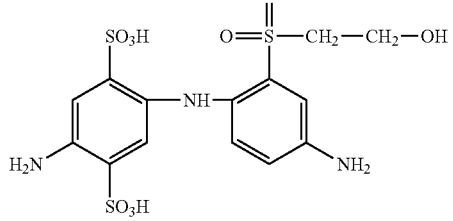
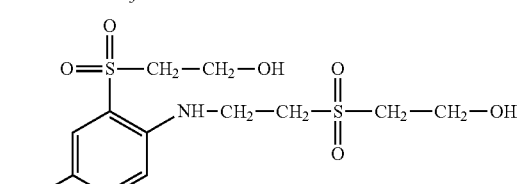
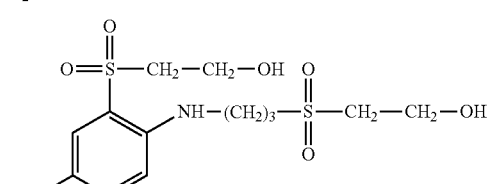
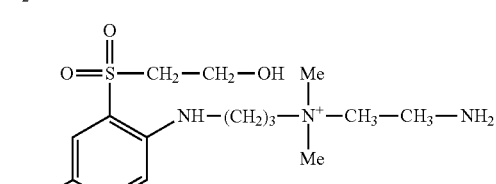
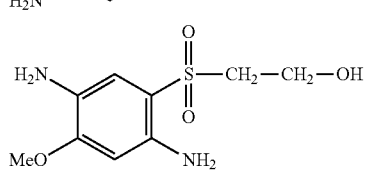
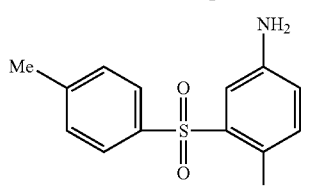
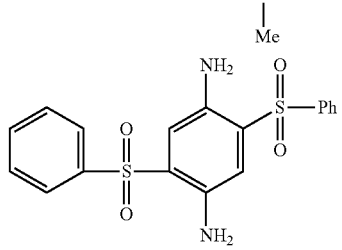
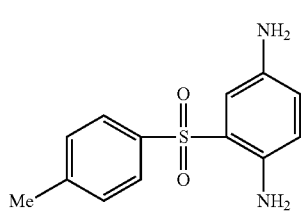

109
-continued
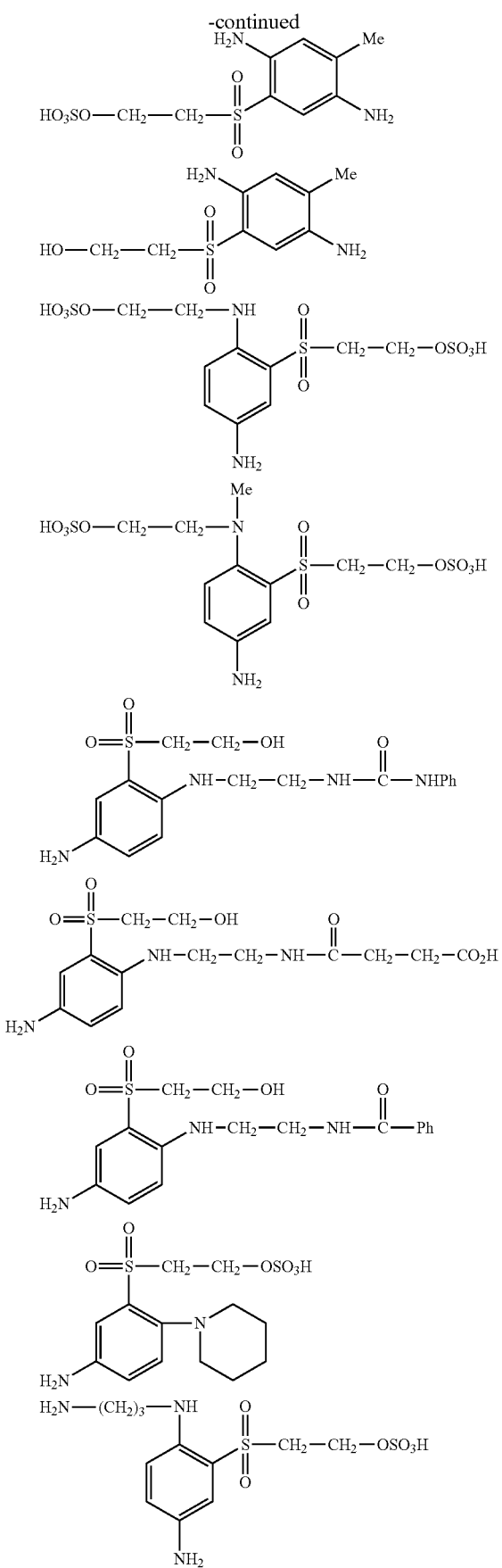
110
-continued
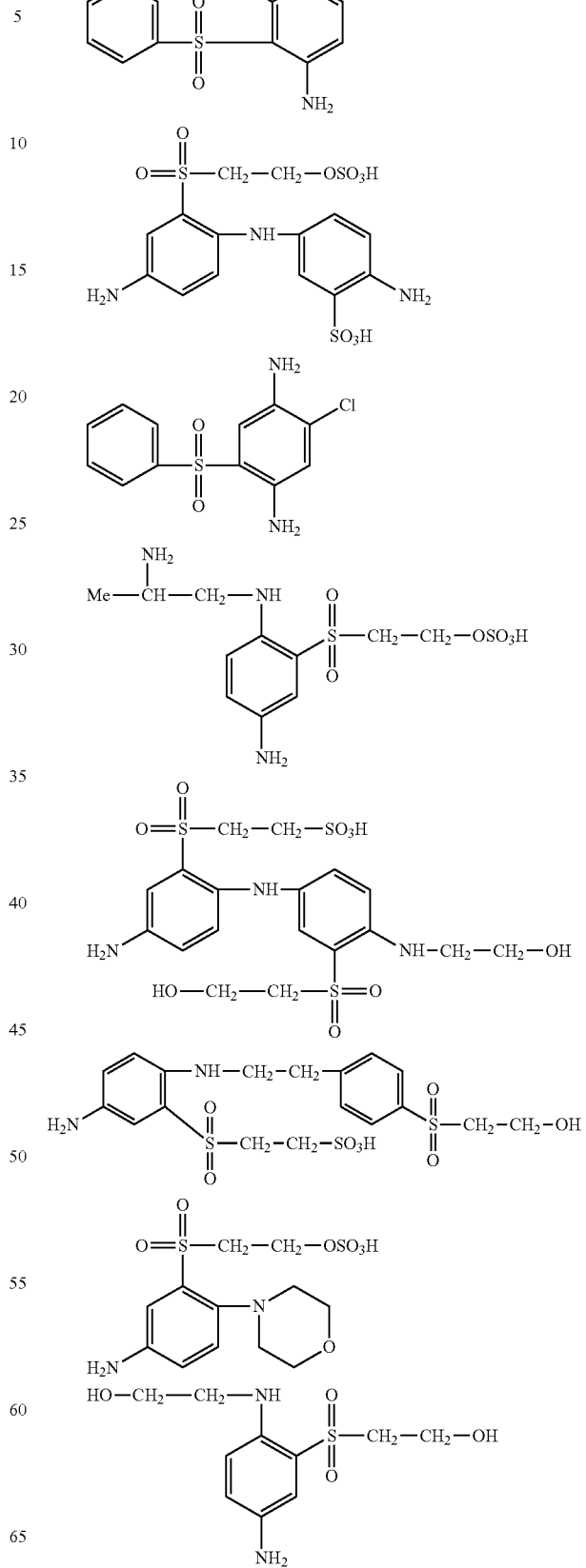

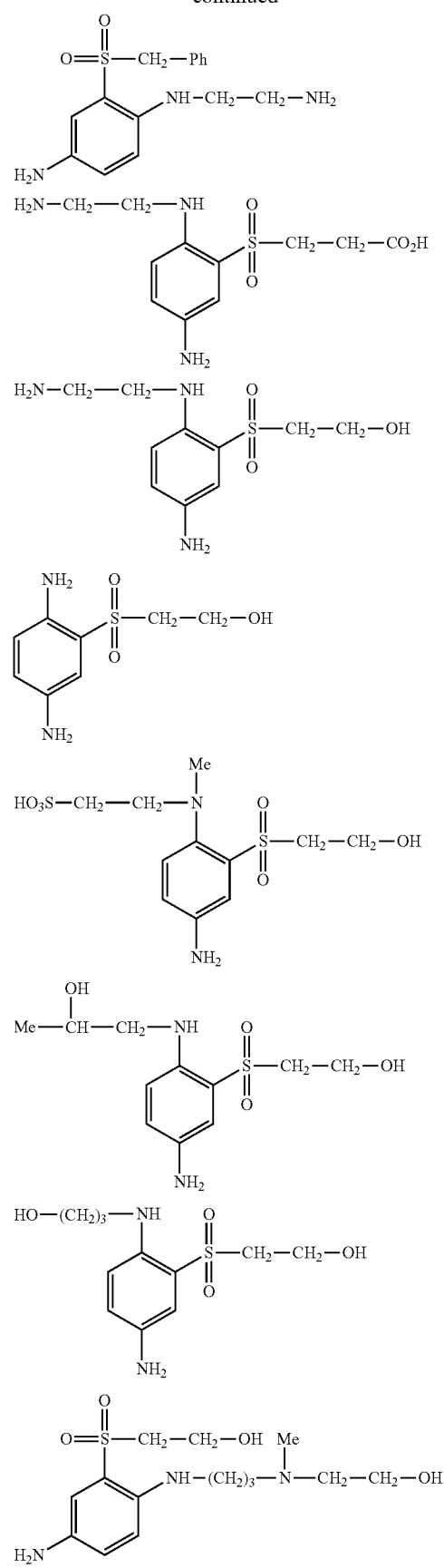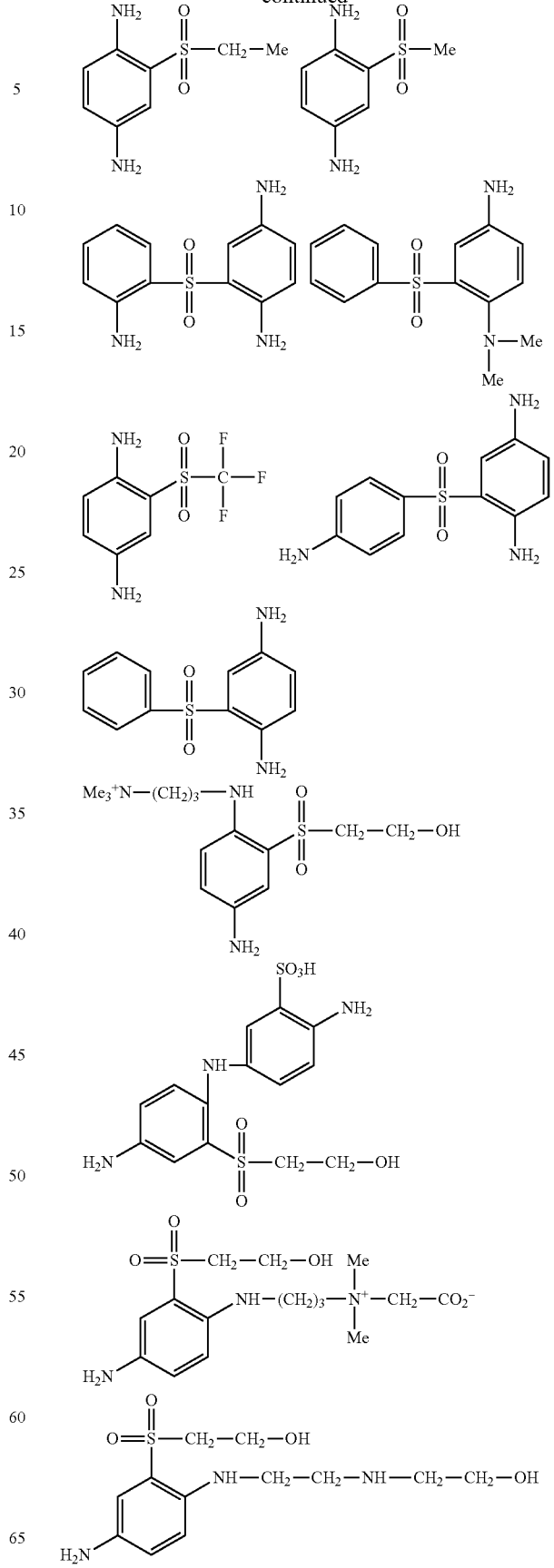

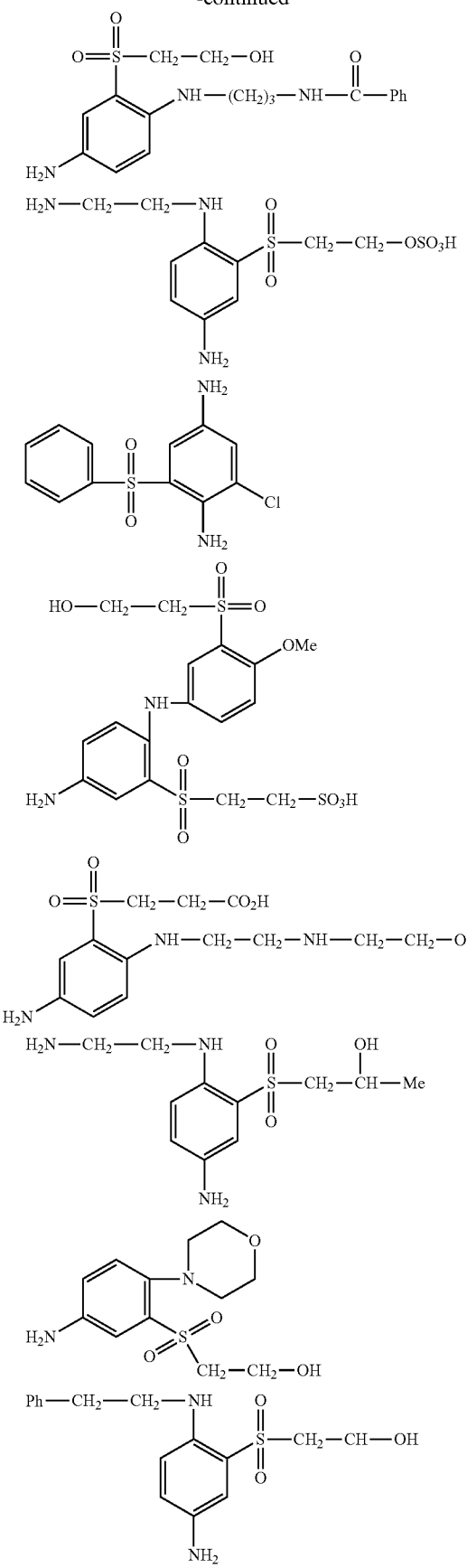

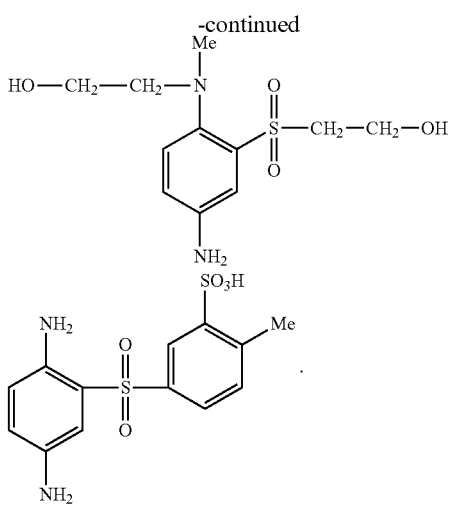

8. The method according to claim 2, wherein the at least one oxidation base is chosen from compounds of formula (II) wherein:

Z represents a hydroxyl group;

$R_1$ is chosen from:
- a hydroxyl radical,
- an amino radical —$NR_{11}R_{12}$, wherein $R_{11}$ and $R_{12}$, which may be identical or different, are chosen from:
  - a hydrogen atom;
  - a $C_1$-$C_{20}$ alkyl radical, optionally bearing at least one group chosen from:
    - a hydroxyl, $C_1$-$C_{15}$ alkoxy, or phenoxy group;
    - a —COOH group;
    - a —$SO_3H$ group;
    - a ($C_1$-$C_2$)alkylcarbonyl amino (or ($C_2$-$C_3$)acylamino) group;
    - an amino, optionally substituted with one or two $C_1$-$C_4$ alkyl radicals, which may be identical or different;
    - an aromatic or non-aromatic heterocycle having 5 to 6 ring members, the heterocycle optionally containing 1 or 2 endocyclic additional heteroatoms chosen from nitrogen; the nitrogen optionally bearing a hydrogen or a $C_1$-$C_4$ alkyl; or
    - a $C_6$-$C_{10}$ aryl radical comprising an aromatic nucleus, or two fused aromatic nuclei, the aryl radical being optionally substituted with at least one hydroxyl or $C_1$-$C_4$ alkoxy;
- a $C_6$-$C_{10}$ aryl radical comprising an aromatic nucleus optionally fused to another aromatic or heteroaromatic nucleus, wherein the heteroatom is nitrogen, the aryl radical being optionally substituted with at least one group chosen from $C_1$-$C_4$ alkyl, hydroxyl, $C_1$-$C_4$ alkoxy, trifluoromethyl, halogen, chlorine, ($C_1$-$C_2$)alkylcarbonylamino (($C_2$-$C_3$) acylamino), aminosulfonyl optionally substituted with one or two $C_1$-$C_4$ alkyl groups, acetylenyl, or $NH_2$—C(=$NH_2$)—;
- a saturated or unsaturated, aromatic or non-aromatic heterocycle having 5 ring members, comprising from one to four heteroatoms or nitrogen, with the proviso that the $R_{11}$ and $R_{12}$ radicals optionally form, together with the nitrogen atom to which they are attached, a cationic or non-cationic saturated heterocycle having 5 to 6 ring members, the heterocycle optionally containing one endocyclic additional heteroatom chosen from nitrogen or oxygen; the nitrogen optionally bearing one or two $C_1$-$C_4$ alkyls, which may be identical or different, the alkyl group optionally bearing an —$SO_3H$ group; the heterocycle optionally substituted, on at least one of its carbon atoms with a $C_1$-$C_4$ alkyl group optionally bearing a hydroxyl radical; a hydroxyl radical; the heterocycle being optionally fused to a $C_6$ aromatic nucleus; an aminocarbonyl radical; or a mono- or di-($C_1$-$C_2$) alkylaminocarbonyl radical;

$R_2$ and $R_3$, which may be identical or different, are chosen from:
  a hydrogen atom,
  a linear $C_1$-$C_{10}$ or branched $C_3$-$C_{10}$ alkyl radical, the alkyl radical being optionally substituted with at least one group chosen from hydroxyl, $C_1$-$C_4$ alkoxy, amino optionally substituted with one or two $C_1$-$C_4$ alkyl radicals which may be identical or different, or mono- or di- ($C_1$-$C_2$)alkylaminocarbonyl;
  with the proviso that the radicals $R_2$ and $R_3$ optionally form, together with the nitrogen atom to which they are connected, a saturated or unsaturated, aromatic or non-aromatic heterocycle having from 5 to 7 ring members, the heterocycle optionally containing one endocyclic additional heteroatom chosen from nitrogen or oxygen, the nitrogen optionally bearing one or two $C_1$-$C_4$ alkyl(s), which may be identical or different;

$R_4$, which may be identical or different, is chosen from:
  a hydrogen atom,
  a $C_1$-$C_{20}$ alkyl or $C_2$-$C_6$ alkenyl; the alkyl or alkenyl being optionally substituted with at least one amino group which is unsubstituted or substituted with one or two $C_1$-$C_4$ alkyl groups which may be identical or different, trifluoromethyl, a saturated or unsaturated (hetero)cycle having 5 or 6 ring members, optionally comprising one or two heteroatoms or nitrogen; wherein the nitrogen optionally bears a $C_1$-$C_4$ alkyl group;
  a saturated or unsaturated (hetero)cycle having 5 or 6 ring members, optionally comprising one or two heteroatoms, nitrogen or oxygen; wherein the nitrogen optionally bears a hydrogen atom or a $C_1$-$C_4$ alkyl group; or an endocyclic carbonyl group, wherein the (hetero)cycle is optionally substituted with a hydroxyl group,
  a —COOH group,
  a —$SO_3H$ group,
  halogens, chlorine, fluorine, or bromine,
  hydroxyl, $C_1$-$C_4$ alkoxy optionally bearing a carboxylic group, or ($C_1$-$C_4$)alkylthio;
  ($C_1$-$C_4$)alkylcarbonyl, $C_2$-$C_4$ acyl, ($C_1$-$C_2$)alkylcarbonyl amino, ($C_2$-$C_3$)acylamino, ($C_1$-$C_2$)alkylaminocarbonyl, or aminocarbonyl,
  trifluoromethyl, or
  aryl($C_1$-$C_4$)alkyl,
  with the proviso that two $R_4$ radicals borne by adjacent carbon atoms may optionally form an aromatic or non-aromatic, fused cycle or heterocycle having from 5 to 6 ring members; the heterocycle optionally comprising at least one heteroatom chosen from nitrogen or oxygen, wherein the nitrogen atom may optionally bear a hydrogen atom or a $C_1$-$C_4$ alkyl radical; and the ring or heterocycle may optionally be substituted, on at least one of the carbon atoms, with a $C_1$-$C_4$ alkyl radical;

wherein, if $R_1$ represents a hydroxyl group, then at most two $R_4$ groups represent hydrogen atoms.

9. The method according to claim 2, wherein the at least one oxidation base is chosen from compounds of formula (II) wherein:
  Z represents an amino group optionally substituted with one or two $C_1$-$C_4$ alkyl radicals, which may be identical or different;
  $R_1$ is an amino radical —$NR_{11}R_{12}$, wherein $R_{11}$ and $R_{12}$, which may be identical or different, are chosen from:
    a hydrogen atom;
    a $C_1$-$C_{20}$ alkyl radical, optionally bearing at least one group chosen from:
      a hydroxyl or $C_1$-$C_{15}$ alkoxy;
      a cyano group;
      a mono- or di-($C_1$-$C_2$)alkylaminocarbonyl;
      an amino, optionally substituted with one or two $C_1$-$C_4$ alkyl radicals, which may be identical or different;
      an aromatic or non-aromatic heterocycle having 5 to 6 ring members, optionally containing 1 or 2 endocyclic heteroatoms chosen from nitrogen; the nitrogen optionally bearing a hydrogen atom or a $C_1$-$C_4$ alkyl; or
      a $C_6$-$C_{10}$ aryl radical comprising an aromatic nucleus, or two fused aromatic nuclei, the aryl radical being optionally substituted with at least one $C_1$-$C_4$ alkyl radical, hydroxyl, $C_1$-$C_4$ alkoxy, or trifluoromethyl; or
    a $C_6$-$C_{10}$ aryl radical comprising an aromatic nucleus optionally fused to another aromatic or heteroaromatic nucleus, wherein the heteroatom is nitrogen, the aryl radical being optionally substituted with at least one group chosen from $C_1$-$C_4$ alkyl, hydroxyl or $C_1$-$C_4$ alkoxy;
    with the proviso that the $R_{11}$ and $R_{12}$ radicals may optionally form, together with the nitrogen atom to which they are attached, a saturated or unsaturated heterocycle having 5 or 6 ring members, the heterocycle optionally containing one endocyclic additional heteroatom which may be identical or different, chosen from nitrogen or oxygen; the nitrogen optionally bearing one or two $C_1$-$C_4$ alkyls, which may be identical or different; the alkyl group optionally bearing an —$SO_3H$ group; the heterocycle being optionally substituted, on at least one of its carbon atoms, with one or two $C_1$-$C_4$ alkyl groups, which may be identical or different; the alkyl group optionally bearing a hydroxyl radical, an aminocarbonyl radical; or a mono- or di-($C_1$-$C_2$)alkylaminocarbonyl radical;
  $R_2$ and $R_3$, which may be identical or different, are chosen from:
    a hydrogen atom,
    a linear $C_1$-$C_{10}$, branched $C_3$-$C_{10}$, or cyclic $C_5$-$C_{10}$ alkyl radical; the alkyl radical being optionally substituted with at least one group chosen from ($C_1$-$C_4$) alkylthio (RS-), cyano, hydroxyl, $C_1$-$C_4$ alkoxy, amino optionally substituted with one or two $C_1$-$C_4$ alkyl radicals which may be identical or different, mono- or di-($C_1$-$C_2$)alkylaminocarbonyl; a saturated, unsaturated or aromatic heterocycle having from 5 to 7 ring members comprising 1 or 2 endocyclic heteroatoms chosen from nitrogen, oxygen or sulfur, a saturated or unsaturated $C_5$-$C_{10}$ heterocyclic radical comprising at least one heteroatom or nitrogen, the nitrogen atom optionally bearing a hydrogen atom or a $C_1$-$C_4$ alkyl radical, a $C_6$-$C_{10}$ aryl or heteroaryl radical optionally comprising at least one endocyclic heteroatom; the radical optionally substituted with one or two $C_1$-$C_4$ alkyl radicals, one or two $C_1$-$C_4$ alkoxy groups, or one or two amino groups optionally substituted with one or two $C_1$-$C_4$ alkyl groups, which may be identical or different; with the proviso that two substituents borne by adjacent carbon atoms of the aryl or heteroaryl radical may form an aromatic or non-aromatic, fused ring or heterocycle comprising from 5 to 6 ring members, optionally comprising one or two endocyclic heteroatoms, oxygen, or nitrogen, with the proviso that the $R_2$ and $R_3$ may optionally form, together with the nitrogen atom to which they are connected, a saturated or unsaturated, aromatic or non-aromatic heterocycle having 5 or 6 ring members, optionally containing 1 or 2 endocyclic additional heteroatoms, which may be identical or different, chosen from nitrogen, oxygen or sulfur, or else containing a carbonyl group; the nitrogen optionally bearing one or two $C_1$-$C_4$ alkyl, which may be identical or different; the heterocycle optionally fused to an aromatic nucleus or a saturated $C_5$-$C_7$ ring, the heterocycle being optionally substituted on one of the carbon atoms, with one or two groups, which may be identical or different, chosen from $C_1$-$C_4$ alkyl optionally bearing a hydroxyl, $C_1$-$C_4$ alkoxy, hydroxyl, amino optionally substituted with one or two radicals which may be identical or different, aminocarbonyl, or mono- or di-($C_1$-$C_2$)alkylaminocarbonyl, and $R_4$, which may be identical or different, is chosen from:
a hydrogen atom,
a $C_1$-$C_{20}$ alkyl,
halogens, chlorine, fluorine, or bromine,
hydroxyl or $C_1$-$C_4$ alkoxy, or
mono- or di-($C_1$-$C_2$)alkylaminocarbonyl or aminocarbonyl.

10. The method according to claim 2, wherein the at least one oxidation base is chosen from the following compounds of formula (II), addition salts thereof, solvates thereof or mixtures thereof:

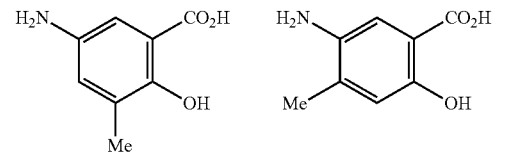

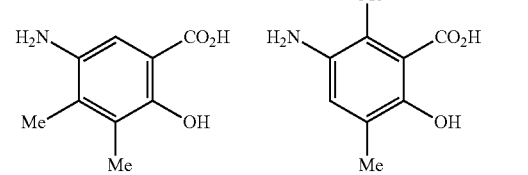

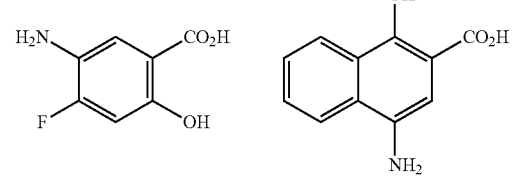

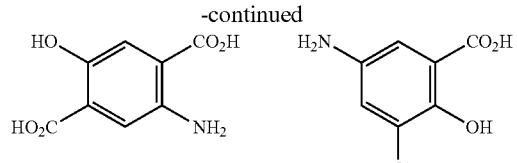

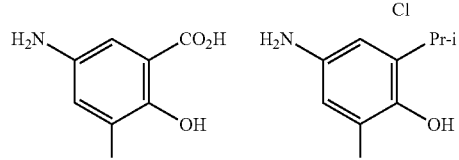

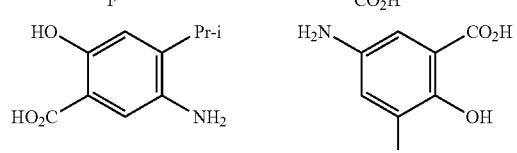

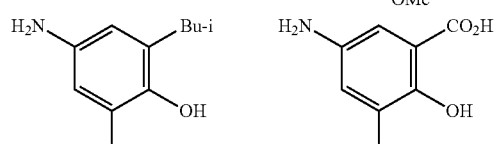

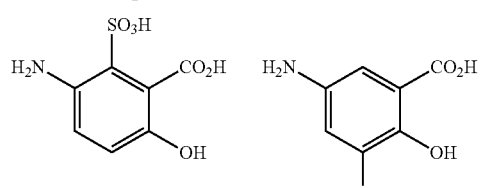

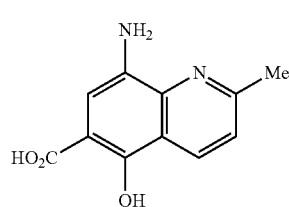

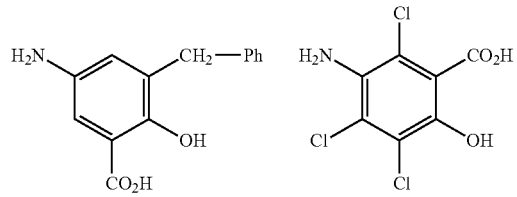

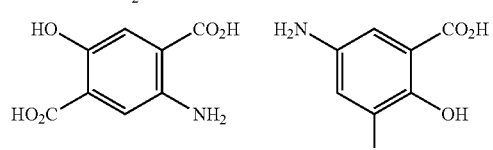

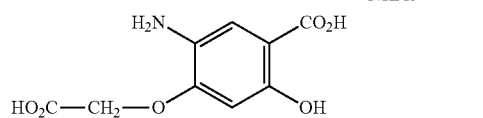

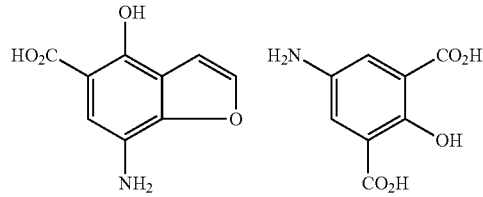

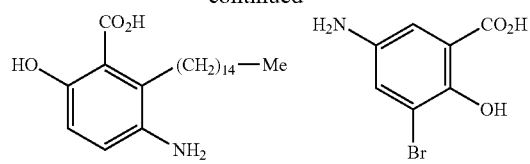
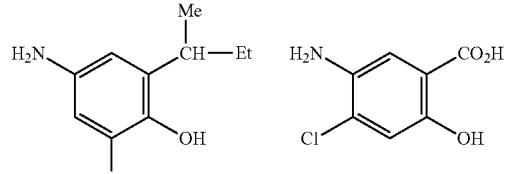
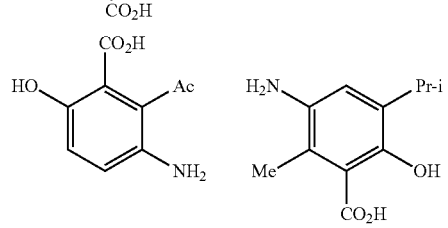
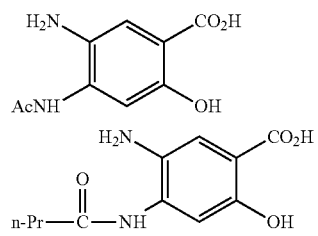
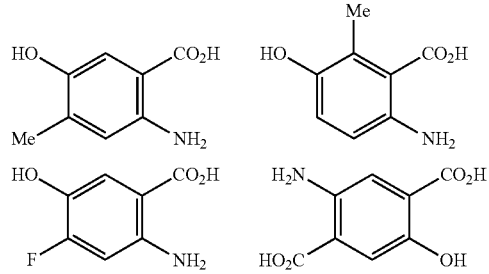
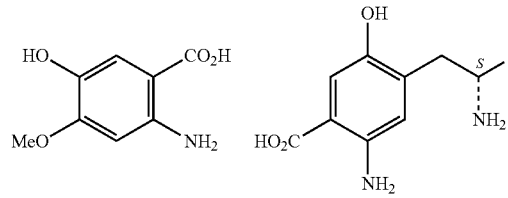
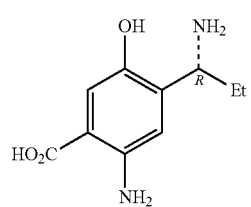
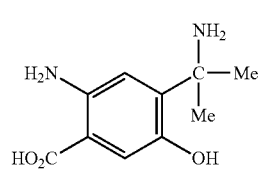
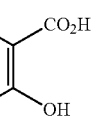
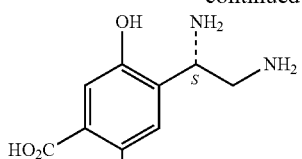
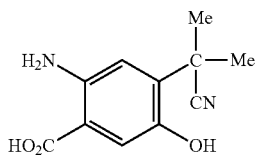
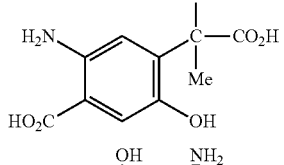
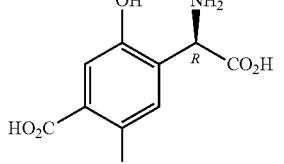
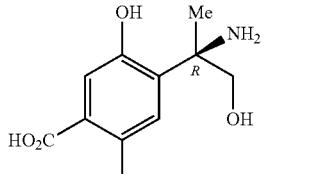
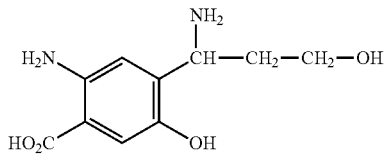
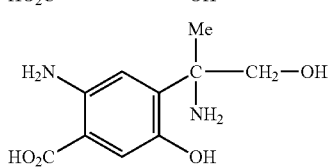

-continued
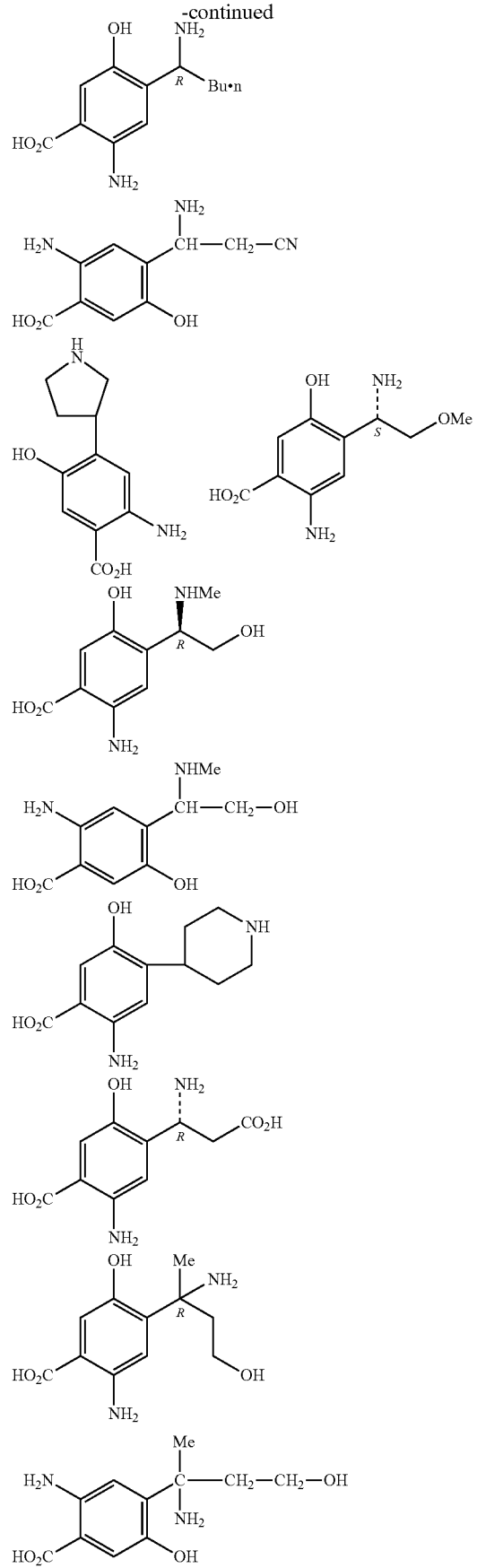
-continued
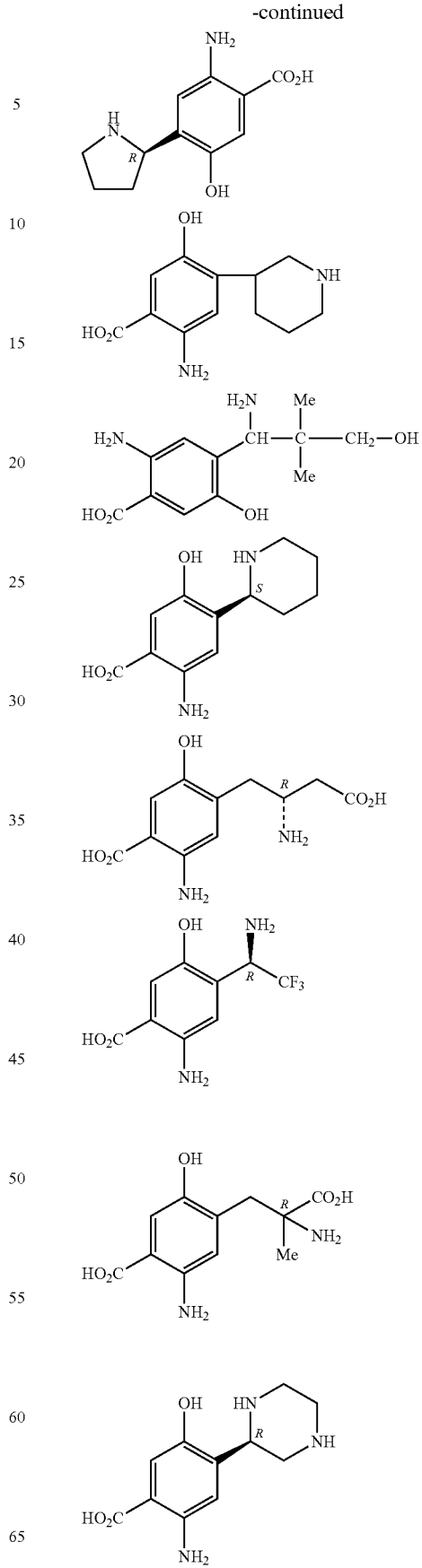

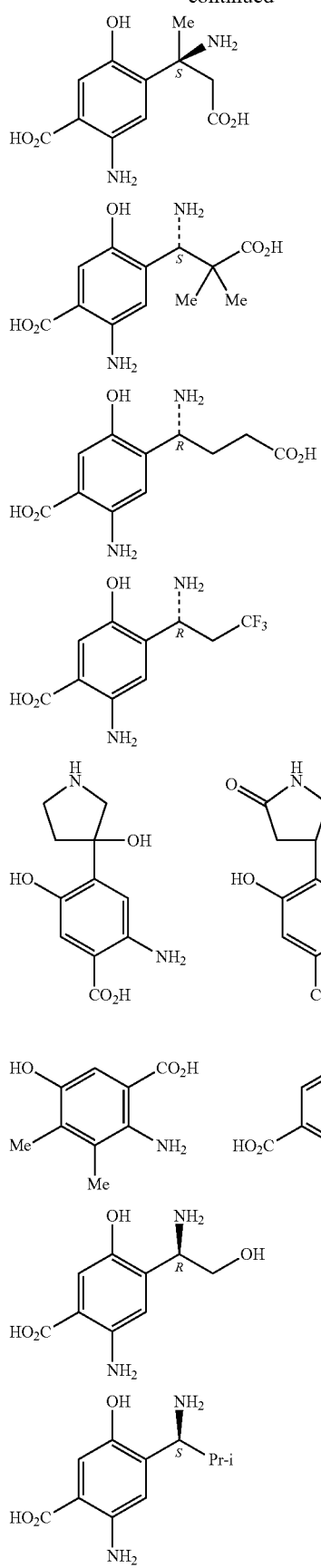
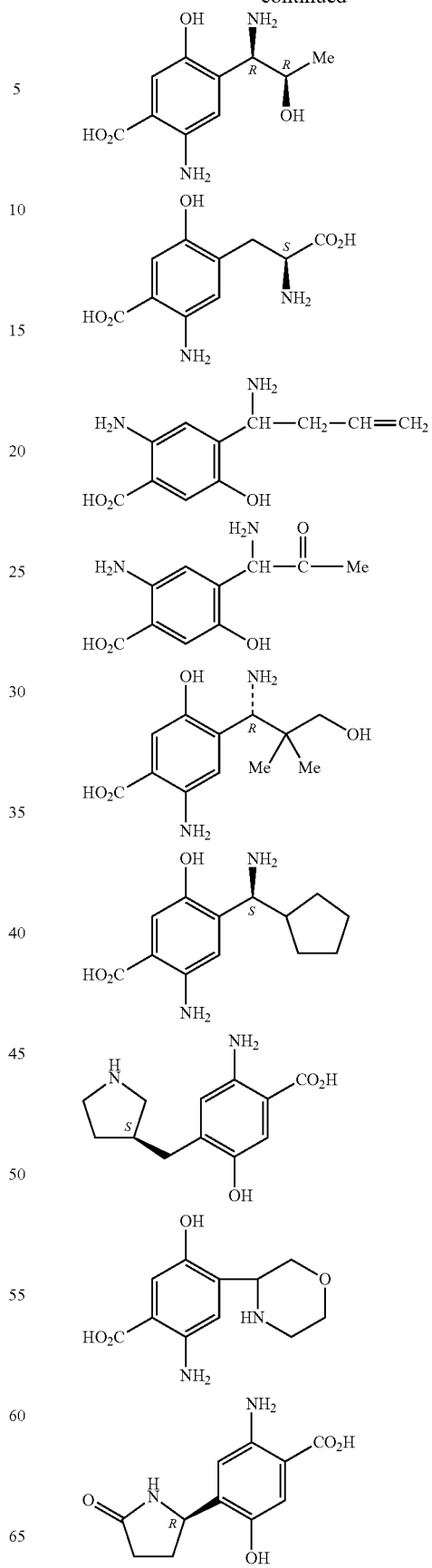

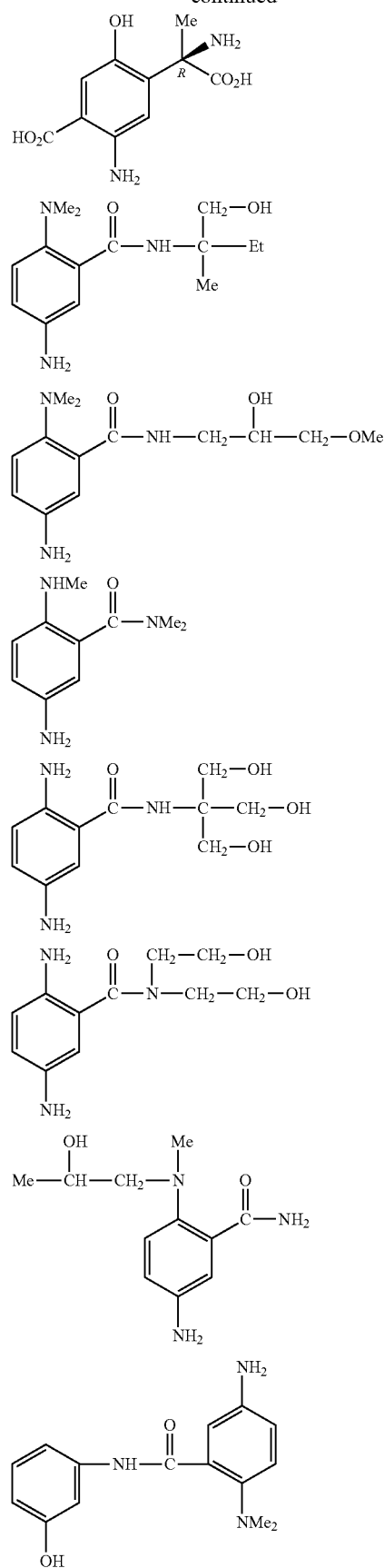
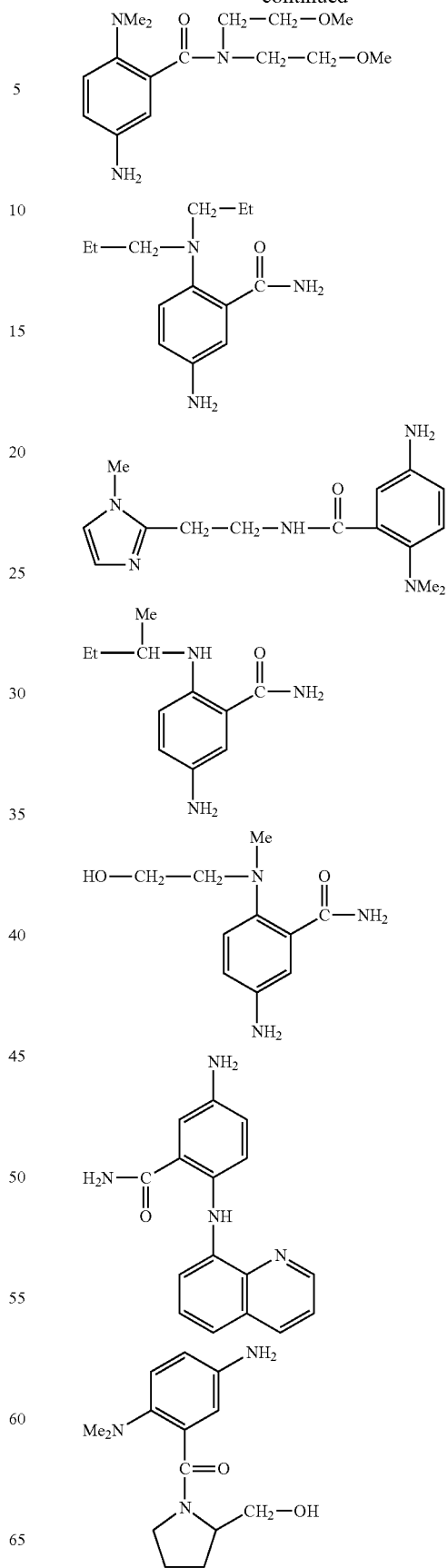

127
-continued
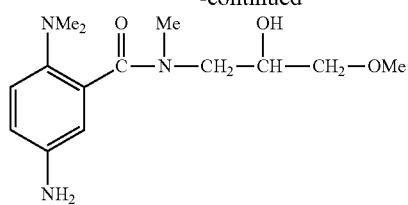
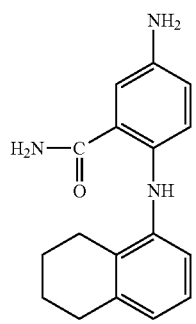
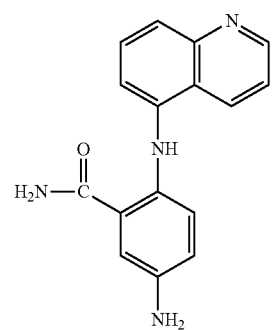
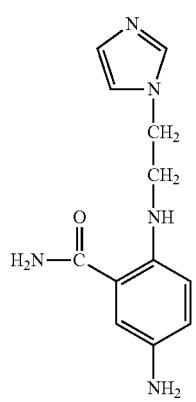
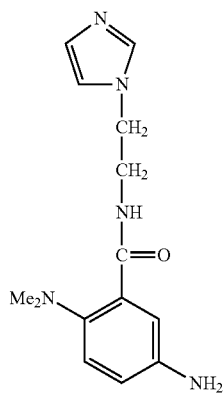
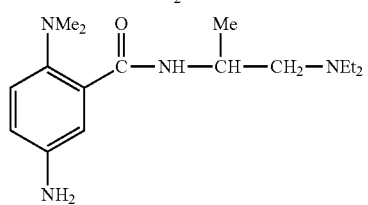
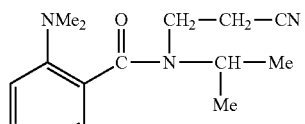
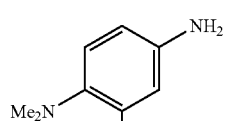
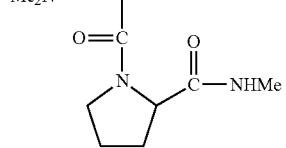
128
-continued
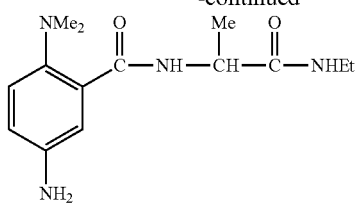
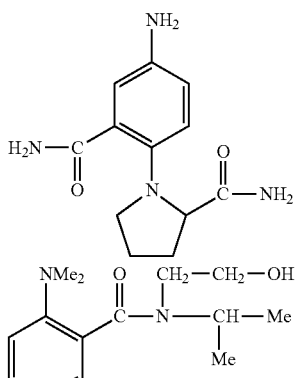
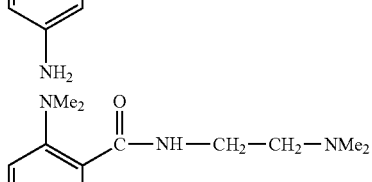
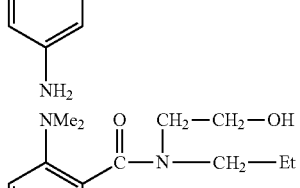
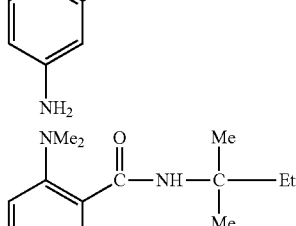
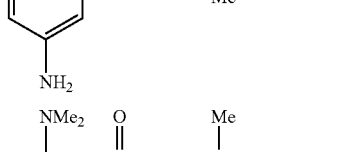
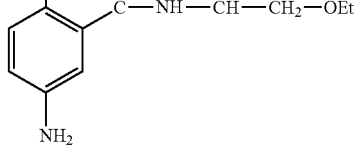
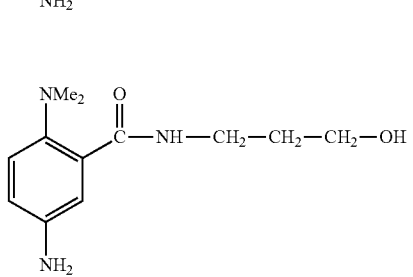

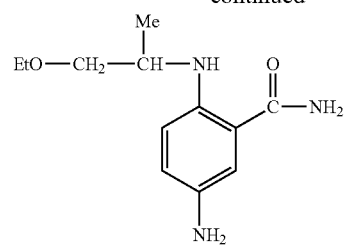
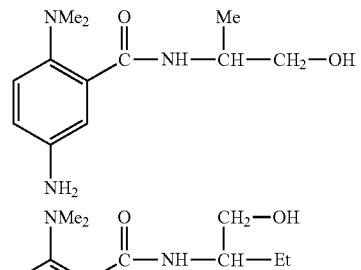
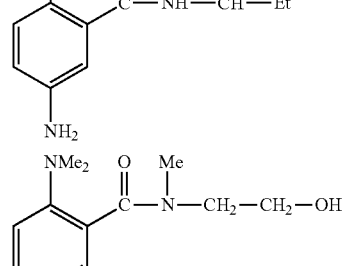
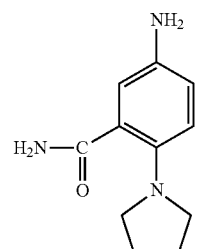
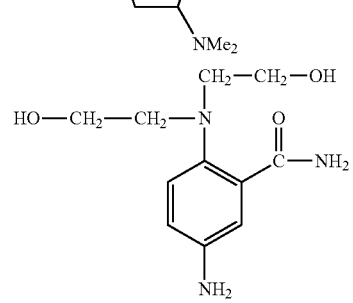
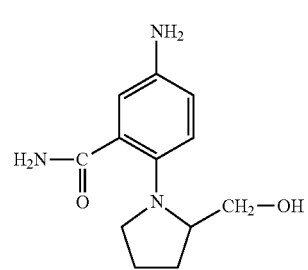
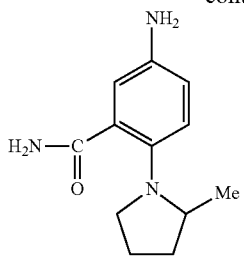
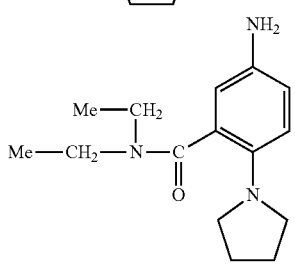
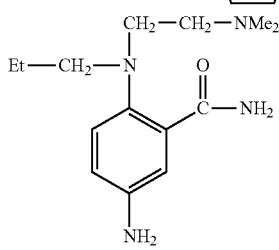
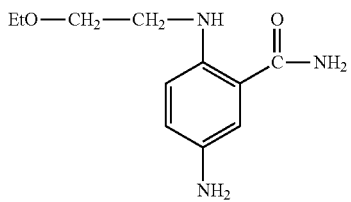
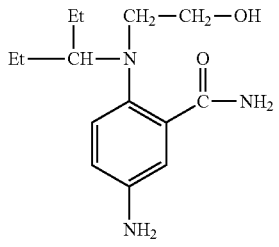
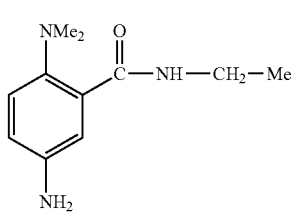
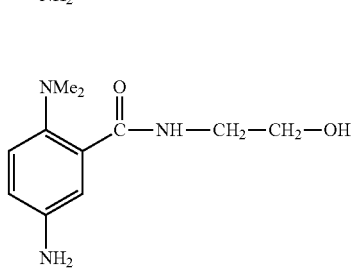

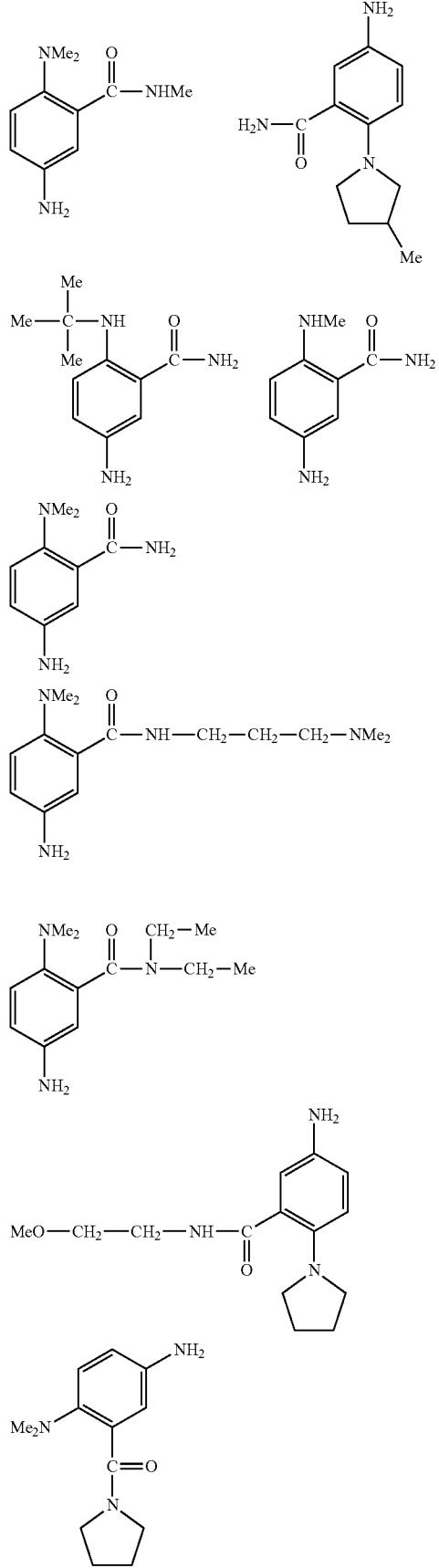
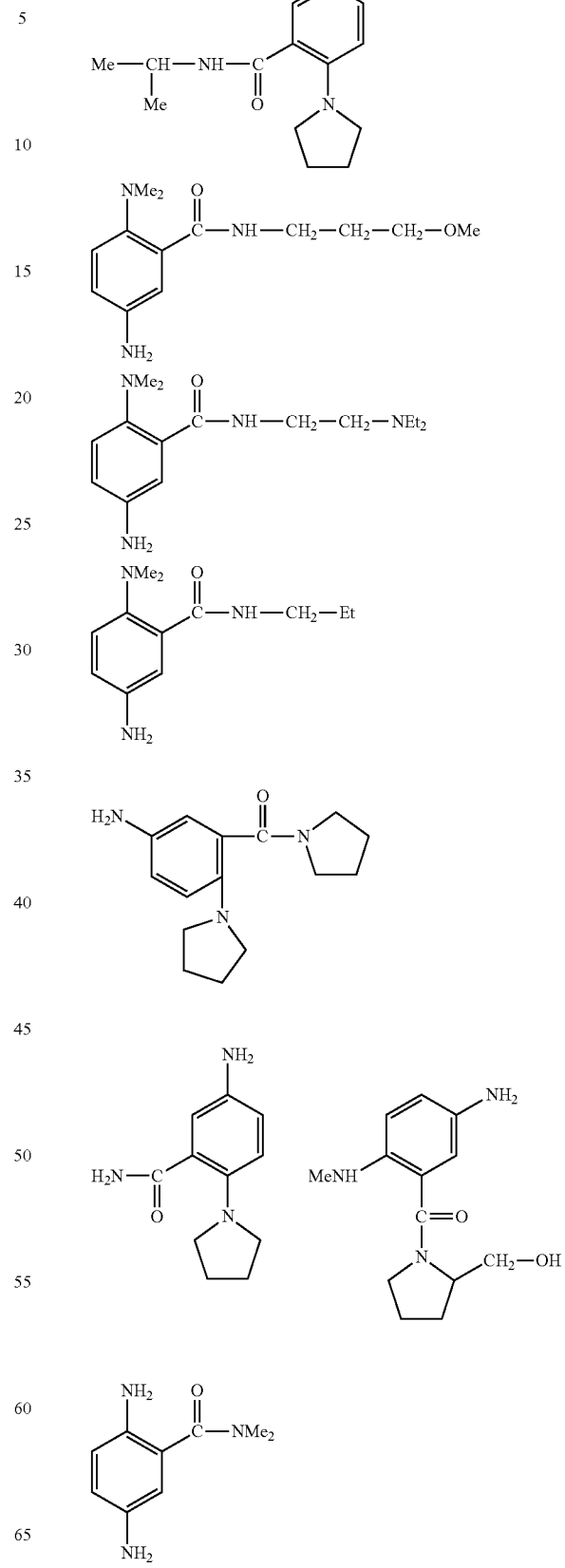

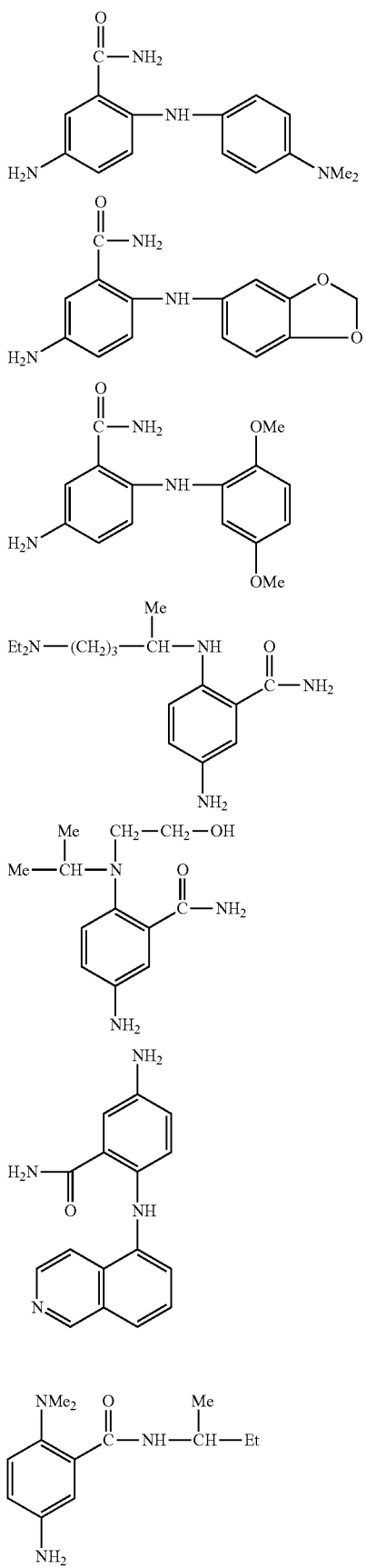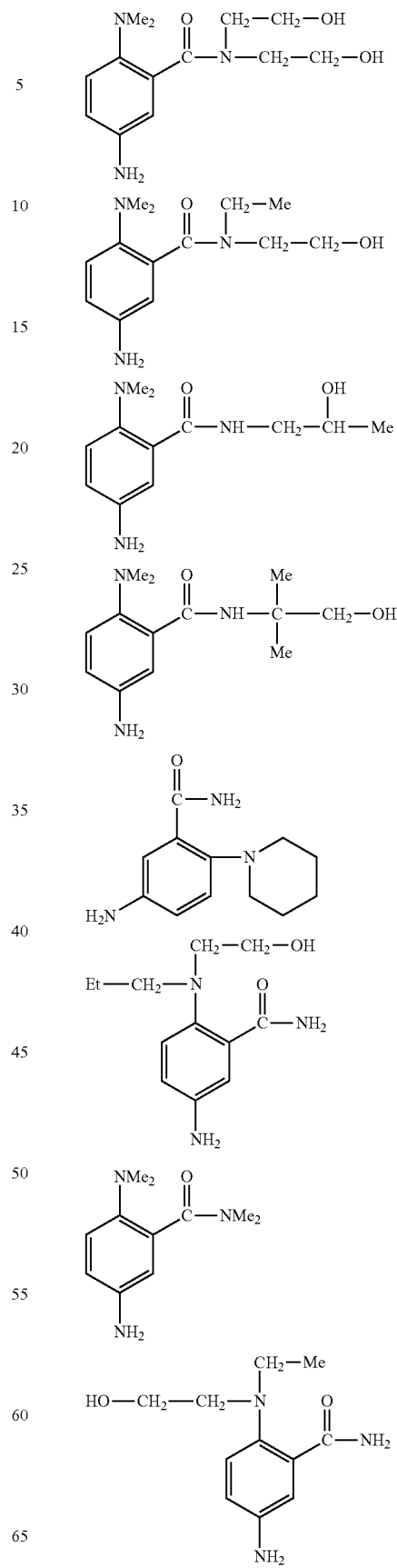

-continued
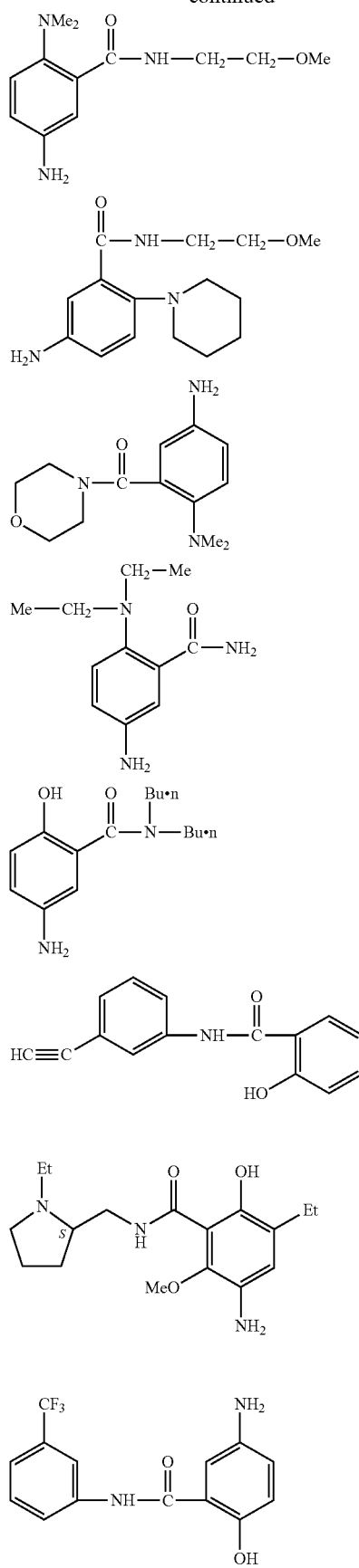
-continued
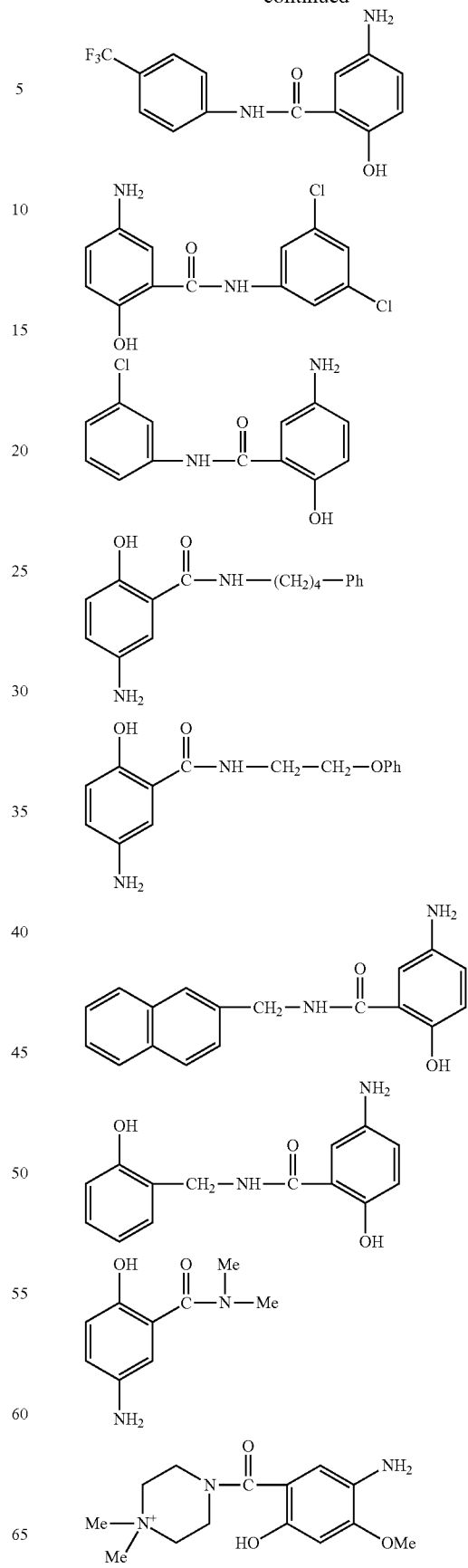

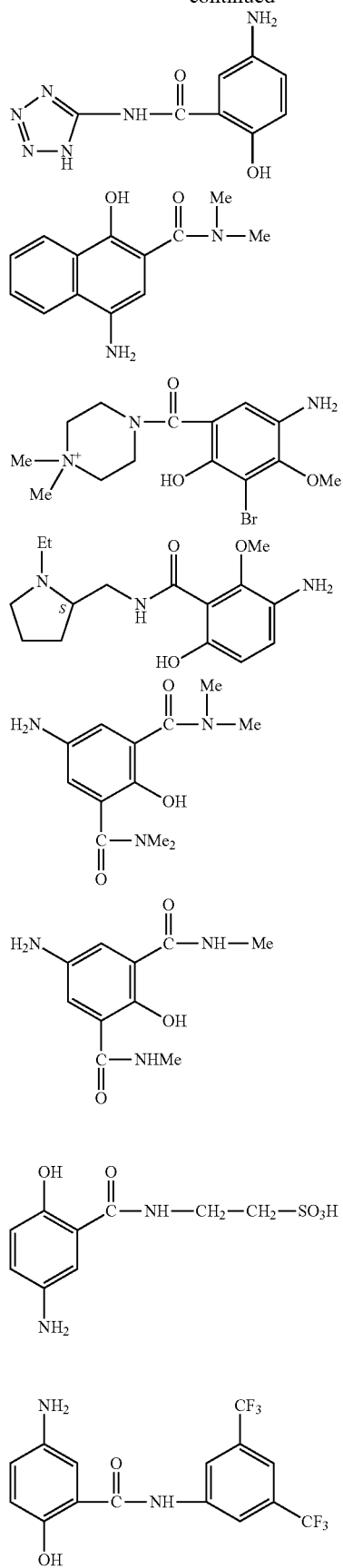
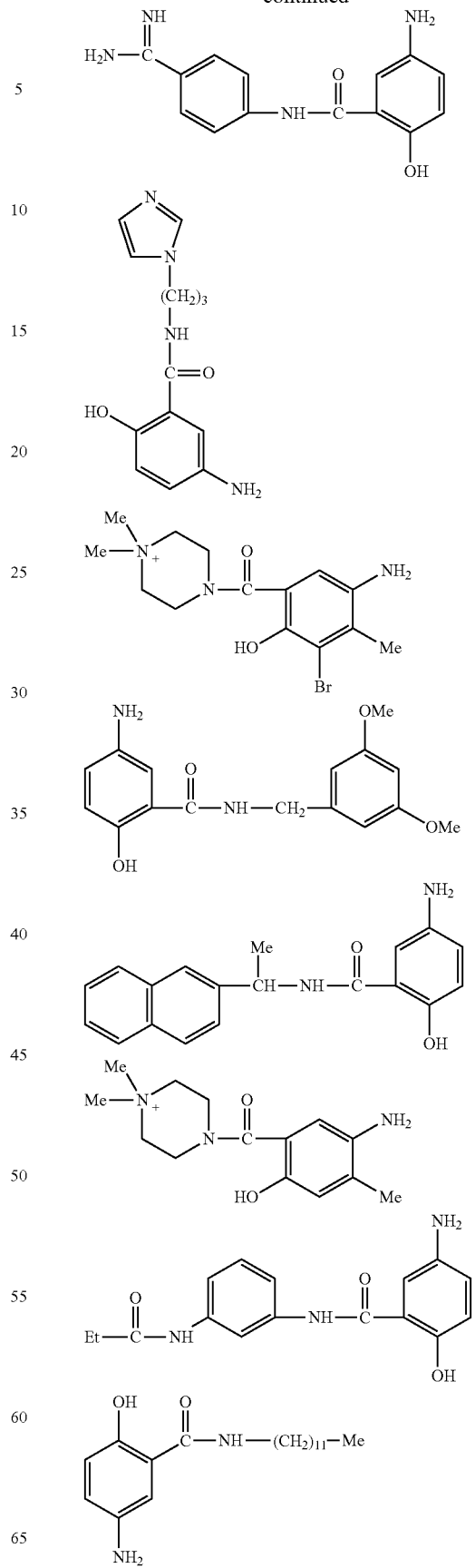

-continued
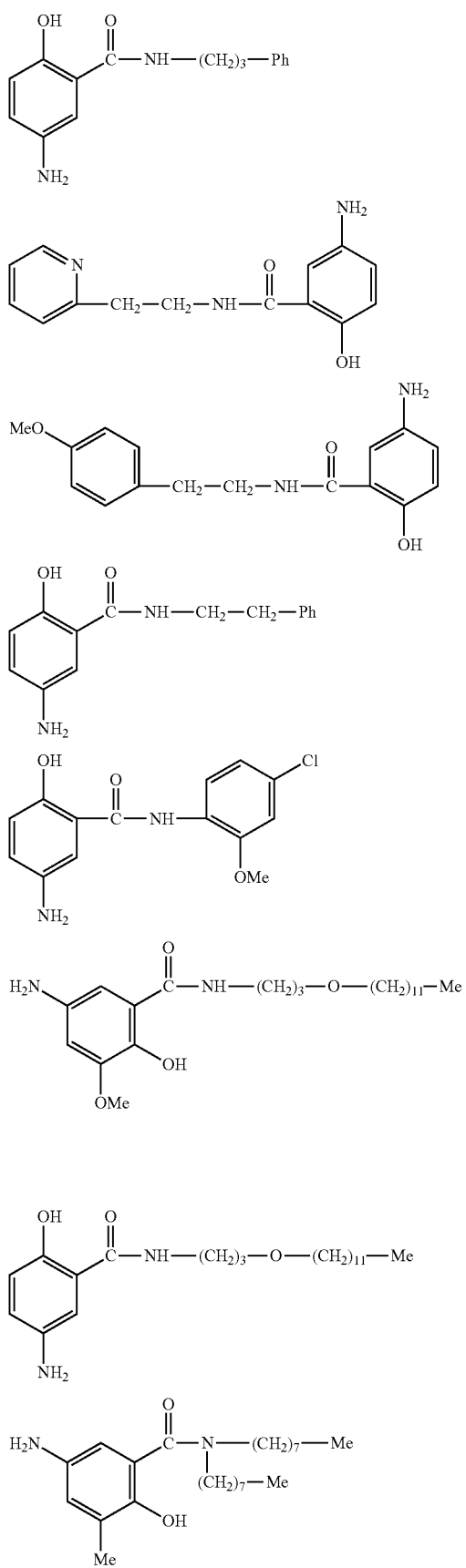
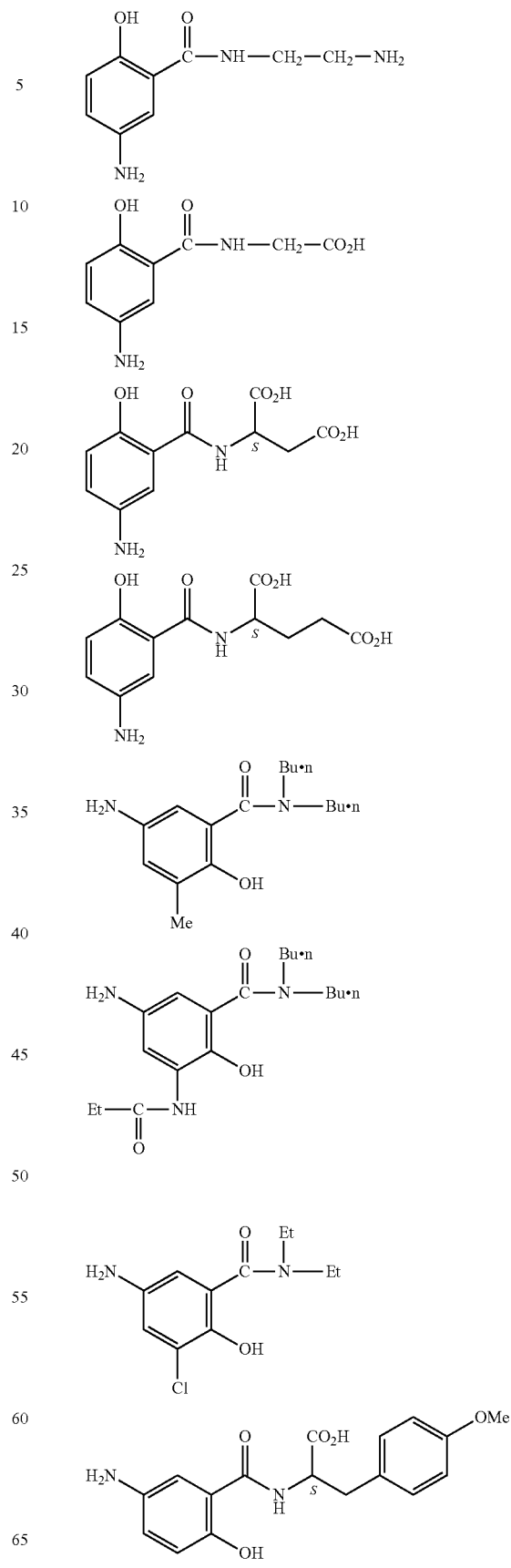

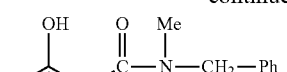
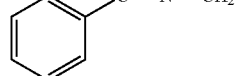
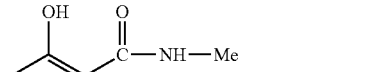
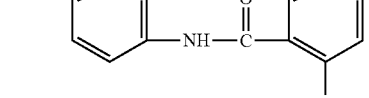
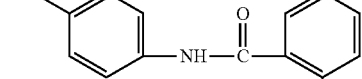
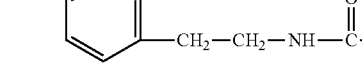
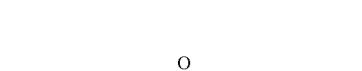
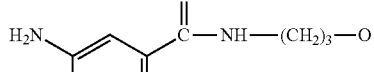
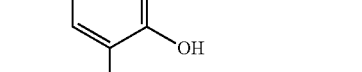

-continued
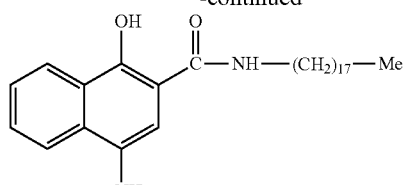
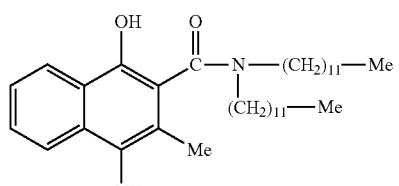
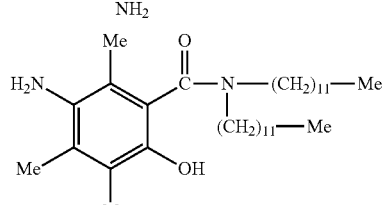
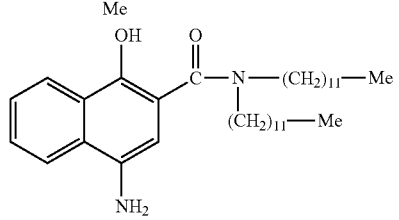
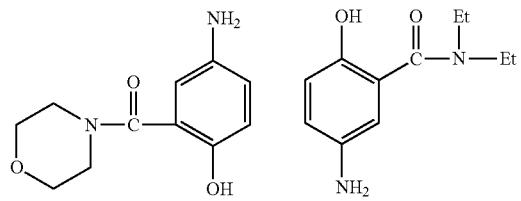
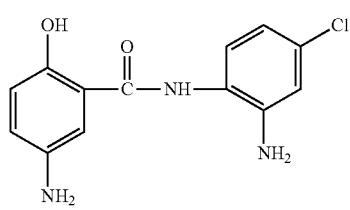
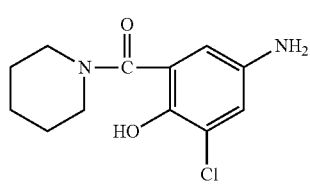
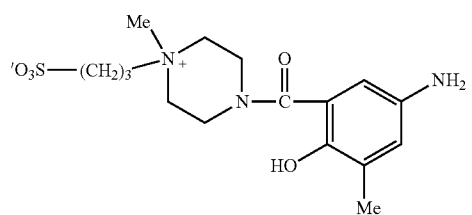
-continued
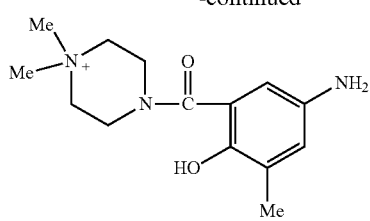
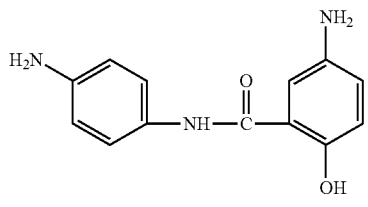
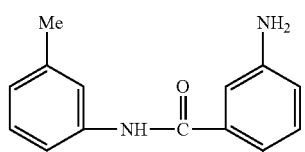
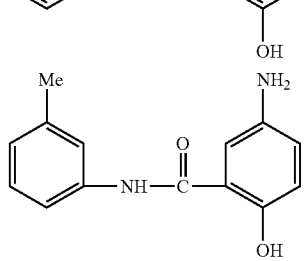
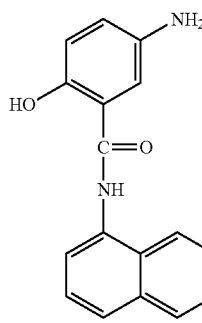
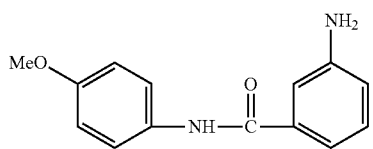
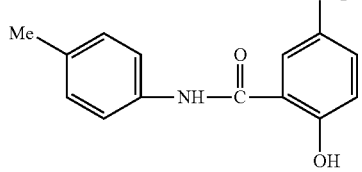
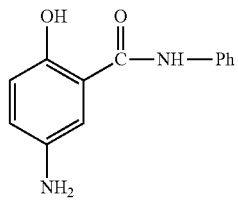

-continued
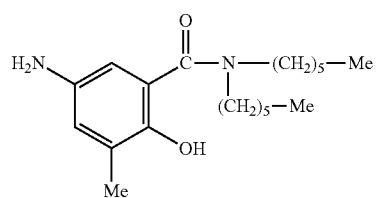
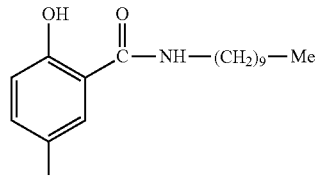
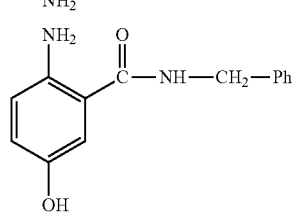
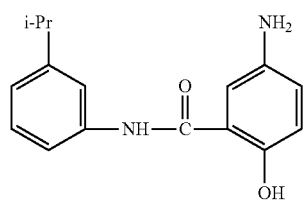
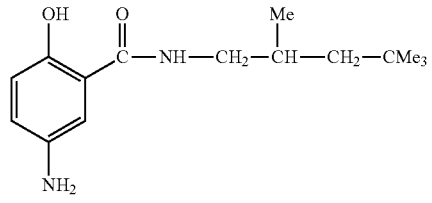
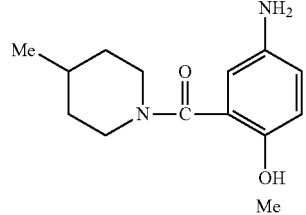
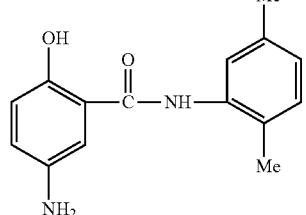
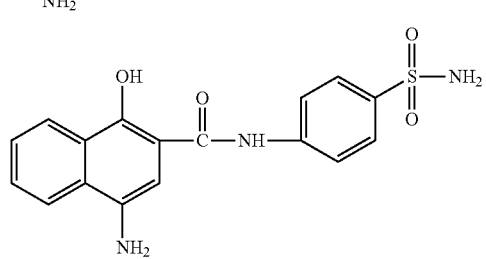
-continued
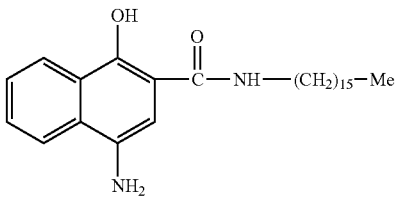
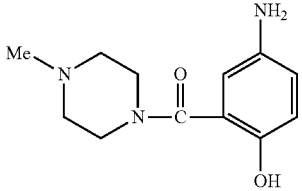
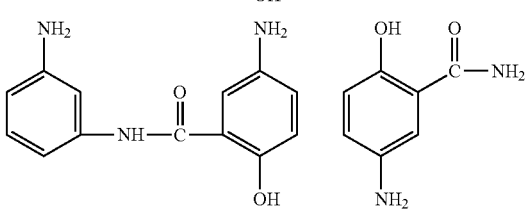
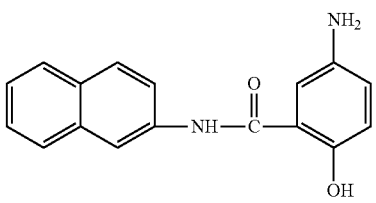
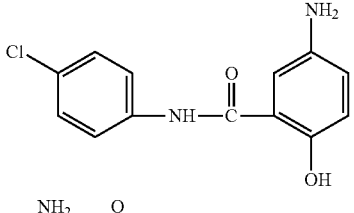
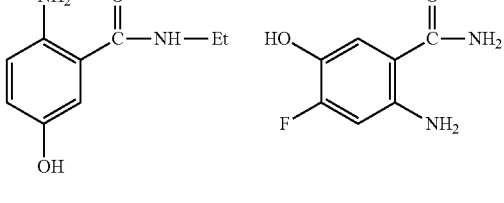
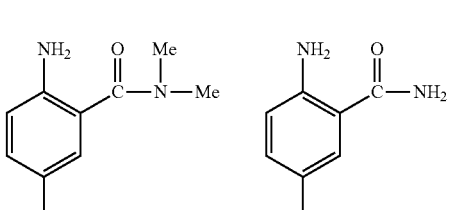
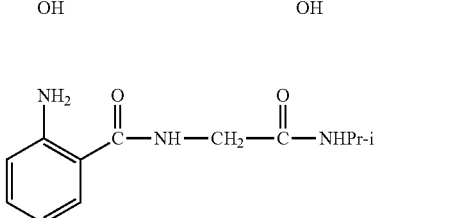

-continued
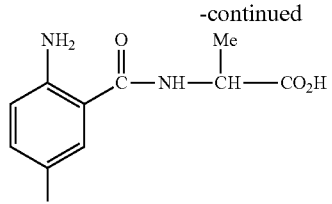
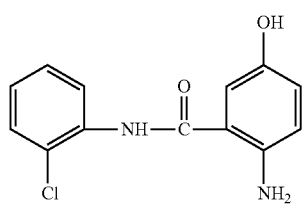
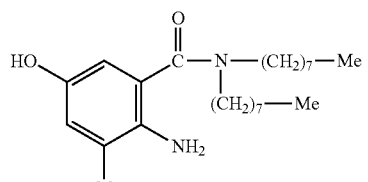
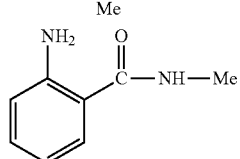
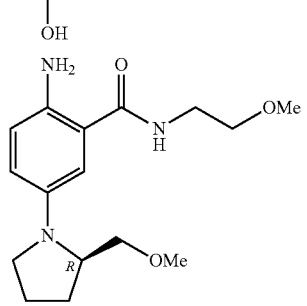
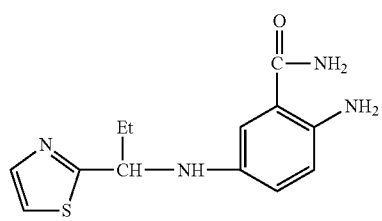
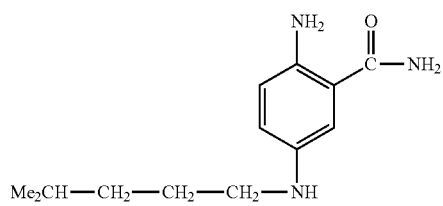
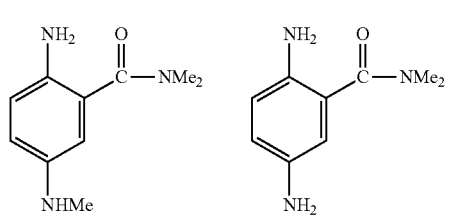
-continued
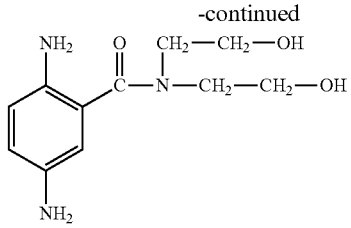
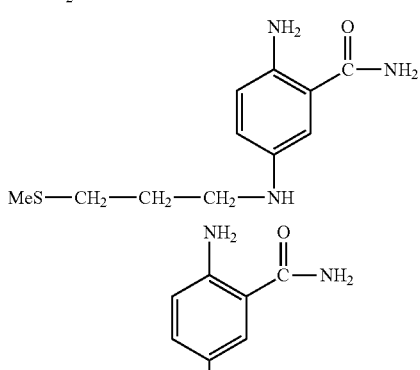
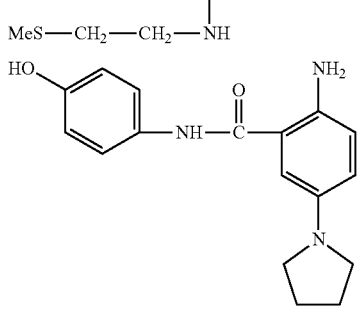
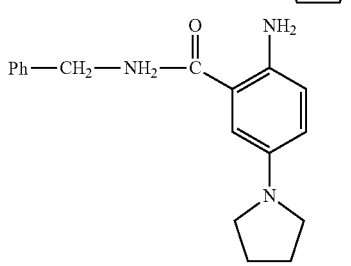
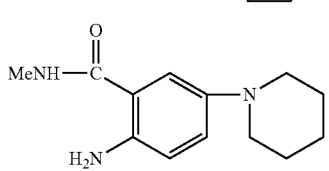
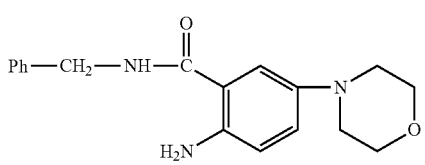
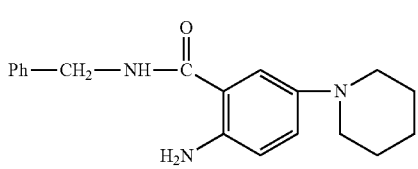

149
-continued
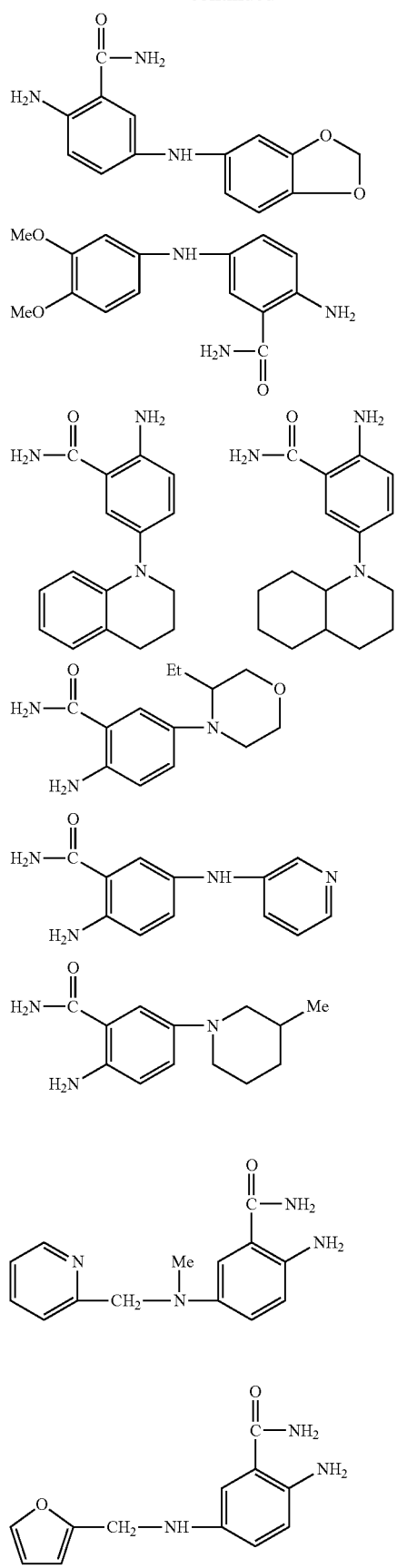
150
-continued
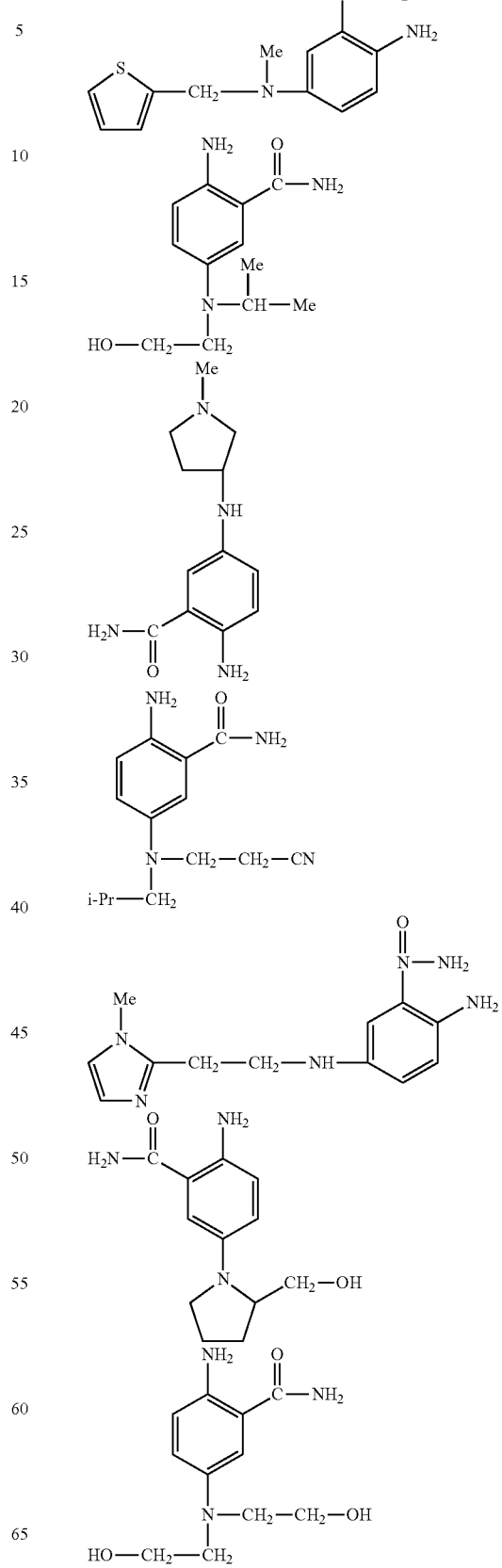

151
-continued
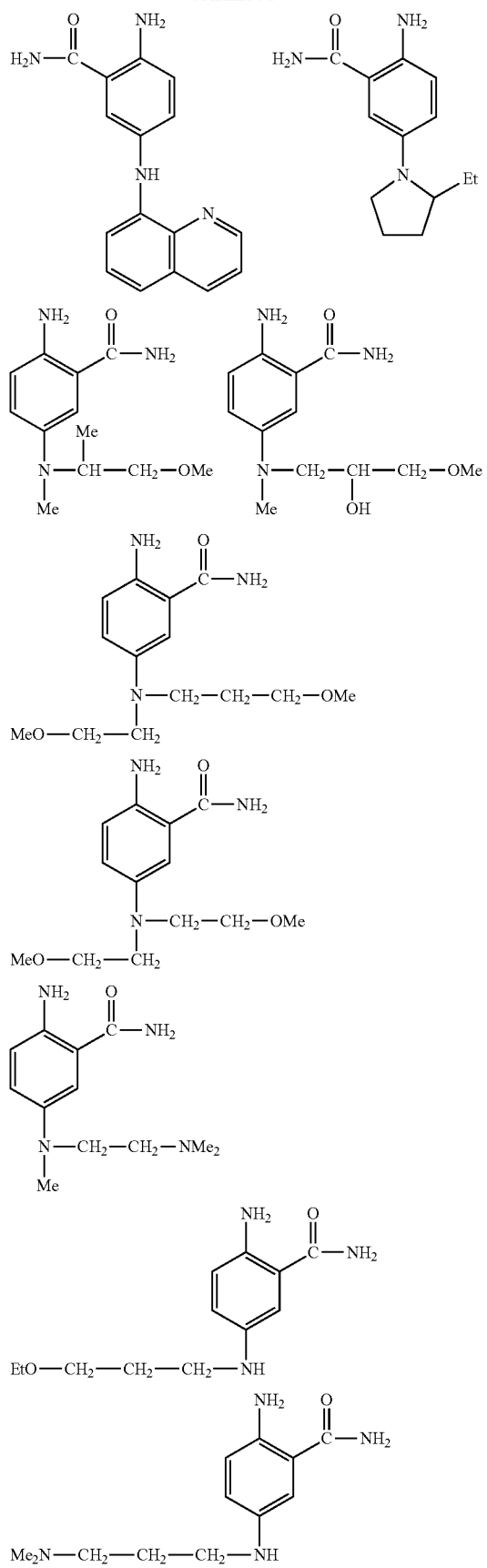
152
-continued
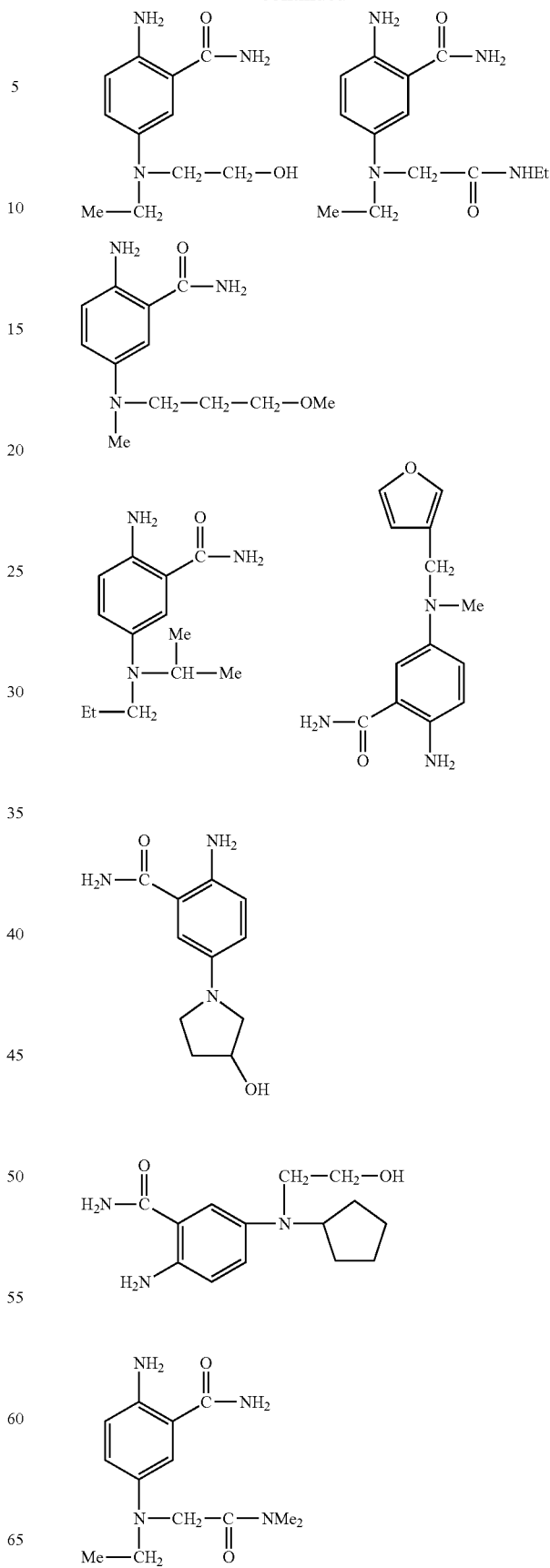

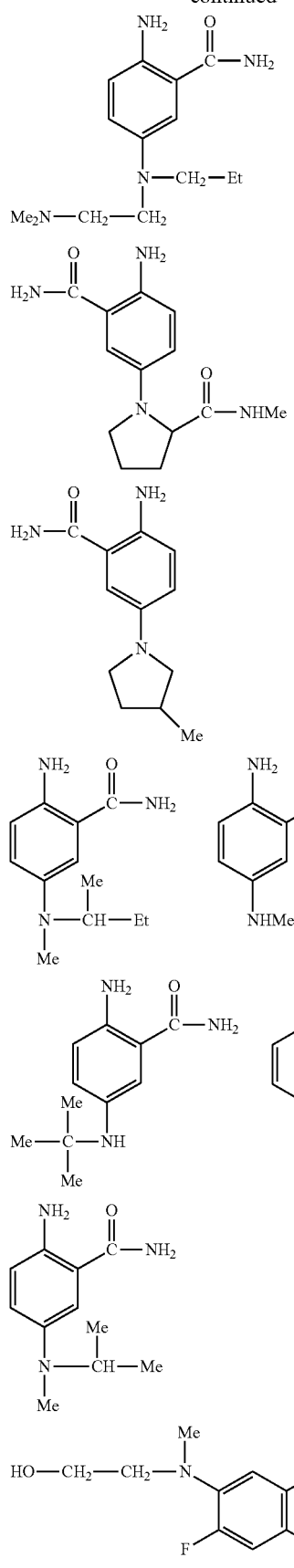
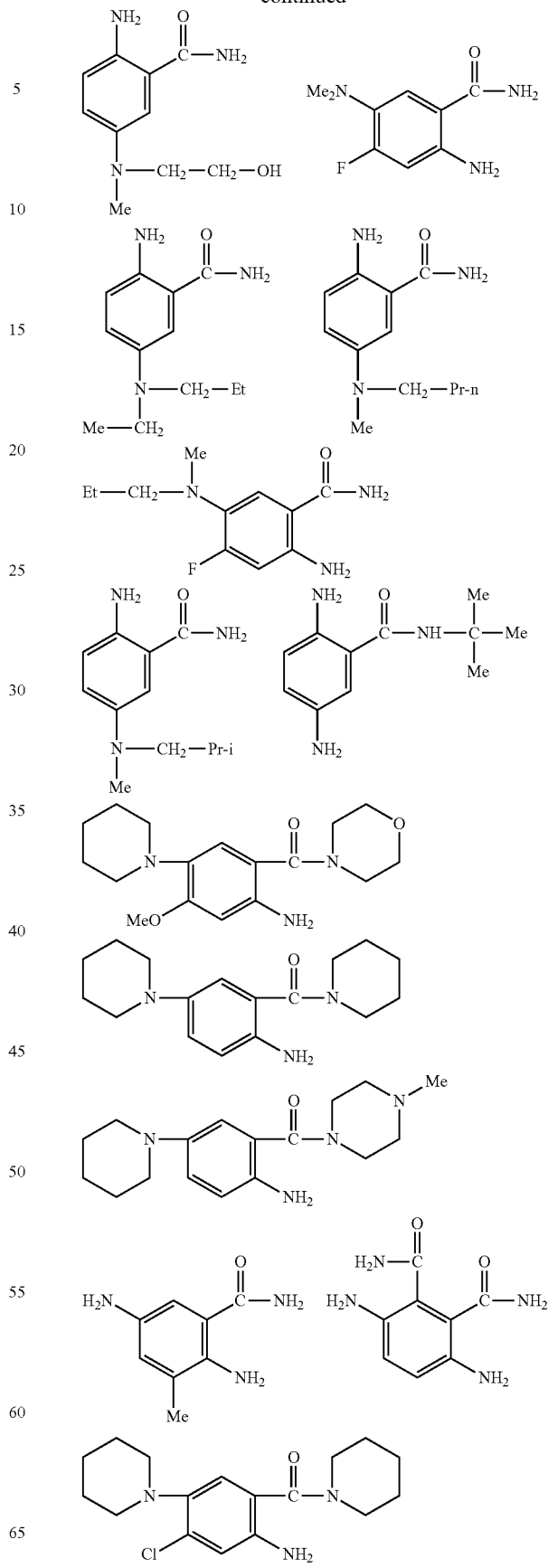

155
-continued
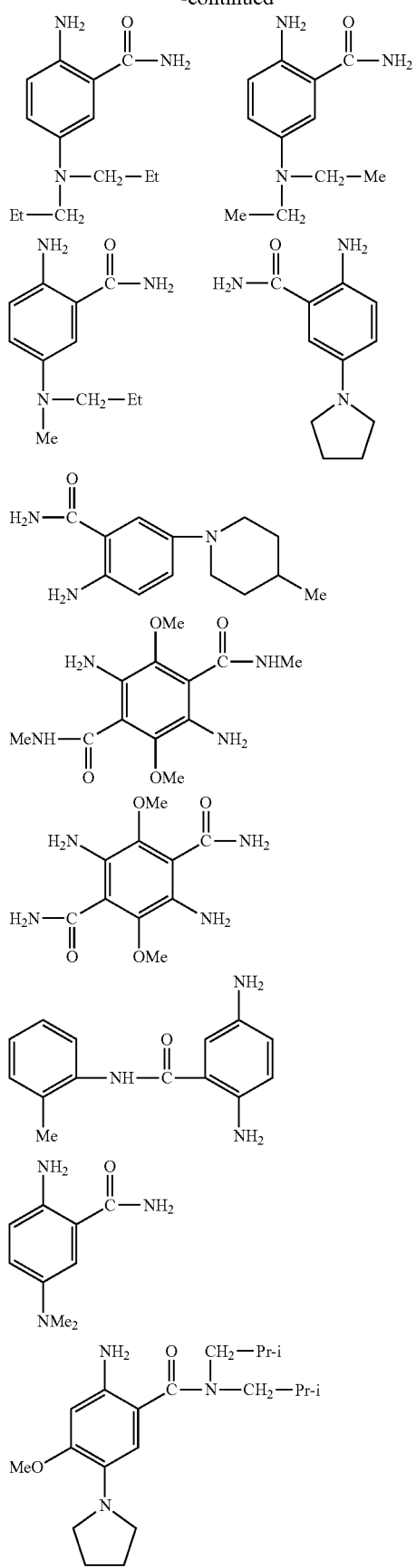
156
-continued
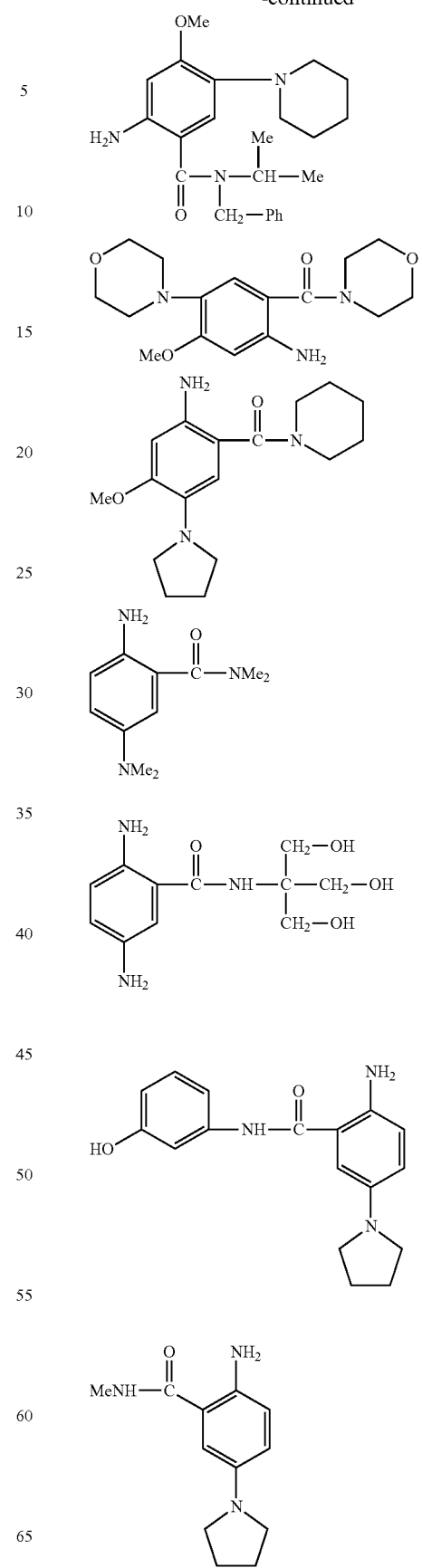

157
-continued
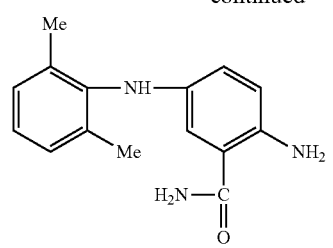
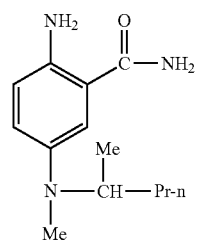
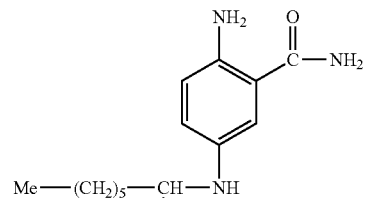
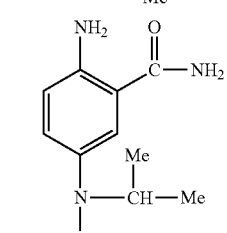
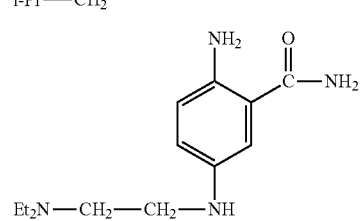
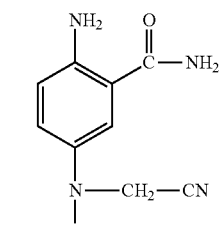
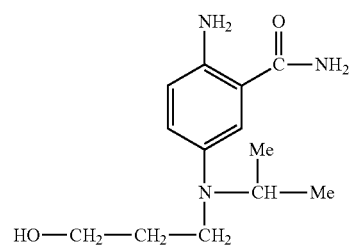
158
-continued
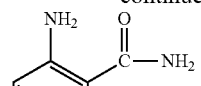
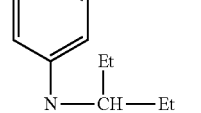
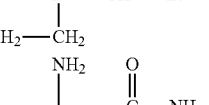
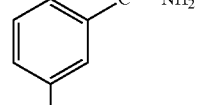
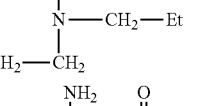
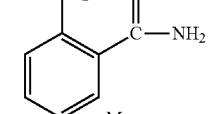
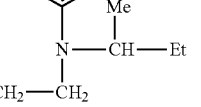
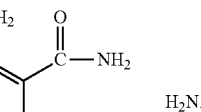
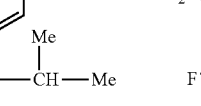
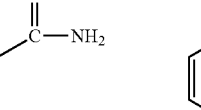
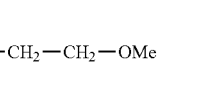
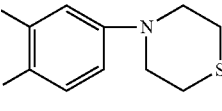
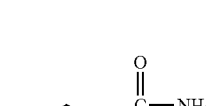
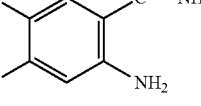

-continued

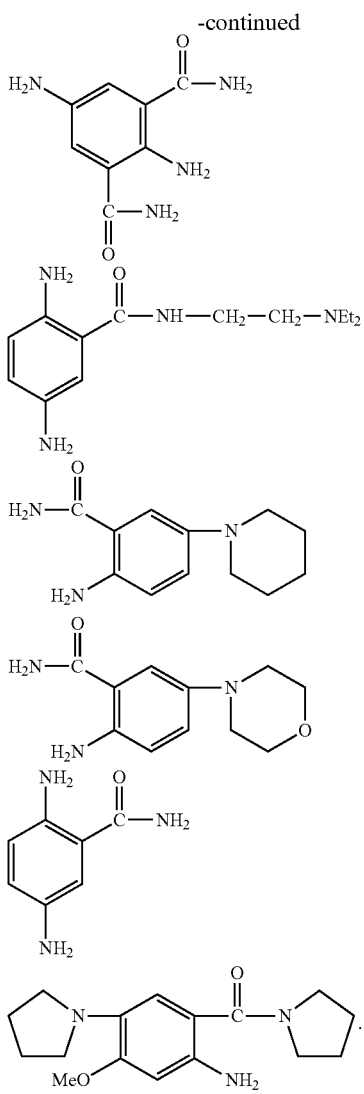

11. The method according to claim 2, wherein the at least one oxidation base is chosen from compounds of formula (II) wherein at least two of the $R_4$ groups represent hydrogen atoms.

12. The method according to claim 2, wherein the at least one oxidation base is chosen from compounds of formula (II) wherein:

Z represents an amino group optionally substituted with one or two $C_1$-$C_4$ alkyl radicals, which may be identical or different, and $R_1$ represents an amino radical —$NR_{11}R_{12}$, wherein $R_{11}$ and $R_{12}$, which may be identical or different, are chosen from:
- a hydrogen atom;
- a $C_1$-$C_{20}$ alkyl radical, optionally bearing at least one group chosen from:
  - a hydroxyl, $C_1$-$C_{15}$ alkoxy, or phenoxy group;
  - a —COOH group;
  - a —$SO_3H$ group;
  - a cyano group;
  - a ($C_1$-$C_4$)alkylcarbonyl amino (or ($C_2$-$C_4$)acylamino) group, or mono- or di-($C_1$-$C_4$)alkylaminocarbonyl;
  - an amino, optionally substituted with one or two $C_1$-$C_4$ alkyl radicals, which may be identical or different;
  - a saturated or unsaturated, aromatic or non-aromatic heterocycle having from 5 to 7 ring members, optionally containing from 1 to 3 endocyclic heteroatoms chosen from nitrogen, oxygen or sulfur, the nitrogen optionally bearing a hydrogen or a $C_1$-$C_4$ alkyl; or
  - a $C_6$-$C_{10}$ aryl radical comprising an aromatic nucleus, or two fused aromatic nuclei, the aryl radical being optionally substituted with at least one $C_1$-$C_4$ alkyl, hydroxyl, $C_1$-$C_4$ alkoxy, or trifluoromethyl radical,
- a $C_6$-$C_{10}$ aryl radical comprising an aromatic nucleus optionally fused to another (hetero)aromatic nucleus, wherein the heteroatom is nitrogen, the aryl radical being optionally substituted with at least one group chosen from $C_1$-$C_4$ alkyl, hydroxyl, $C_1$-$C_4$ alkoxy, cyano, trifluoromethyl, halogen, ($C_1$-$C_4$)alkylcarbonylamino, amino, aminosulfonyl, $C_2$-$C_4$ alkynyl, or $NH_2$—$C(=NH_2)$—;
- a saturated or unsaturated, aromatic or non-aromatic heterocycle having from 5 to 6 ring members, comprising from one to four heteroatoms, nitrogen, or oxygen;

with the proviso that the $R_{11}$ and $R_{12}$ radicals may optionally form, together with the nitrogen atom to which they are attached, a heterocycle having from 5 to 7 ring members, optionally fused to a $C_6$ aromatic nucleus, which is cationic or non-cationic, saturated or unsaturated, and aromatic or non-aromatic, optionally containing one endocyclic additional heteroatom chosen from nitrogen, oxygen, or sulfur; the nitrogen optionally bearing one or two $C_1$-$C_4$ alkyls, which may be identical or different, the alkyl group optionally bearing an —$SO_3H$ group; the heterocycle being optionally substituted on at least one of its carbon atoms with one or two groups, which may be identical or different, chosen from a $C_1$-$C_4$alkyl radical optionally bearing a hydroxyl radical, a hydroxyl radical, an aminocarbonyl radical or a mono- or di-($C_1$-$C_4$)alkylaminocarbonyl radical.

13. The method according to claim 2, wherein the oxidation base of formula (I) and/or (II), salts thereof or solvates thereof, is present in an amount ranging from about 0.001% to about 20% by weight relative to the weight of composition (A).

14. The method according to claim 2, wherein the at least one metal catalyst is chosen from metal salts; metal oxides; metal complexes; transition metal salts; rare earth metal salts; inorganic metal salts; inorganic metal halides; inorganic metal carbonates; inorganic metal sulfates; inorganic metal phosphates; hydrated inorganic metal halides; metal salts of organic acid chosen from citrates, lactates, glycolates, gluconates, acetates, propionates, fumarates, oxalates, or tartrates; metal salts bearing a metal in oxidation state II and two (poly)hydroxy acid-derived ligands; the metal salts being optionally complexed with two carboxylate groups corresponding to compounds of formula (III); solvates thereof, or mixtures thereof:

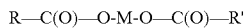

R—C(O)—O-M-O—C(O)—R'  (III)

wherein:

M is chosen from a metal (II) or metal$^{2+}$ in oxidation state II, and

R and R', which may be identical or different, represent a $(C_1-C_6)$(poly)hydroxyalkyl group.

15. The method according to claim 2, wherein the at least one fatty substance is chosen from $C_6-C_{16}$ hydrocarbons, the hydrocarbons containing more than 16 carbon atoms, non-silicone oils of animal origin, triglycerides of plant or synthetic origin, fluoro oils, fatty alcohols, esters of fatty acids and/or of fatty alcohols other than triglycerides and non-silicone waxes, non-silicone waxes other than fatty alcohols, silicones, liquid petroleum jelly, $C_6-C_{16}$ alkanes, polydecenes, liquid esters of fatty acids and/or of fatty alcohols other than triglycerides, liquid fatty alcohols, 2-octyldodecanol, or mixtures thereof.

16. The method according to claim 2, wherein the at least one fatty substance is present in an amount ranging from about 10% to about 80% by weight, relative to the total weight of the composition.

17. The method according to claim 2, wherein the composition further comprises at least one basifying agent chosen from organic amines with a $pK_b$ of less than 12, alkanolamines, monoethanolamine, basic amino acids, compounds comprising a guanidine function, mineral bases, aqueous ammonia, alkali carbonates or bicarbonates, sodium or potassium carbonate or bicarbonate, sodium or potassium hydroxides metasilicates, sodium metasilicate, potassium metasilicate, or mixtures thereof.

18. The method according to claim 2, wherein:
the at least one metal catalyst is present in a second composition (B) separate from the composition (A); and
the method further comprises:
mixing the composition (A) and the composition (B), and applying the mixture of compositions (A) and (B) to wet or dry keratin fibers; or
applying the composition (A) and the composition (B) successively to wet or dry keratin fibers and optionally rinsing the keratin fibers between applying composition (A) and composition (B).

19. The method according to claim 2, wherein the composition (A) is obtained by mixing a composition (A1) comprising the at least one oxidation base chosen from the compounds of formula (I), addition salts thereof, or solvates thereof, a composition (A2) comprising the at least one chemical oxidizing agent other than atmospheric oxygen and optionally, a composition (A3) comprising the at least one fatty substance.

20. A multi-compartment device for dyeing keratin fibers, comprising:
a first compartment containing a composition (B) comprising at least one metal catalyst;
a second compartment containing a composition (A1) comprising at least one oxidation base chosen from compounds of formula (I), the addition salts thereof, solvates thereof, or mixtures thereof:

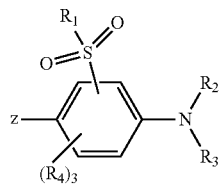

(I)

wherein:
$R_1$ is chosen from:
a hydroxyl radical,
a $C_1-C_{10}$ alkyl radical optionally bearing at least one hydroxyl, $C_1-C_4$ alkoxy, —O—$SO_3H$, —$SO_3H$, —COOH, halo group, or fluoro,
an amino radical optionally substituted with one or two identical or different groups, chosen from:
a $C_1-C_{20}$ linear or $C_3-C_{20}$ branched or cyclic alkyl group or a $C_3-C_{20}$ linear or branched alkenyl group, the alkyl or alkenyl group optionally bearing at least one hydroxyl or $C_1-C_4$ alkoxy radical optionally substituted with a hydroxyl group, an amino optionally substituted with one or two identical or different $C_1-C_4$ alkyl groups, pyridyl, furyl, or combinations thereof; the alkyl or alkenyl group optionally forming, together with the nitrogen atom that bears them, a saturated or unsaturated 5- to 7-membered heterocycle optionally comprising one or two identical or different additional endocyclic heteroatoms, chosen from nitrogen, oxygen or sulfur, the heterocycle being optionally substituted on a carbon or nitrogen atom with at least one $C_1-C_4$ alkyl radical, and the heterocycle being optionally fused to a phenyl nucleus;
a R'$SO_2$— group wherein R' is chosen from a $C_1-C_4$ alkyl or phenyl radical;
benzyl ($C_6H_6$—$CH_2$—), phenyl, or naphthyl groups optionally substituted with at least one $C_1-C_4$ alkyl group; trifluoromethyl or hydroxyl groups; a $C_1-C_{20}$ alkoxy group; an amino group; a sulfonic (—$SO_3H$) group; a halogen atom, or chlorine; or
a saturated, unsaturated, or aromatic 5- or 6-membered heterocycle comprising one to three identical or different endocyclic heteroatoms, nitrogen, or sulfur,
a phenyl or benzyl radical, optionally substituted with at least one radical chosen from $C_1-C_6$ alkyl, $C_1-C_{20}$ alkoxy, hydroxyl, amino, trifluoromethyl, a $(C_1-C_4)$ alkylamido (alk-CONH—) groups, a sulfonic (—$SO_3H$) group, a halogen atom, or chlorine;
$R_2$ and $R_3$, which may be identical or different, are chosen from a hydrogen atom or a $C_1-C_4$ alkyl radical,
$R_4$, which may be identical or different, is chosen from a hydrogen atom, a $C_1-C_4$ alkyl radical, a $C_1-C_4$ alkoxy radical, a carboxylic (—COOH) group, a sulfonic (—$SO_3H$) group, a $(C_1-C_4)$alkyl($C_6$)arylsulfonyl (alk-aryl-$SO_2$—) group, a sulfonamido ($NH_2$—$SO_2$—) group, a halogen, chlorine, or bromine,
with the proviso that two radicals $R_4$ borne by adjacent carbon atoms may optionally form, with the carbon atoms, a saturated, unsaturated or aromatic 6-membered ring, optionally comprising an endocyclic nitrogen atom, the ring being optionally fused to another 6-membered aromatic nucleus or optionally substituted with a $(C_1-C_4)$alkylamido (alk-CONH—) or sulfonic (—$SO_3H$) radical; and
Z is chosen from a hydroxyl group or an amino group optionally substituted with one or two identical or different radicals $R_6$ chosen from:
a linear $C_1-C_{10}$ alkyl or branched $C_3-C_{10}$ alkyl radical,
the linear $C_1-C_{10}$ alkyl or branched $C_3-C_{10}$ alkyl radical optionally interrupted with a heteroatom chosen from oxygen, an amino group optionally substituted with a $C_1-C_4$ alkyl radical, or an ammonium group substituted with three identical or different $C_1-C_4$ alkyl radicals;
the alkyl radical optionally bearing at least one group chosen from:

a hydroxyl radical;

an amino radical optionally substituted with a $C_1$-$C_4$ alkyl group;

an ammonium radical substituted with three identical or different $C_1$-$C_4$ alkyl groups, wherein at least one of the groups is optionally substituted with a —COOH group or a hydroxyl group;

a phenyl optionally bearing a radical —$SO_2$—$R_7$ wherein $R_7$ is a $C_1$-$C_4$ alkyl radical, optionally bearing a hydroxyl radical, or an amino group;

a —O—$SO_3H$ group;

a —$SO_3H$ group;

a —COOH group;

a radical —$SO_2$—$R_7$ wherein $R_7$ is chosen from a $C_1$-$C_4$ alkyl radical, a phenyl group optionally bearing a hydroxyl radical, an amino group, or an ammonium radical comprising three identical or different radicals chosen from $C_1$-$C_4$ alkyls optionally bearing a carboxylic group in acid or salified form; or a —NHCO—$R_8$ or —NH—CO—NH—$R_8$ group, wherein $R_8$ is chosen from a phenyl group or a $C_1$-$C_4$ alkyl radical, optionally bearing a carboxylic group;

a benzyl radical or a phenyl radical,
optionally substituted with at least one group chosen from:
a $C_1$-$C_4$ alkyl radical optionally bearing at least one hydroxyl radical;
a hydroxyl radical;
a $C_1$-$C_4$ alkoxy radical;
a halogen atom or chlorine;
an amino radical optionally substituted with one or two $C_1$-$C_4$ alkyl groups optionally bearing a hydroxyl;
a sulfonic group (—$SO_3H$); or
a radical —$SO_2$-$R_9$ wherein $R_9$ is a $C_1$-$C_4$ alkyl radical, optionally bearing a hydroxyl radical or an amino group,
with the proviso that two radicals borne by adjacent carbon atoms may form, together with the carbon atoms, a 6-membered heterocycle; the heterocycle comprising one or two endocyclic oxygen atoms;

two alkyl radicals $R_6$, which may form, together with the nitrogen atom that bears them, a saturated or unsaturated 5- to 7-membered heterocycle, the heterocycle optionally comprising another endocyclic group having a heteroatom, —O—, —S—, or —$NR_{10}$, wherein $R_{10}$ is chosen from a hydrogen atom or a $C_1$-$C_4$ alkyl radical optionally substituted with a hydroxyl group;

the heterocycle being optionally fused with a phenyl nucleus;

the heterocycle being optionally substituted on one of its carbon atoms with a group chosen from: a $C_1$-$C_4$ alkyl radical optionally bearing a hydroxyl radical; an amino radical optionally substituted with one or two identical or different radicals $R_{11}$ chosen from a $C_1$-$C_4$ alkyl radical optionally bearing a hydroxyl radical; or an amino radical optionally substituted with one or two identical or different $C_1$-$C_4$ alkyl radicals, wherein two of the radicals $R_{11}$ may form a 5- to 6-membered heterocycle optionally comprising another endocyclic heteroatom, —O—, —S—, or —$NR_{12}$, wherein $R_{12}$ is chosen from a hydrogen atom or a $C_1$-$C_4$ alkyl radical; or a radical

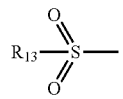

wherein $R_{13}$ is chosen from a $C_1$-$C_4$ alkyl radical or a phenyl radical;

with the proviso that if $R_1$ is a hydroxyl radical, then at least one of the groups $R_4$ or $R_6$ is not hydrogen;

a third compartment containing a composition (A2) comprising at least one chemical oxidizing agent other than atmospheric oxygen; and optionally, a fourth compartment containing a composition (A3) comprising at least one fatty substance;

wherein at least one of composition (A1) and composition (A2) optionally comprise at least one fatty substance present in an amount greater than or equal to about 10%, relative to the total weight of a mixture of composition (A1), composition (A2), and composition (A3) if present.

* * * * *